United States Patent
Fangrow, Jr.

(10) Patent No.: US 9,974,939 B2
(45) Date of Patent: *May 22, 2018

(54) MEDICAL CONNECTOR

(71) Applicant: ICU Medical, Inc., San Clemente, CA (US)

(72) Inventor: Thomas F. Fangrow, Jr., Mission Viejo, CA (US)

(73) Assignee: ICU Medical, Inc., San Clemente, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/499,740

(22) Filed: Apr. 27, 2017

(65) Prior Publication Data

US 2017/0296801 A1   Oct. 19, 2017

Related U.S. Application Data

(63) Continuation of application No. 15/091,484, filed on Apr. 5, 2016, now Pat. No. 9,636,492, which is a (Continued)

(51) Int. Cl.
*A61M 39/10* (2006.01)
*A61M 39/12* (2006.01)
(Continued)

(52) U.S. Cl.
CPC ............ *A61M 39/10* (2013.01); *A61M 39/12* (2013.01); *A61M 39/22* (2013.01); *A61M 39/26* (2013.01); *A61M 2039/1033* (2013.01); *A61M 2039/1066* (2013.01); *A61M 2039/261* (2013.01); *A61M 2039/263* (2013.01); *A61M 2039/267* (2013.01); *A61M 2039/268* (2013.01); *Y10T 137/87973* (2015.04)

(58) Field of Classification Search
CPC .................. A61M 39/26; A61M 39/10; A61M 2039/263; A61M 2039/267; A61M 39/045; A61M 2039/261
See application file for complete search history.

(56) References Cited

U.S. PATENT DOCUMENTS

| 2,254,997 A | 9/1941 | Fisher |
| 2,456,045 A | 12/1948 | Brock |

(Continued)

FOREIGN PATENT DOCUMENTS

| CA | 2747283 A1 | 7/2002 |
| EP | 0 158 030 | 10/1985 |

(Continued)

OTHER PUBLICATIONS

U.S. Appl. No. 11/417,648, filed May 3, 2006, Gustus et al.
(Continued)

*Primary Examiner* — Aarti B Berdichevsky
(74) *Attorney, Agent, or Firm* — Knobbe Martens Olson & Bear, LLP

(57) ABSTRACT

A medical connector includes a housing with a central axis, a hollow bore, and a narrowed passage. The connector further includes a rigid valve member configured to move along the axis of the connector as the connector moves between an open and closed configuration. The connector includes a resilient member coupled to the valve member and the housing.

14 Claims, 47 Drawing Sheets

Related U.S. Application Data continuation of application No. 14/329,372, filed on Jul. 11, 2014, now Pat. No. 9,358,379, which is a continuation of application No. 13/534,663, filed on Jun. 27, 2012, now Pat. No. 8,777,908, which is a continuation of application No. 12/893,789, filed on Sep. 29, 2010, now Pat. No. 8,211,069, which is a continuation of application No. 11/482,176, filed on Jul. 6, 2006, now Pat. No. 7,815,614.

(60) Provisional application No. 60/707,319, filed on Aug. 11, 2005, provisional application No. 60/696,894, filed on Jul. 6, 2005.

(51) Int. Cl.
*A61M 39/22* (2006.01)
*A61M 39/26* (2006.01)

(56) References Cited

U.S. PATENT DOCUMENTS

| | | |
|---|---|---|
| 2,842,382 A | 7/1958 | Franck |
| 2,931,668 A | 4/1960 | Baley |
| 2,968,497 A | 1/1961 | Treleman |
| 3,127,892 A | 4/1964 | Bellamy, Jr. et al. |
| 3,304,047 A | 2/1967 | Martin |
| 3,334,860 A | 8/1967 | Bolton, Jr. |
| 3,707,972 A | 1/1973 | Villari et al. |
| 3,729,031 A | 4/1973 | Baldwin |
| 3,824,556 A | 7/1974 | Berkovits et al. |
| 3,986,508 A | 10/1976 | Barrington |
| 4,055,179 A | 10/1977 | Manschot et al. |
| 4,066,067 A | 1/1978 | Micheli |
| 4,076,285 A | 2/1978 | Martinez |
| 4,080,965 A | 3/1978 | Phillips |
| 4,084,606 A | 4/1978 | Mittleman |
| 4,121,585 A | 10/1978 | Becker, Jr. |
| 4,133,441 A | 1/1979 | Mittleman et al. |
| 4,143,853 A | 3/1979 | Abramson |
| 4,150,845 A | 4/1979 | Kopacz et al. |
| 4,187,848 A | 2/1980 | Taylor |
| 4,195,632 A | 4/1980 | Parker et al. |
| 4,233,982 A | 11/1980 | Bauer et al. |
| 4,245,635 A | 1/1981 | Kontos |
| 4,324,239 A | 4/1982 | Gordon et al. |
| 4,334,551 A | 6/1982 | Pfister |
| 4,340,049 A | 7/1982 | Munsch |
| 4,379,458 A | 4/1983 | Bauer et al. |
| 4,387,879 A | 6/1983 | Tauschinski |
| 4,397,442 A | 8/1983 | Larkin |
| 4,430,073 A | 2/1984 | Bemis et al. |
| 4,436,125 A | 3/1984 | Blenkush |
| 4,457,749 A | 7/1984 | Bellotti et al. |
| 4,511,359 A | 4/1985 | Vaillancourt |
| 4,538,836 A | 9/1985 | Kruetten |
| 4,576,359 A | 3/1986 | Oetiker |
| 4,610,469 A | 9/1986 | Wolff-Mooij |
| 4,619,640 A | 10/1986 | Potolsky et al. |
| 4,623,332 A | 11/1986 | Lindmayer et al. |
| 4,629,159 A | 12/1986 | Wellenstam |
| 4,660,803 A | 4/1987 | Johnston et al. |
| 4,662,878 A | 5/1987 | Lindmayer |
| 4,673,400 A | 6/1987 | Martin |
| 4,700,744 A | 10/1987 | Rutter et al. |
| 4,723,603 A | 2/1988 | Plummer |
| 4,723,948 A | 2/1988 | Clark et al. |
| 4,728,075 A | 3/1988 | Paradis |
| 4,745,950 A | 5/1988 | Mathieu |
| 4,758,023 A | 7/1988 | Vermillion |
| 4,774,964 A | 10/1988 | Bonaldo |
| 4,774,965 A | 10/1988 | Rodriguez et al. |
| 4,781,702 A | 11/1988 | Herrli |
| 4,804,015 A | 2/1989 | Albinsson |
| 4,816,024 A | 3/1989 | Sitar et al. |
| 4,819,692 A | 4/1989 | Olson et al. |
| 4,834,271 A | 5/1989 | Litwin |
| 4,844,512 A | 7/1989 | Gahwiler |
| 4,862,913 A | 9/1989 | Wildfang |
| 4,863,201 A | 9/1989 | Carstens |
| 4,883,483 A | 11/1989 | Lindmayer |
| 4,915,687 A | 4/1990 | Sivert |
| 4,917,669 A | 4/1990 | Bonaldo |
| 4,935,010 A | 6/1990 | Cox et al. |
| 4,949,745 A | 8/1990 | McKeon |
| 4,950,260 A | 8/1990 | Bonaldo |
| D313,277 S | 12/1990 | Haining |
| D314,050 S | 1/1991 | Sone |
| 5,006,114 A | 4/1991 | Rogers et al. |
| 5,021,059 A | 6/1991 | Kensey et al. |
| 5,047,021 A | 9/1991 | Utterberg |
| 5,065,783 A | 11/1991 | Ogle, II |
| 5,066,286 A | 11/1991 | Ryan |
| 5,070,885 A | 12/1991 | Bonaldo |
| 5,083,819 A | 1/1992 | Bynum |
| 5,098,385 A | 3/1992 | Walsh |
| 5,108,376 A | 4/1992 | Bonaldo |
| 5,122,123 A | 6/1992 | Vaillancourt |
| 5,139,483 A | 8/1992 | Ryan |
| 5,147,333 A | 9/1992 | Raines |
| 5,154,703 A | 10/1992 | Bonaldo |
| 5,176,406 A | 1/1993 | Straghan |
| RE34,223 E | 4/1993 | Bonaldo |
| 5,199,948 A | 4/1993 | McPhee |
| 5,201,717 A | 4/1993 | Wyatt et al. |
| 5,201,725 A | 4/1993 | Kling |
| 5,203,775 A | 4/1993 | Frank et al. |
| 5,211,634 A | 5/1993 | Vaillancourt |
| 5,215,537 A | 6/1993 | Lynn et al. |
| 5,215,538 A | 6/1993 | Larkin |
| 5,242,393 A | 9/1993 | Brimhall et al. |
| 5,242,425 A | 9/1993 | White et al. |
| 5,251,873 A | 10/1993 | Atkinson et al. |
| 5,269,771 A | 12/1993 | Thomas et al. |
| 5,273,533 A | 12/1993 | Bonaldo |
| 5,279,571 A | 1/1994 | Larkin |
| 5,281,206 A | 1/1994 | Lopez |
| 5,284,475 A | 2/1994 | Mackal |
| 5,295,657 A | 3/1994 | Atkinson |
| 5,301,686 A | 4/1994 | Newman |
| 5,306,243 A | 4/1994 | Bonaldo |
| 5,312,377 A | 5/1994 | Dalton |
| 5,324,270 A | 6/1994 | Kayan et al. |
| 5,330,450 A | 7/1994 | Lopez |
| 5,334,159 A | 8/1994 | Turkel |
| 5,344,414 A | 9/1994 | Lopez et al. |
| 5,360,413 A | 11/1994 | Leason et al. |
| 5,370,636 A | 12/1994 | Von Witzleben |
| 5,380,306 A | 1/1995 | Brinon |
| 5,385,372 A | 1/1995 | Utterberg |
| 5,390,898 A | 2/1995 | Smedley et al. |
| 5,391,150 A | 2/1995 | Richmond |
| 5,395,348 A | 3/1995 | Ryan |
| 5,397,314 A | 3/1995 | Farley et al. |
| 5,400,500 A | 3/1995 | Behnke et al. |
| 5,401,245 A | 3/1995 | Haining |
| 5,402,826 A | 4/1995 | Molnar et al. |
| 5,402,982 A | 4/1995 | Atkinson et al. |
| 5,405,323 A | 4/1995 | Rogers et al. |
| 5,405,331 A | 4/1995 | Behnke et al. |
| 5,405,333 A | 4/1995 | Richmond |
| 5,411,499 A | 5/1995 | Dudar et al. |
| 5,417,673 A | 5/1995 | Gordon |
| 5,423,791 A | 6/1995 | Bartlett |
| 5,425,465 A | 6/1995 | Healy |
| 5,433,330 A | 7/1995 | Yatsko et al. |
| 5,439,451 A | 8/1995 | Collinson et al. |
| 5,441,487 A | 8/1995 | Vedder |
| 5,445,623 A | 8/1995 | Richmond |
| 5,447,177 A | 9/1995 | Ricken et al. |
| 5,456,668 A | 10/1995 | Ogle, II |
| 5,456,675 A | 10/1995 | Wolbring et al. |
| 5,462,255 A | 10/1995 | Rosen et al. |
| 5,464,399 A | 11/1995 | Boettger |

(56) References Cited

U.S. PATENT DOCUMENTS

| | | |
|---|---|---|
| 5,470,319 A | 11/1995 | Mayer |
| 5,470,327 A | 11/1995 | Helgren et al. |
| 5,474,536 A | 12/1995 | Bonaldo |
| 5,480,393 A | 1/1996 | Bommarito |
| 5,489,274 A | 2/1996 | Chu et al. |
| 5,492,147 A | 2/1996 | Challender et al. |
| 5,501,426 A | 3/1996 | Atkinson et al. |
| 5,507,744 A | 4/1996 | Tay et al. |
| 5,514,177 A | 5/1996 | Kurz et al. |
| 5,518,026 A | 5/1996 | Benjey |
| 5,520,665 A | 5/1996 | Fleetwood |
| 5,520,666 A | 5/1996 | Choudhury et al. |
| 5,527,284 A | 6/1996 | Ohnemus et al. |
| 5,533,708 A | 7/1996 | Atkinson et al. |
| 5,533,983 A | 7/1996 | Haining |
| 5,533,996 A | 7/1996 | Murphey et al. |
| 5,535,785 A | 7/1996 | Werge et al. |
| 5,540,661 A | 7/1996 | Tomisaka et al. |
| 5,549,566 A | 8/1996 | Elias et al. |
| 5,549,577 A | 8/1996 | Siegel et al. |
| 5,549,651 A | 8/1996 | Lynn |
| 5,552,118 A | 9/1996 | Mayer |
| 5,555,908 A | 9/1996 | Edwards et al. |
| 5,569,235 A | 10/1996 | Ross et al. |
| 5,573,516 A | 11/1996 | Tyner |
| 5,575,769 A | 11/1996 | Vaillancourt |
| 5,578,059 A | 11/1996 | Patzer |
| 5,584,819 A | 12/1996 | Kopfer |
| 5,591,137 A | 1/1997 | Stevens |
| 5,591,143 A | 1/1997 | Trombley, III et al. |
| 5,597,536 A | 1/1997 | Mayer |
| 5,616,129 A | 4/1997 | Mayer |
| 5,616,130 A | 4/1997 | Mayer |
| RE35,539 E | 6/1997 | Bonaldo |
| 5,643,224 A | 7/1997 | Szapiro et al. |
| 5,645,538 A | 7/1997 | Richmond |
| 5,651,776 A | 7/1997 | Appling et al. |
| 5,674,206 A | 10/1997 | Allton et al. |
| 5,676,346 A | 10/1997 | Leinsing |
| 5,685,866 A | 11/1997 | Lopez |
| 5,685,868 A | 11/1997 | Lundquist |
| 5,699,821 A | 12/1997 | Paradis |
| 5,700,248 A | 12/1997 | Lopez |
| 5,702,374 A | 12/1997 | Johnson |
| 5,735,826 A | 4/1998 | Richmond |
| 5,738,144 A | 4/1998 | Rogers |
| 5,749,861 A | 5/1998 | Guala et al. |
| RE35,841 E | 7/1998 | Frank et al. |
| 5,782,816 A | 7/1998 | Werschmidt et al. |
| 5,784,750 A | 7/1998 | Sankovic et al. |
| 5,785,693 A | 7/1998 | Haining |
| 5,788,215 A | 8/1998 | Ryan |
| 5,806,831 A | 9/1998 | Paradis |
| 5,810,398 A | 9/1998 | Matkovich |
| 5,814,024 A | 9/1998 | Thompson et al. |
| 5,820,601 A | 10/1998 | Mayer |
| 5,820,614 A | 10/1998 | Erksine et al. |
| 5,830,189 A | 11/1998 | Chang |
| 5,839,715 A | 11/1998 | Leinsing |
| 5,848,994 A | 12/1998 | Richmond |
| 5,947,954 A | 9/1999 | Bonaldo |
| 6,029,946 A | 2/2000 | Doyle |
| 6,036,171 A | 3/2000 | Weinheimer et al. |
| 6,041,805 A | 3/2000 | Gydesen et al. |
| 6,050,978 A | 4/2000 | Orr et al. |
| 6,063,062 A | 5/2000 | Paradis |
| 6,068,011 A | 5/2000 | Paradis |
| 6,068,617 A | 5/2000 | Richmond |
| 6,079,432 A | 6/2000 | Paradis |
| 6,106,502 A | 8/2000 | Richmond |
| 6,113,068 A | 9/2000 | Ryan |
| 6,142,446 A | 11/2000 | Leinsing |
| 6,152,913 A | 11/2000 | Feith et al. |
| 6,168,137 B1 | 1/2001 | Paradis |
| 6,170,522 B1 | 1/2001 | Tanida |
| 6,171,287 B1 | 1/2001 | Lynn et al. |
| 6,189,859 B1 | 2/2001 | Rohrbough et al. |
| 6,206,860 B1 | 3/2001 | Richmond |
| 6,221,029 B1 | 4/2001 | Mathis et al. |
| 6,224,578 B1 | 5/2001 | Davis et al. |
| 6,242,393 B1 | 6/2001 | Ishida et al. |
| 6,245,048 B1 | 6/2001 | Fangrow et al. |
| 6,290,206 B1 | 9/2001 | Doyle |
| 6,299,132 B1 | 10/2001 | Weinheimer et al. |
| 6,325,100 B1 | 12/2001 | Bunschoten et al. |
| 6,402,207 B1 | 6/2002 | Segal et al. |
| 6,428,520 B1 | 8/2002 | Lopez |
| 6,431,219 B1 | 8/2002 | Redler et al. |
| 6,485,472 B1 | 11/2002 | Richmond |
| 6,499,719 B1 | 12/2002 | Clancy et al. |
| 6,508,792 B2 | 1/2003 | Szames et al. |
| 6,508,807 B1 | 1/2003 | Peters |
| 6,541,802 B2 | 4/2003 | Doyle |
| 6,543,745 B1 | 4/2003 | Enerson |
| 6,581,906 B2 | 6/2003 | Pott et al. |
| 6,585,229 B2 | 7/2003 | Cote et al. |
| 6,595,964 B2 | 7/2003 | Finley et al. |
| 6,595,981 B2 | 7/2003 | Huet |
| 6,609,696 B2 | 8/2003 | Enerson |
| 6,612,624 B1 | 9/2003 | Segal et al. |
| 6,666,852 B2 | 12/2003 | Niedospial, Jr. |
| 6,673,059 B2 | 1/2004 | Guala |
| 6,695,817 B1 | 2/2004 | Fangrow |
| 6,745,998 B2 | 6/2004 | Doyle |
| 6,808,161 B1 | 10/2004 | Hishikawa |
| 6,840,501 B2 | 1/2005 | Doyle |
| 6,843,513 B2 | 1/2005 | Guala |
| 6,869,426 B2 | 3/2005 | Ganem |
| 6,875,205 B2 | 4/2005 | Leinsing |
| 6,893,056 B2 | 5/2005 | Guala |
| 6,899,315 B2 | 5/2005 | Mailville et al. |
| 6,911,025 B2 | 6/2005 | Miyahara |
| 6,955,669 B2 | 10/2005 | Curutcharry |
| 6,964,406 B2 | 11/2005 | Doyle |
| 7,004,934 B2 | 2/2006 | Vaillancourt |
| 7,037,302 B2 | 5/2006 | Vaillancourt |
| 7,040,598 B2 | 5/2006 | Raybuck |
| 7,044,441 B2 | 5/2006 | Doyle |
| 7,100,891 B2 | 9/2006 | Doyle |
| 7,125,396 B2 | 10/2006 | Leinsing et al. |
| 7,137,654 B2 | 11/2006 | Segal et al. |
| 7,140,592 B2 | 11/2006 | Phillips |
| 7,182,313 B2 | 2/2007 | Doyle |
| 7,195,228 B2 | 3/2007 | Tiberghien et al. |
| 7,244,249 B2 | 7/2007 | Leinsing et al. |
| 7,306,197 B2 | 12/2007 | Parrino et al. |
| 7,306,198 B2 | 12/2007 | Doyle |
| 7,306,566 B2 | 12/2007 | Raybuck |
| 7,316,679 B2 | 1/2008 | Bierman |
| 7,347,458 B2 | 3/2008 | Rome et al. |
| 7,350,764 B2 | 4/2008 | Raybuck |
| 7,361,164 B2 | 4/2008 | Simpson et al. |
| 7,497,484 B2 | 3/2009 | Ziman |
| 7,559,530 B2 | 7/2009 | Korogi et al. |
| 7,588,563 B2 | 9/2009 | Guala |
| 7,628,781 B2 | 12/2009 | Roy et al. |
| 7,645,274 B2 | 1/2010 | Whitley |
| 7,651,481 B2 | 1/2010 | Raybuck |
| 7,666,170 B2 | 2/2010 | Guala |
| 7,722,090 B2 | 5/2010 | Burton et al. |
| 7,758,566 B2 | 7/2010 | Simpson et al. |
| 7,766,304 B2 | 8/2010 | Phillips |
| 7,766,897 B2 | 8/2010 | Ramsey et al. |
| 7,803,139 B2 | 9/2010 | Fangrow, Jr. |
| 7,803,140 B2 | 9/2010 | Fangrow, Jr. |
| 7,815,614 B2 | 10/2010 | Fangrow, Jr. |
| 7,837,658 B2 | 11/2010 | Cote et al. |
| 7,857,805 B2 | 12/2010 | Raines |
| 7,875,019 B2 | 1/2011 | Barron et al. |
| 7,976,532 B2 | 7/2011 | Kitani et al. |
| 7,998,134 B2 | 8/2011 | Fangrow et al. |
| 8,066,692 B2 | 11/2011 | Simpson et al. |
| 8,177,772 B2 | 5/2012 | Christensen et al. |
| 8,196,614 B2 | 6/2012 | Kriheli |

(56) References Cited

U.S. PATENT DOCUMENTS

| | | | |
|---|---|---|---|
| 8,211,069 B2 | 7/2012 | Fangrow, Jr. |
| 8,225,826 B2 | 7/2012 | Horppu et al. |
| 8,262,628 B2 | 9/2012 | Fangrow, Jr. |
| 8,286,936 B2 | 10/2012 | Kitani et al. |
| 8,287,513 B2 | 10/2012 | Ellstrom et al. |
| 8,414,554 B2 | 4/2013 | Garfield et al. |
| 8,414,555 B2 | 4/2013 | Garfield et al. |
| 8,454,579 B2 | 6/2013 | Fangrow, Jr. |
| 8,556,868 B2 | 10/2013 | Simpson et al. |
| 8,647,310 B2 | 2/2014 | Fangrow, Jr. et al. |
| 8,679,090 B2 | 3/2014 | Anderson et al. |
| 8,721,628 B2 | 5/2014 | Ziman |
| 8,777,908 B2 | 7/2014 | Fangrow, Jr. |
| 8,777,909 B2 | 7/2014 | Fangrow, Jr. |
| 8,864,737 B2 | 10/2014 | Hasegawa et al. |
| 8,888,758 B2 | 11/2014 | Mansour et al. |
| 8,899,267 B2 | 12/2014 | Diodati et al. |
| 9,114,242 B2 | 8/2015 | Fangrow et al. |
| 9,126,028 B2 | 9/2015 | Fangrow et al. |
| 9,126,029 B2 | 9/2015 | Fangrow et al. |
| 9,168,366 B2 | 10/2015 | Fangrow et al. |
| 9,345,641 B2 | 5/2016 | Kraus et al. |
| 9,358,379 B2 | 6/2016 | Fangrow |
| 9,636,492 B2 | 5/2017 | Fangrow, Jr. |
| 9,707,346 B2 | 7/2017 | Simpson et al. |
| 2001/0029355 A1 | 10/2001 | Szames et al. |
| 2002/0066715 A1 | 6/2002 | Niedospial, Jr. |
| 2003/0060804 A1 | 3/2003 | Vaillancourt |
| 2003/0066978 A1 | 4/2003 | Enerson |
| 2003/0111623 A1 | 6/2003 | Enerson |
| 2003/0136932 A1 | 7/2003 | Doyle |
| 2003/0208165 A1 | 11/2003 | Christensen et al. |
| 2004/0074541 A1 | 4/2004 | Sharpe |
| 2004/0124388 A1 | 7/2004 | Kiehne |
| 2004/0124389 A1 | 7/2004 | Phillips |
| 2004/0244848 A1 | 12/2004 | Maldavs |
| 2005/0015075 A1 | 1/2005 | Wright et al. |
| 2005/0124942 A1 | 6/2005 | Richmond |
| 2005/0212292 A1 | 9/2005 | Parrino et al. |
| 2005/0228362 A1 | 10/2005 | Vaillancourt |
| 2005/0245872 A1 | 11/2005 | Simpson et al. |
| 2006/0025751 A1 | 2/2006 | Roy et al. |
| 2006/0058734 A1 | 3/2006 | Phillips |
| 2006/0065873 A1 | 3/2006 | Doyle |
| 2006/0129109 A1 | 6/2006 | Shaw et al. |
| 2006/0142730 A1 | 6/2006 | Proulx et al. |
| 2006/0142735 A1 | 6/2006 | Whitley |
| 2006/0149213 A1 | 7/2006 | Raybuck |
| 2006/0157984 A1 | 7/2006 | Rome et al. |
| 2006/0161115 A1 | 7/2006 | Fangrow |
| 2006/0163514 A1 | 7/2006 | Doyle |
| 2006/0192164 A1 | 9/2006 | Korogi et al. |
| 2006/0202146 A1 | 9/2006 | Doyle |
| 2006/0253084 A1 | 11/2006 | Nordgren |
| 2007/0043334 A1 | 2/2007 | Guala |
| 2007/0088292 A1 | 4/2007 | Fangrow |
| 2007/0088293 A1 | 4/2007 | Fangrow |
| 2007/0088294 A1 | 4/2007 | Fangrow |
| 2007/0088324 A1 | 4/2007 | Fangrow |
| 2007/0088327 A1 | 4/2007 | Guala |
| 2007/0102923 A1 | 5/2007 | Niemela |
| 2007/0179453 A1 | 8/2007 | Lim et al. |
| 2008/0103485 A1 | 5/2008 | Kruger |
| 2008/0190485 A1 | 8/2008 | Guala |
| 2008/0287920 A1 | 11/2008 | Fangrow et al. |
| 2008/0290657 A1 | 11/2008 | McKeon, III |
| 2010/0063482 A1 | 3/2010 | Mansour et al. |
| 2010/0253070 A1 | 10/2010 | Cheon et al. |
| 2011/0046572 A1 | 2/2011 | Fangrow |
| 2011/0276035 A1 | 11/2011 | Fangrow, Jr. |
| 2011/0306931 A1 | 12/2011 | Kamen et al. |
| 2012/0031515 A1 | 2/2012 | Whitaker |
| 2012/0041391 A1 | 2/2012 | Fangrow et al. |
| 2012/0046636 A1 | 2/2012 | Kriheli |
| 2012/0089101 A1 | 4/2012 | Carlyon et al. |
| 2012/0316536 A1 | 12/2012 | Carrez et al. |
| 2013/0006211 A1 | 1/2013 | Takemoto |
| 2013/0231616 A1 | 9/2013 | Fangrow, Jr. |
| 2013/0304037 A1 | 11/2013 | Fangrow |
| 2014/0020792 A1 | 1/2014 | Kraus et al. |
| 2014/0246616 A1 | 9/2014 | Fangrow |
| 2015/0051555 A1 | 2/2015 | Fangrow, Jr. |
| 2016/0263367 A1 | 9/2016 | Fangrow et al. |
| 2016/0271327 A1 | 9/2016 | Simpson et al. |
| 2018/0015275 A1 | 1/2018 | Fangrow |

FOREIGN PATENT DOCUMENTS

| | | |
|---|---|---|
| EP | 0 368 473 A2 | 5/1990 |
| EP | 0 791 371 | 8/1997 |
| EP | 0 795 342 | 9/1997 |
| EP | 1 946 792 | 7/2008 |
| GB | 2 116 277 | 9/1983 |
| GB | 2 118 440 | 11/1983 |
| GB | 2 353 078 | 2/2001 |
| JP | 56-72659 | 6/1981 |
| JP | 58-13216 | 1/1983 |
| JP | 59-41429 | 3/1984 |
| JP | 60-89488 | 6/1985 |
| JP | 63-175383 | 11/1988 |
| JP | 11-311234 | 11/1999 |
| JP | 2001-187990 A | 7/2001 |
| JP | 2004-000483 A | 1/2004 |
| WO | WO 1995/32748 | 12/1995 |
| WO | WO 2001/03756 | 1/2001 |
| WO | WO 2001/23026 | 4/2001 |
| WO | WO 2002/096500 | 12/2002 |
| WO | WO 2003/013646 | 2/2003 |
| WO | WO 2004/060474 | 7/2004 |
| WO | WO 2004/082756 | 9/2004 |
| WO | WO 2006/020635 | 2/2006 |
| WO | WO 2006/076656 | 7/2006 |
| WO | WO 2006/088858 | 8/2006 |
| WO | WO 2006/124756 | 11/2006 |
| WO | WO 2008/144447 | 11/2008 |
| WO | WO 2011/139995 | 11/2011 |
| WO | WO 2013/036854 | 3/2013 |

OTHER PUBLICATIONS

U.S. Appl. No. 11/417,671, filed May 3, 2006, Gustus et al.
U.S. Appl. No. 11/417,882, filed May 3, 2006, Gustus et al.
U.S. Appl. No. 11/417,909, filed May 3, 2006, Gustus et al.
U.S. Appl. No. 11/417,923, filed May 3, 2006, Gustus et al.
U.S. Appl. No. 14/020,579, filed Oct. 22, 2015, Fangrow et al.
U.S. Appl. No. 15/169,606, filed May 31, 2016, Simpson et al.
Air Embolism and Exsanguination from Separation of Two-Piece Side Port/Hemostasis Valve Cardiac Catheter Introducers, ECRI Institute, Jan. 1995, in 2 pages, http://www.mdsr.ecri.org/summary/detail.aspx?doc_id=8098.
EPO Examination Report re EP Application No. 08 755 612.2, dated Nov. 20, 2013 in 5 pages.
EPO Examination Report re EP Application No. 08 755 612.2, dated Dec. 5, 2012 in 6 pages.
EPO Search Report re EP Application No. 08 755 612.2, dated Feb. 23, 2012 in 5 pages.
Injection Site, Molded Products, Inc., Apr. 2, 2004, in 1 page, https://web.archive.org/web/20040402123354/https://www.moldedproducts.com/injectionsite.htm.
International Preliminary Report on Patentability, International Application No. PCT/US2008/063797 dated Nov. 17, 2009 in 11 pages.
International Search Report and Written Opinion of International Application No. PCT/US2008/063797 dated Dec. 30, 2008 in 21 pages.
International Search Report for PCT/US2006/026124, dated Mar. 3, 2007 in 5 pgs.
International Written Opinion for PCT/US2006/026124, dated Jan. 10, 2008 in 11 pgs.
U.S. Appl. No. 15/648,147, filed Jul. 12, 2017, Simpson et al.

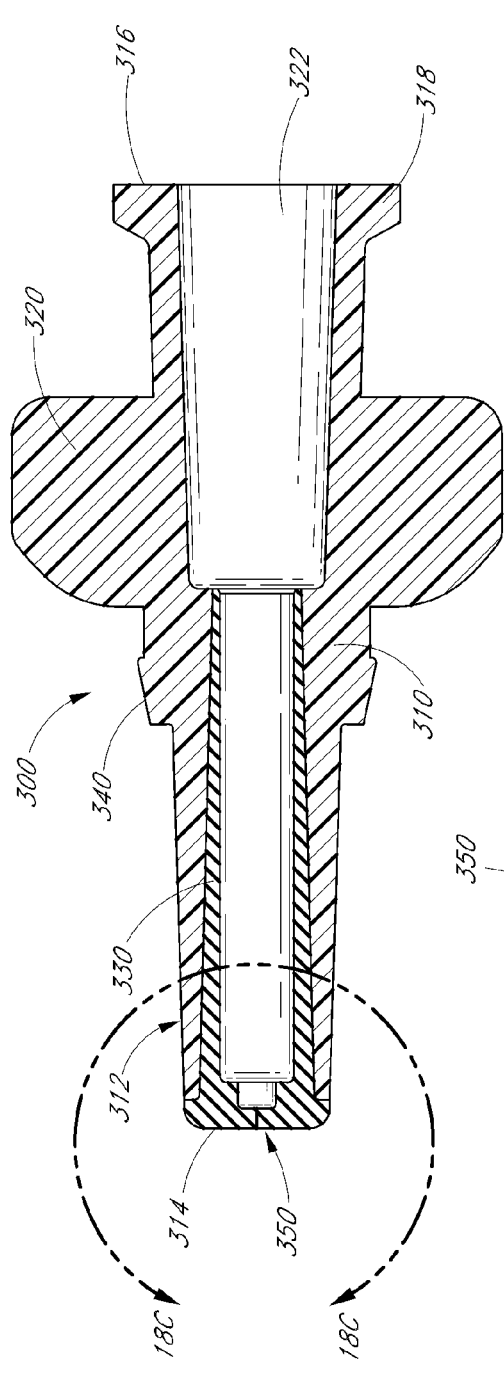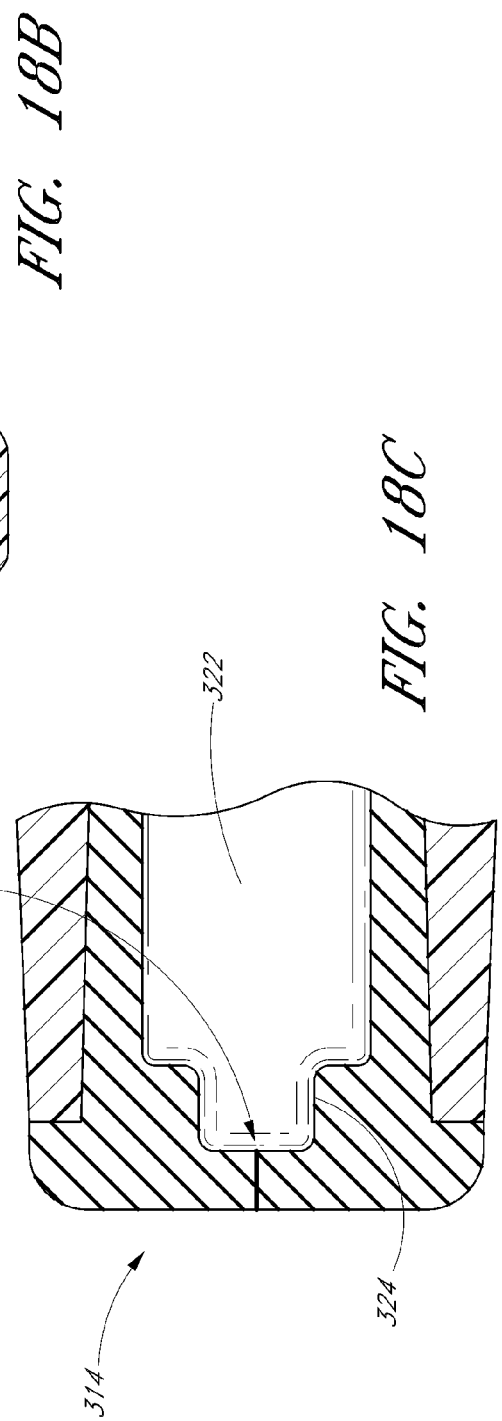
FIG. 18B
FIG. 18C

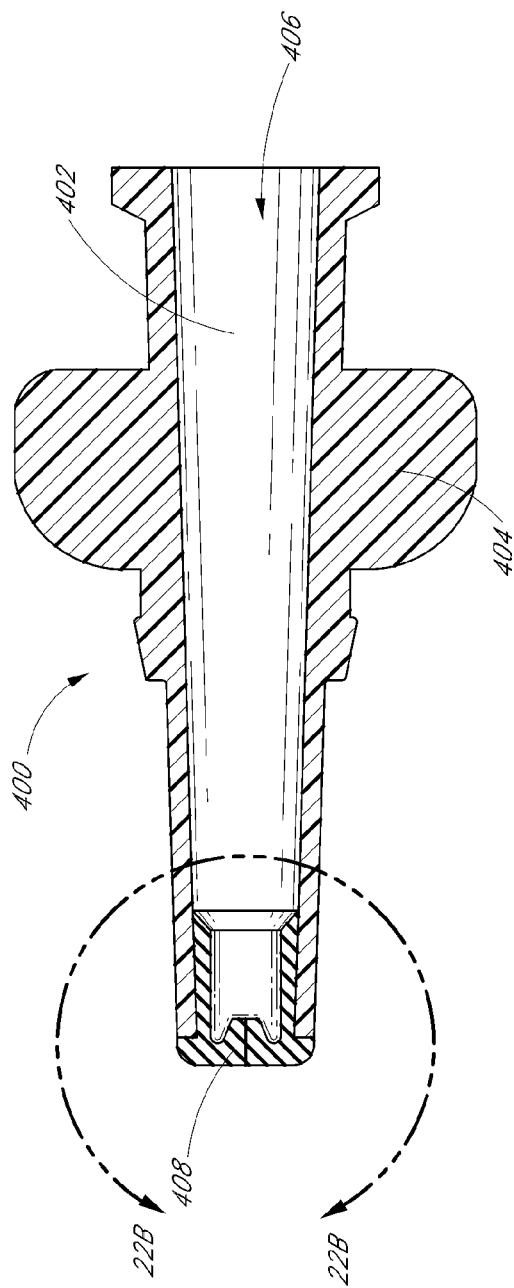
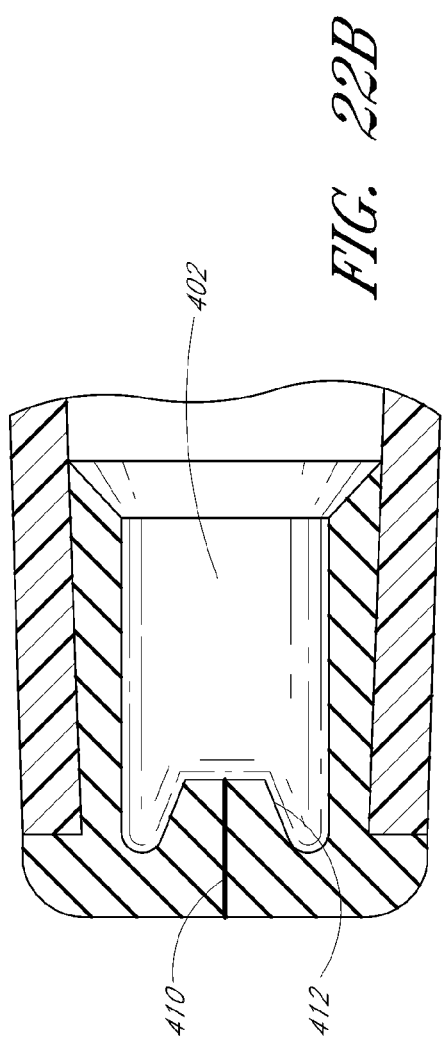
FIG. 22A
FIG. 22B

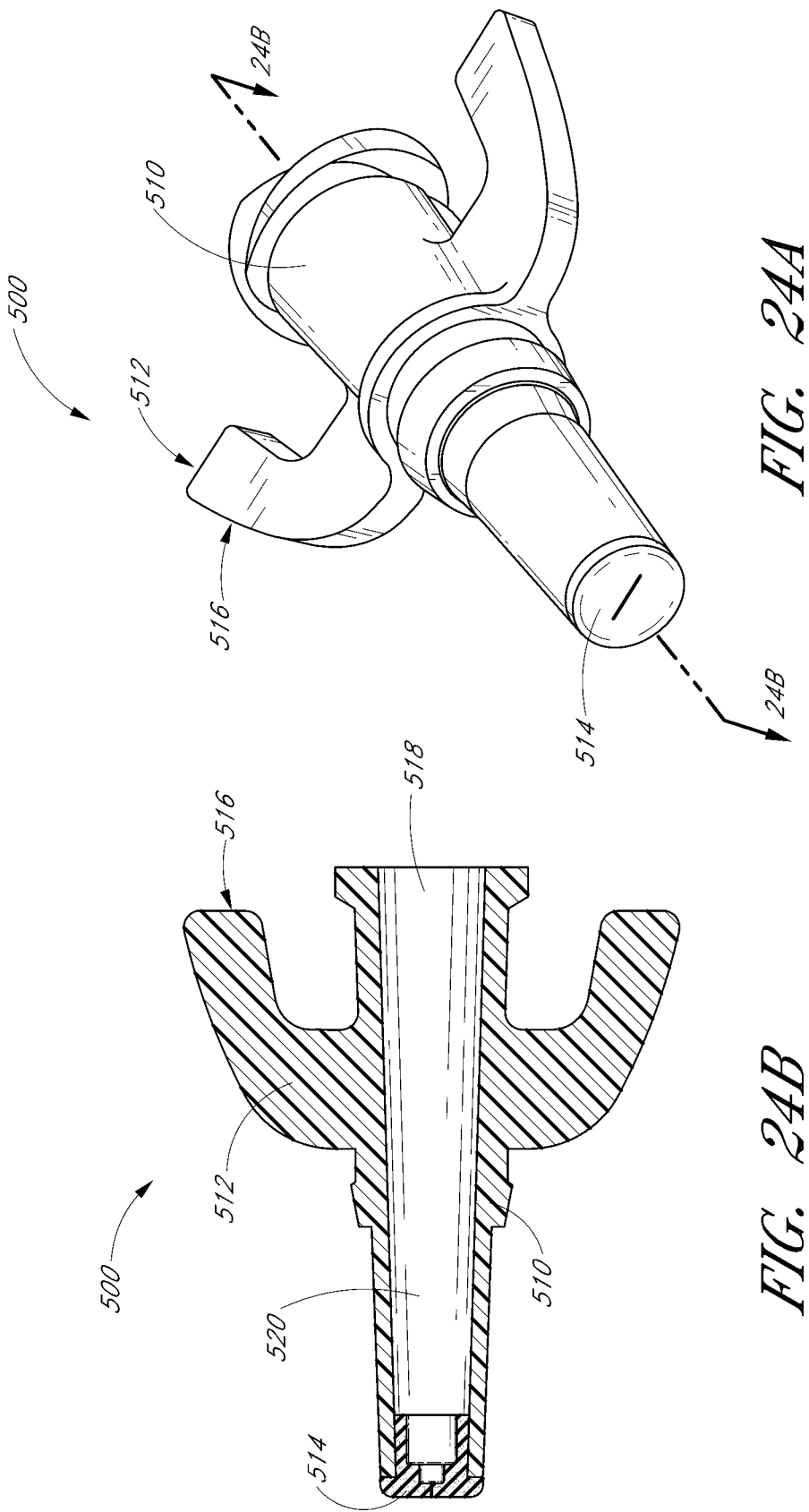

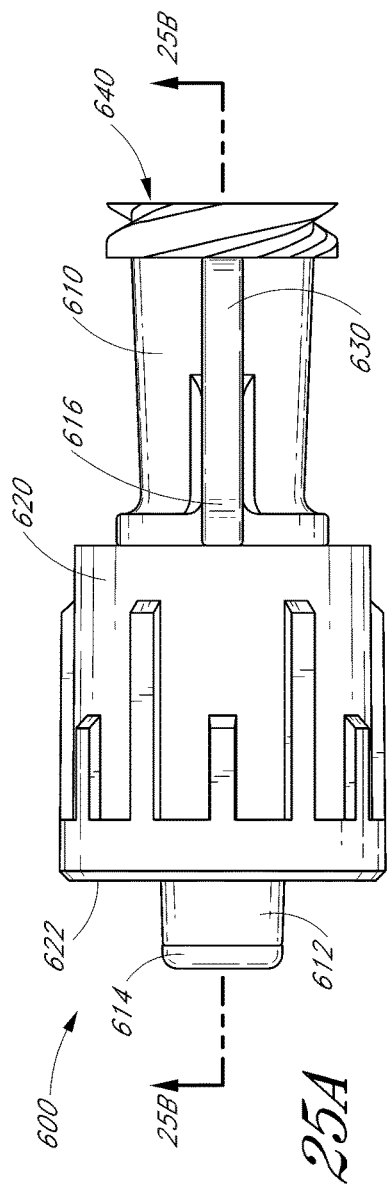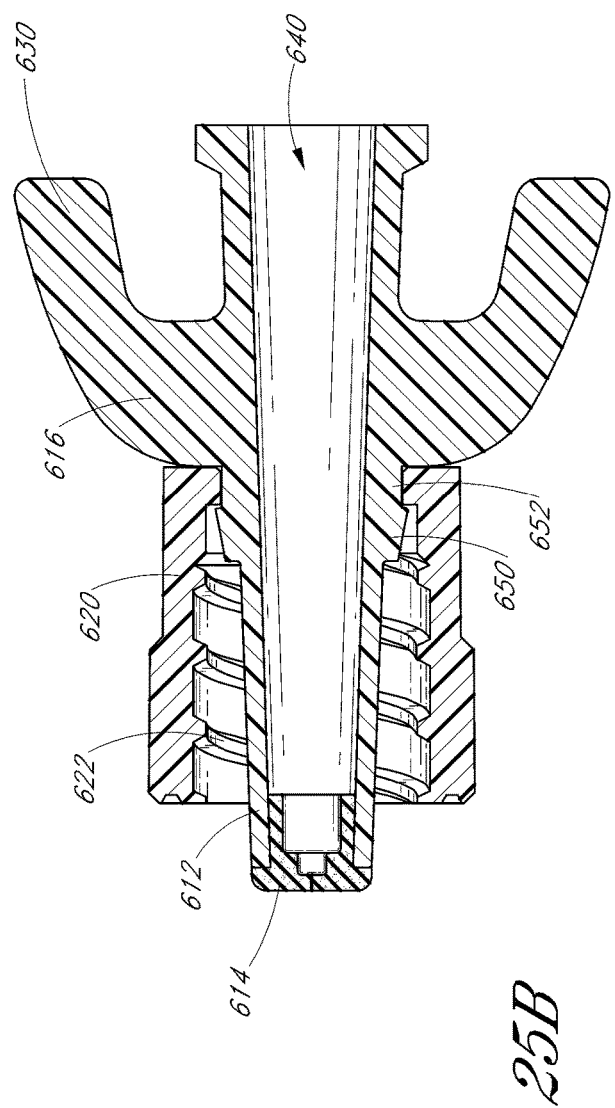
FIG. 25A
FIG. 25B

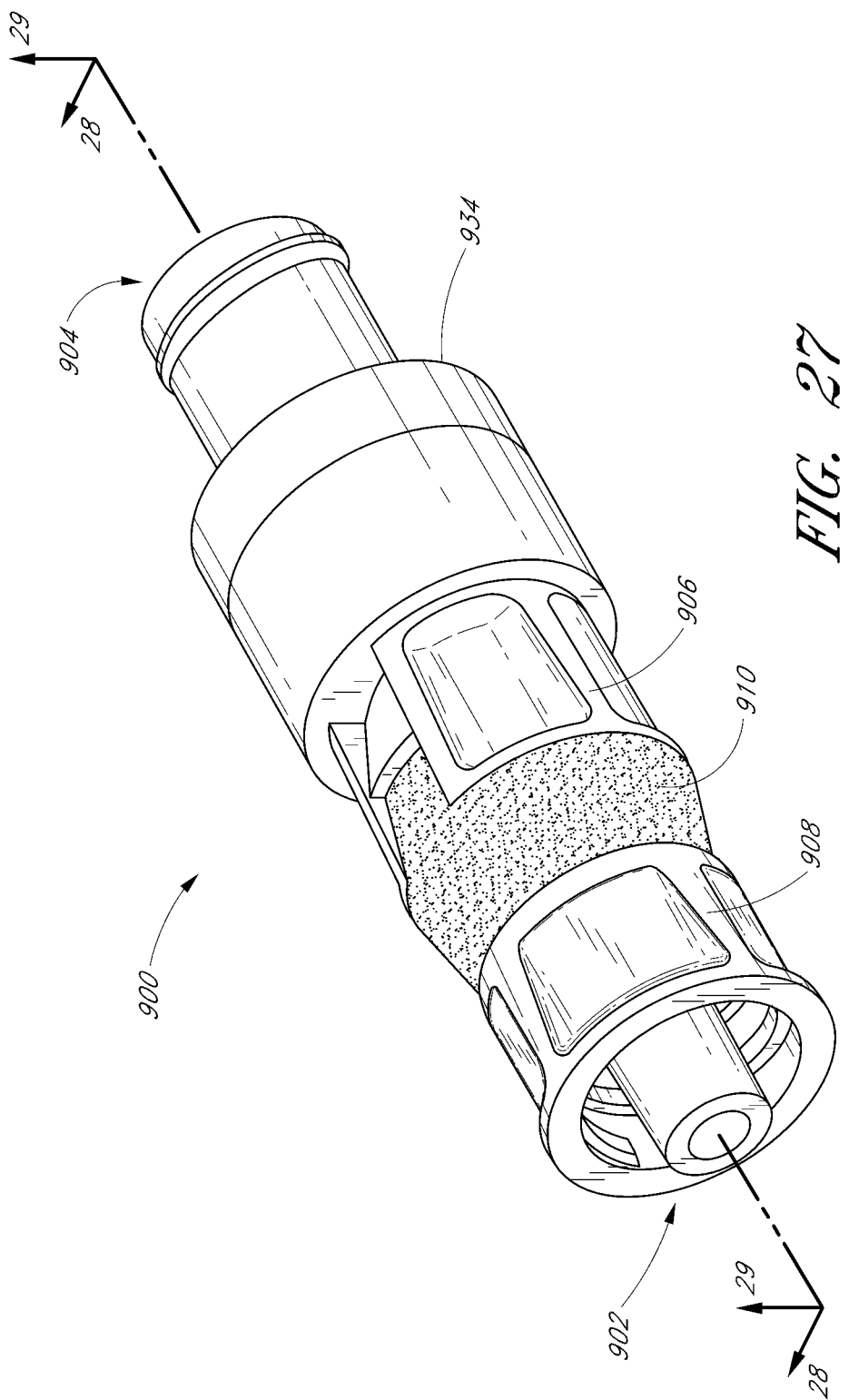

MEDICAL CONNECTOR

CROSS-REFERENCE TO RELATED APPLICATIONS

This application is a continuation application of U.S. patent application Ser. No. 15/091,484, filed Apr. 5, 2016, pending, which is a continuation application of U.S. patent application Ser. No. 14/329,372, filed Jul. 11, 2014, now U.S. Pat. No. 9,358,379, which is a continuation application of U.S. patent application Ser. No. 13/534,663, filed Jun. 27, 2012, now U.S. Pat. No. 8,777,908, which is a continuation application of U.S. patent application Ser. No. 12/893,789, filed Sep. 29, 2010, now U.S. Pat. No. 8,211,069, which is a continuation application of U.S. patent application Ser. No. 11/482,176, filed Jul. 6, 2006, now U.S. Pat. No. 7,815,614, which claims priority to U.S. Provisional Application No. 60/696,894, filed Jul. 6, 2005, and to U.S. Provisional Application No. 60/707,319, filed Aug. 11, 2005. The disclosures of the above listed applications are all hereby incorporated by reference in their entireties as if part of this disclosure.

BACKGROUND OF THE INVENTION

Field of the Invention

This invention relates generally to medical connectors through which fluids flow, and in particular, to medical connectors with male luers.

Description of the Related Art

Systems of connectors, valves, and tubing are routinely used in hospitals and other medical settings for facilitating the transfer of fluids to and from patients. It is often a challenge to keep such systems sterile and to prevent leakage of fluids when the various components are engaged and disengaged.

In order to maintain a barrier to bacteria, debris, and fluid leakage, female connectors often have been provided with closures, such as septa, flexible seals, or other impediments, at their mating ends. When a male luer connector is engaged with the female connector, the closure of the female connector is temporarily opened, pierced, or moved to allow fluid to flow between the two connectors. Male connectors typically employ needles or luers to open, pierce, or move the closure on the female connectors.

In many systems, only the female connectors are automatically blocked from the external environment when disengaged. Male luer connectors are generally not provided with automatic closing mechanisms. Male luer connectors sometimes employ additional components, such as caps, to stop the flow of fluid and impede the entry of bacteria and debris. Because such closure mechanisms are not automatic (or not used at all), male luer connectors are sometimes left unsealed, allowing fluid to drip out. This may increase the risk of unsanitary conditions inside and outside of the fluid transfer system. In addition, in some medical applications such as certain chemotherapy treatments, the fluids in the tubing and connectors can be harmful if released.

Moreover, in the busy environment of hospitals and other medical settings, health care providers must often quickly manipulate multiple medical implements with one hand, making it difficult to retrieve male luer caps and rapidly attach them upon disengagement of male connectors. In addition, male luer connectors are often employed at the downstream end of gravity-fed fluid sources such as IV bags. When the connectors and tubing are initially connected to such sources, they are generally empty (i.e., filled with air) and must be primed with fluid before they can be connected to a patient. During the priming procedure, fluid is allowed to flow from the upstream end of the tubing toward the male luer connector on the downstream end. As the flow flows through the tubing, the air in the tubing escapes through the male connector on the downstream end into the environment. Once the fluid itself reaches the male connector, it can also escape and spill out. Because male luer connectors do not usually close automatically after priming, the male luer often drips out a small amount of fluid as the male connector is rapidly moved into mating engagement with a female connector. For this reason, the male luer is generally held over a sink or trash can at the end of the priming procedure to contain the dripping fluid.

There is a need for a closable male luer connector that automatically opens when engaged with a female connector and automatically closes when disengaged from such connector to minimize or eliminate dripping during priming and other procedures and to improve the barrier of the fluid transfer system against bacteria and other debris.

SUMMARY OF THE INVENTION

Disclosed are various embodiments of medical connectors with closable male luers. It is contemplated that the features of the various embodiments disclosed herein are combinable to form additional embodiments. Such combinations are within the scope of this disclosure.

In an exemplary embodiment, a male luer connector has a main housing with first and second ends. The second end of the housing comprises a male luer and a shroud surrounding at least a portion of the male luer. The shroud has screw threads disposed on an internal wall thereof. A tubular valve member with a fluid pathway is disposed within the housing. The valve member has a tip on its second end. In the region near the tip, a pair of fluid holes is positioned on opposite sides of the valve member. The tip is configured to abut snugly against an internal wall of the male luer in a region at or near the second end of the male luer. The valve member also has a pair of struts directed towards the second end. The struts extend axially through a portion of the housing, and the ends of the struts towards the second end are positioned within a space between the male luer and the shroud on the second end of the housing. A length of medical tubing is connected to the connector. An end of the tubing is attached to the first end of the valve member by adhesive, welding, or some other means. A resilient, elastomeric member extends from a mid-section region on the outside of the housing to a region at or near the first end of the valve member within the housing.

In a substantially closed state, the resilient member is configured to pull the housing and the tubular valve member together along their respective axes. In this state, the tip of the valve member is pressed into close contact with a portion of the internal wall on the second end of the male luer, and fluid flow from the medical tubing through the tubular valve member is impeded. Fluid generally cannot escape through the opening on the second end of the male luer because such opening is blocked by the tip of the valve member.

When a force is applied to separate the valve member from the housing, the resilient member is stretched and the tip of the valve member is displaced in the direction of the first end from the second end of the male luer. This separating force can be applied manually, for example, by grasping the external wall of the housing with two fingers and grasping the tubing adhered to the first end of the valve member with two other fingers, and then moving the fingers in opposite direction. The separating force can also be applied automatically by a different manual action. For example, the action of connecting the male luer to a female end of another medical implement can automatically separate the valve member from the housing. As the advancing end of the female connector proceeds up the screw threads on the second end of the housing of the male luer connector, the female connector makes contact with and exerts a force directed towards the first end against the struts of the valve member. This force moves the valve member towards the first end against the biasing force directed towards the second end exerted by the resilient member. In this opened state, fluid is permitted to flow through the opposing holes, around the tip of the valve member, and out of the connector through the gap between the tip of the valve member and the internal wall on the second end of the male luer. In some embodiments, the valve member is automatically advanced in the direction of the first end when the valve member contacts a fluid conduit (e.g., a spike positioned within a female connector) as the male and female connectors are brought together.

When the separating force is removed, for example, by releasing the manual grip on the housing and the tubing, or by detaching the female connector from the second end of the housing, the resilient member once again draws the housing and the valve member together. This causes the tip on the second end of the valve member to abut closely against a portion of the internal wall in a region near the second end of the male luer, and impedes fluid flow out of the valve.

Also disclosed herein are other features and configurations for the foregoing embodiment, as well as additional embodiments for other connectors with closable male luers. Such embodiments generally include means for permitting or impeding fluid flow through a male luer on a connector, preferably automatically upon connection with a corresponding female connector.

BRIEF DESCRIPTION OF THE DRAWINGS

Certain embodiments of this invention will now be discussed in detail with reference to the following figures. These figures are provided for illustrative purposes only, and the invention is not limited to the subject matter illustrated in the figures.

FIG. 18B is a cross-sectional view of the connector of FIG. 18A.

FIG. 18C is a detail of the cross-sectional view of the connector of FIG. 18A.

FIG. 22A is a cross-sectional view of another embodiment of a closeable male luer connector.

FIG. 22B is a detail of the cross-sectional view of the connector of FIG. 22A.

FIG. 24A is a perspective view of another embodiment of a closeable male luer connector.

FIG. 24B is a cross-sectional view of the connector of FIG. 24A.

FIG. 25A is a side view of another embodiment of a closeable male luer connector with a shroud.

FIG. 25B is a cross-sectional view of the connector of FIG. 25A.

FIG. 27 is a perspective view of another embodiment of a closeable male luer connector.

DETAILED DESCRIPTION OF THE PREFERRED EMBODIMENT

In one aspect of the present inventions, a variety of means are shown for closing the second end of a male luer connector. In some embodiments, these closing mechanisms function to prevent and/or impede fluid from escaping from or entering into the male luer, while allowing fluid flow when the male luer is manually opened or engaged with a corresponding female luer. As used herein, terms such as "closed" or "sealed" should be understood as obstructions or barriers to fluid flow. These terms should not be understood to require that a particular structure or configuration achieves a complete fluid closure in all circumstances.

Figure 1A:
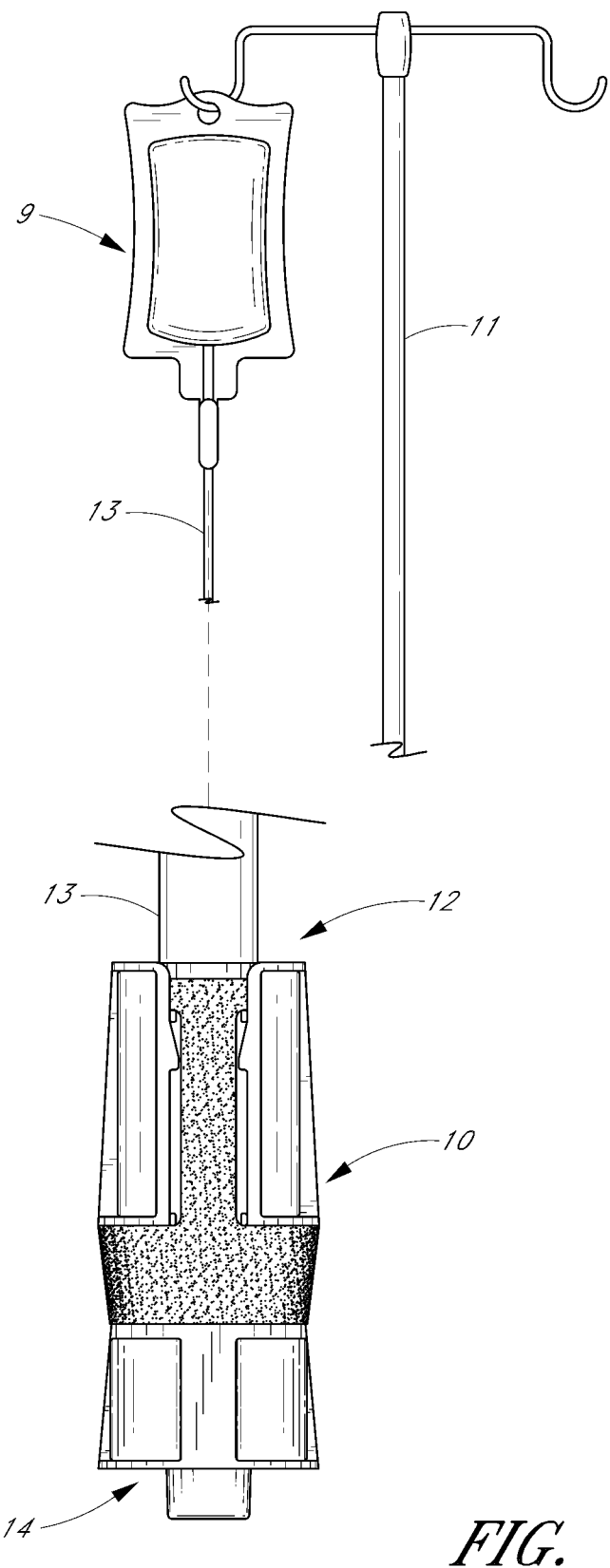
FIG. 1A shows a perspective view of an embodiment of a male luer connector attached to tubing configured to receive fluid from a hanging gravity-fed IV bag. In this and other figures, the relative size of the connector and attached tubing is increased in comparison to other objects to facilitate viewing certain details.

In FIG. 1A, an embodiment of a closable male luer connector 10 is shown in a closed position. The luer connector 10 is attached to a gravity-fed IV bag 9 filled with fluid hanging from a pole stand 11. At the bottom of the bag 9, a section of tubing 13 is attached. The opposite end of the tubing 13 is connected to the first end 12 of the luer connector 10. A closing mechanism on the interior of the second end 14 of the luer connector 10 prevents the fluid contained within the bag 9 from flowing through the tubing 13 and leaking out of the luer connector 10, as long as the luer connector 10 remains in a closed configuration.

Figure 1B:
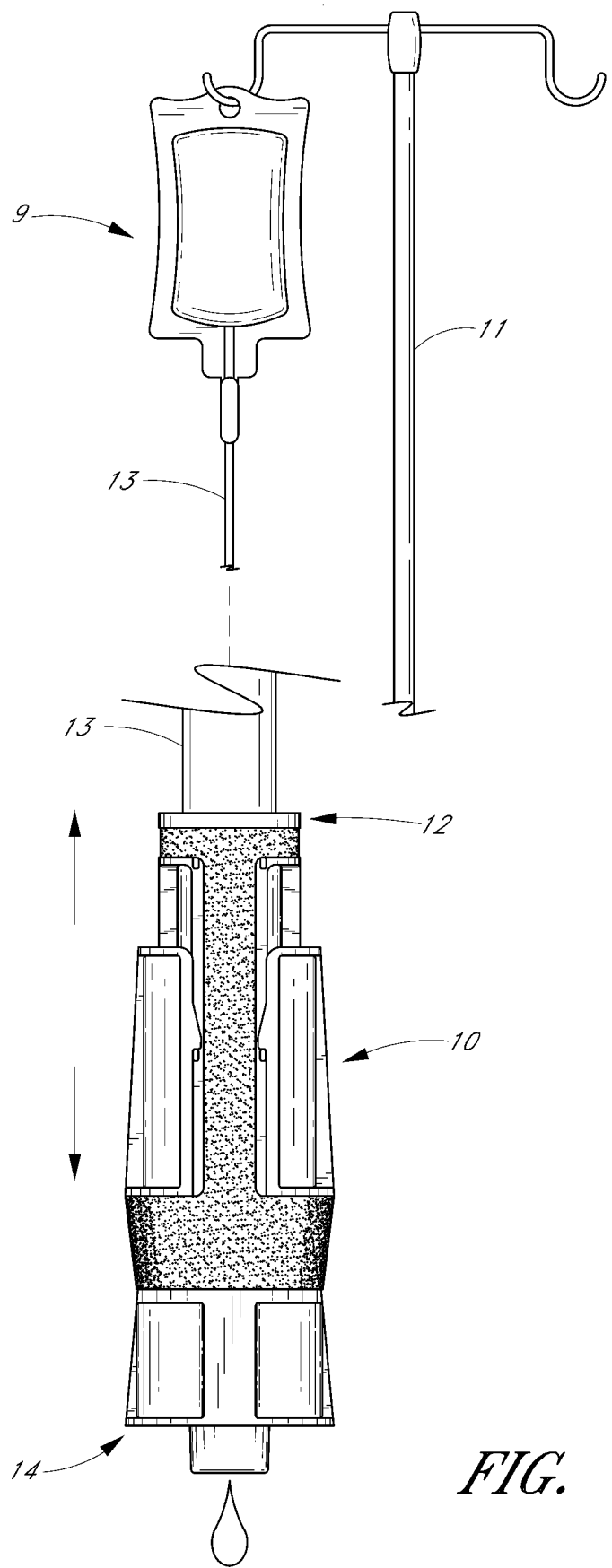
FIG. 1B shows a perspective view of the connector of FIG. 1A in a stretched, substantially opened configuration.

In FIG. 1B, the connector 10 is illustrated in an open position. Fluid can flow out into the first end 12 of the connector 10 and out of the second end 14 of the connector 10. A health care provider can move the male luer connector 10 into this configuration by grasping the second end of the closable male luer 10 with two fingers, grasping the tubing 13 with two other fingers, and gently moving the fingers in opposite directions.

The IV delivery system illustrated in FIGS. 1A and 1B can be easily readied for fluid communication with a patient. In most circumstances, the tubing 13 is filled with air when it is initially connected to the IV bag 9. If the other end of the tubing 13 is connected to a closed connector, as illustrated in FIG. 1A, the air cannot escape and fluid cannot enter the tubing 13 from the IV bag 9. The luer connector 10 is therefore manually moved into the opened position until all of the air has been purged through the luer 10 and the fluid in the IV bag 9 fills the tubing 13 and connector 10. This procedure is known as "priming." As soon as the fluid line and connector are properly primed, the health care provider can quickly release the opposing forces applied to the second end 14 of the luer connector 10 and the tubing 13, and the closing mechanism of the luer connector 10 can rapidly stop the flow of fluid through the luer connector 10.

Figure 1C:
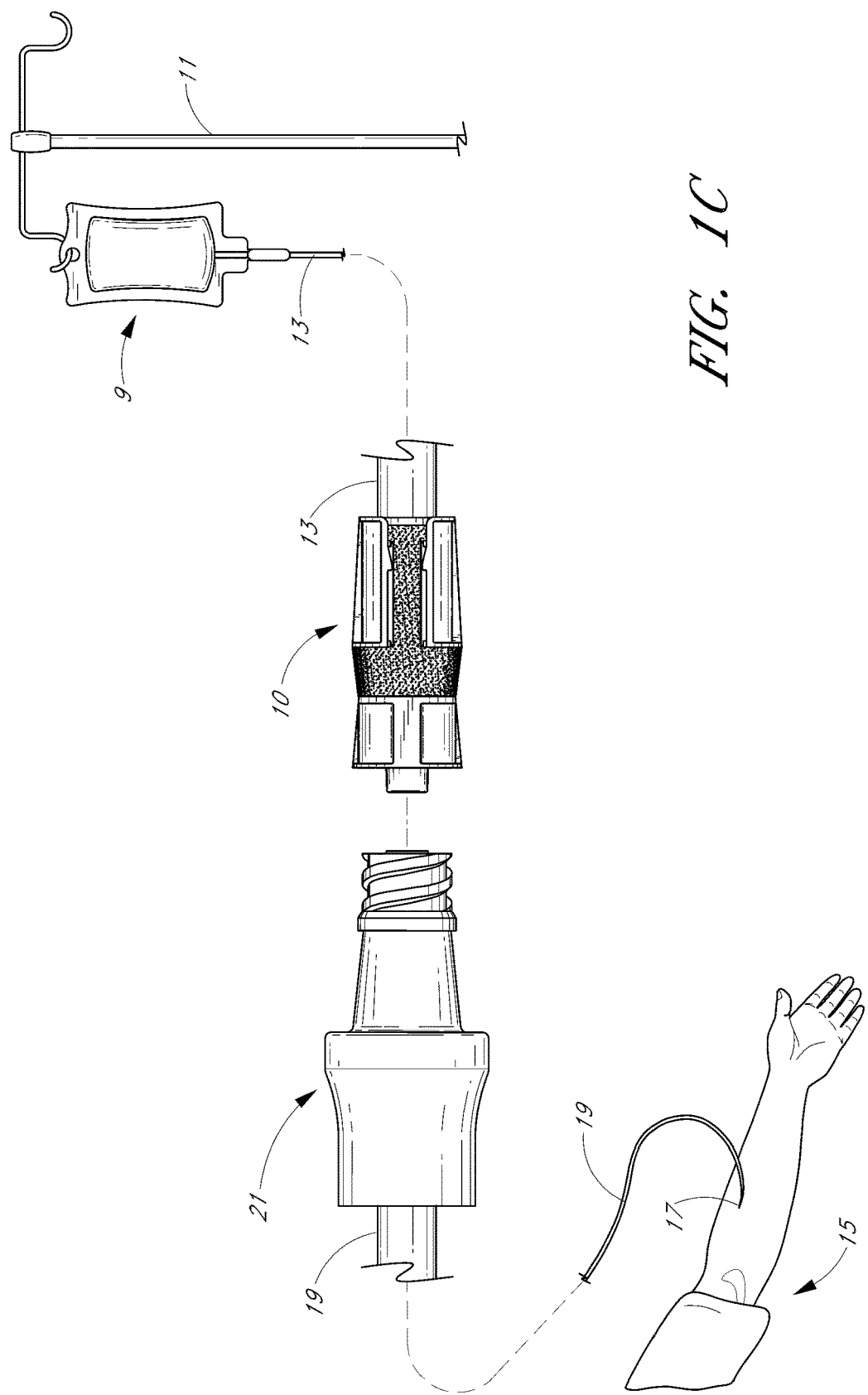
FIG. 1C shows a perspective view of an embodiment of the connector of FIG. 1A being connected to an exemplary female connector attached to tubing inserted into a patient.

Referring now to FIG. 1C, a catheter 17 has been inserted into a patient's arm 15. The catheter 17 penetrates the skin of the arm 15 and is preferably fluidly connected with the patient's bloodstream. The catheter 17 is also connected to a length of medical tubing 19 attached to a female medical connector 21. The example of a female medical connector 21 illustrated in FIG. 1C is a version of the Clave® connector manufactured by ICU Medical, Inc., San Clemente, Calif. Various embodiments of a connector of this type are illustrated and described in U.S. Pat. No. 5,685,866, which is incorporated herein by reference in its entirety. It is contemplated that many of the male luer embodiments disclosed herein can be used with other types of female connectors. The tubing 19, catheter 17, and female connector 21 were previously primed with fluid using standard procedures. The luer connector 10 is primed as described previously and brought into engagement with the female connector 21. As described in further detail below, when the male connector 10 and female connector 21 are engaged, fluid is permitted to flow from the IV bag 9 into the patient. When the male connector 10 and female connector 21 are disengaged, fluid is once again prevented from flowing out of the second end 14 of the male connector 10. In general, fluid is also prevented from flowing out of the opening in the female connector 21.

The embodiment illustrated in FIGS. 1A-1C is described in further detail below. Each of the other embodiments disclosed herein can be used in the illustrated fluid system, and in various modifications and alternatives thereof. Further, it is contemplated that the various embodiments of connectors in accordance with the inventions can be used in a wide variety of additional medical fluid systems. For example, the disclosed connectors can also be used to transfer bodily fluids such as blood, urine, or insulin, nourishing fluids, and/or therapeutic fluids such as fluids used in chemotherapy treatments. The disclosed connectors can also be used to interconnect various other components of fluid transfer systems.

Figure 2:
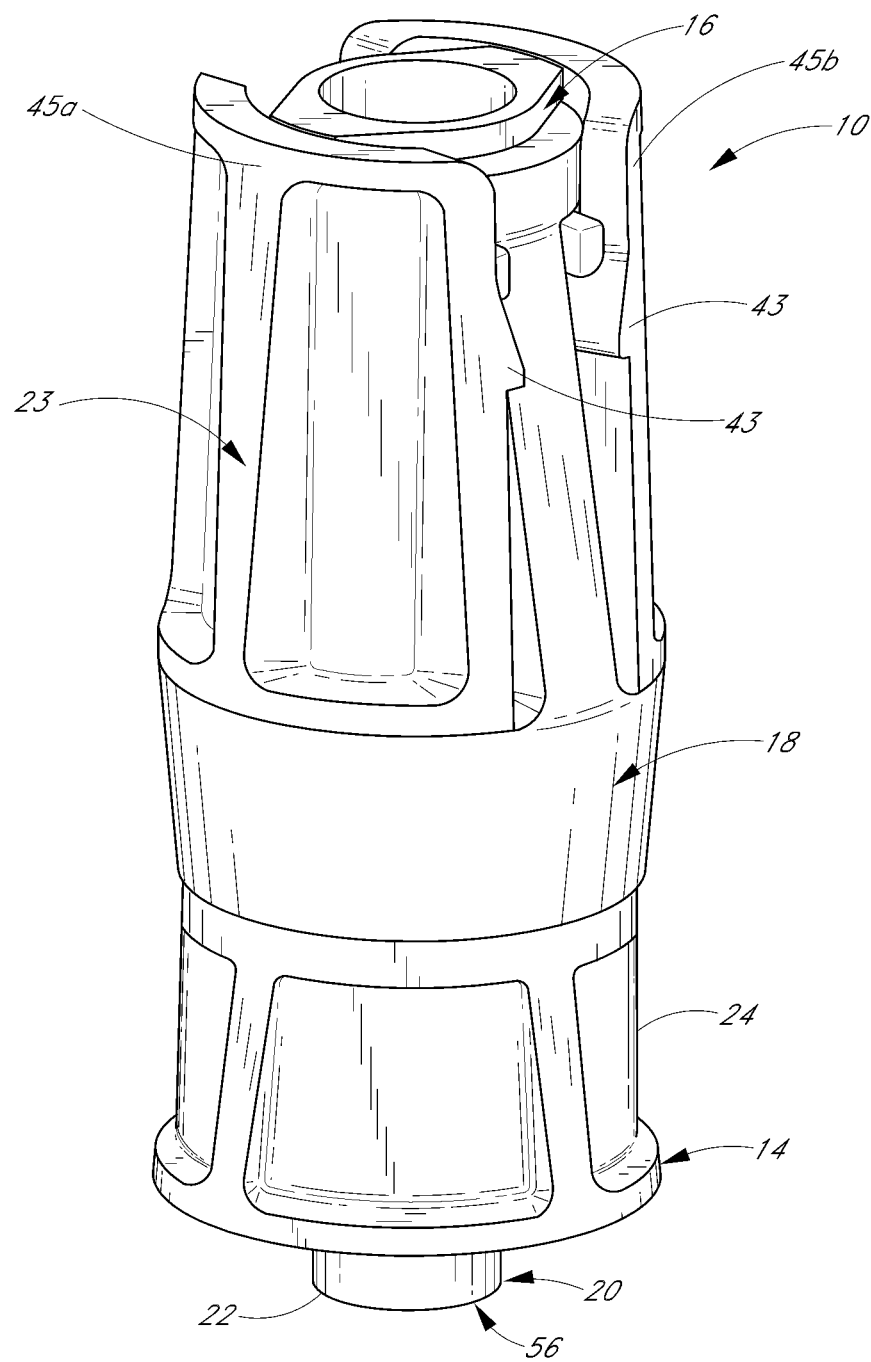
FIG. 2 shows a perspective view of an embodiment of a closeable male luer connector.

Referring now to FIGS. 2-9, the closeable male luer of FIGS. 1A-1C is illustrated in greater detail. As illustrated in FIG. 2, the assembled luer connector 10 comprises four portions: a housing 23, a valve member 16, a resilient member 18, and a sealing ring 20 (not visible in FIG. 2). These portions are individually illustrated in FIGS. 3 through 6, and will be discussed in further detail with reference to these figures. The luer connector 10 can be constructed of more or fewer portions, and such portions can be combined into different configurations.

Figure 3:
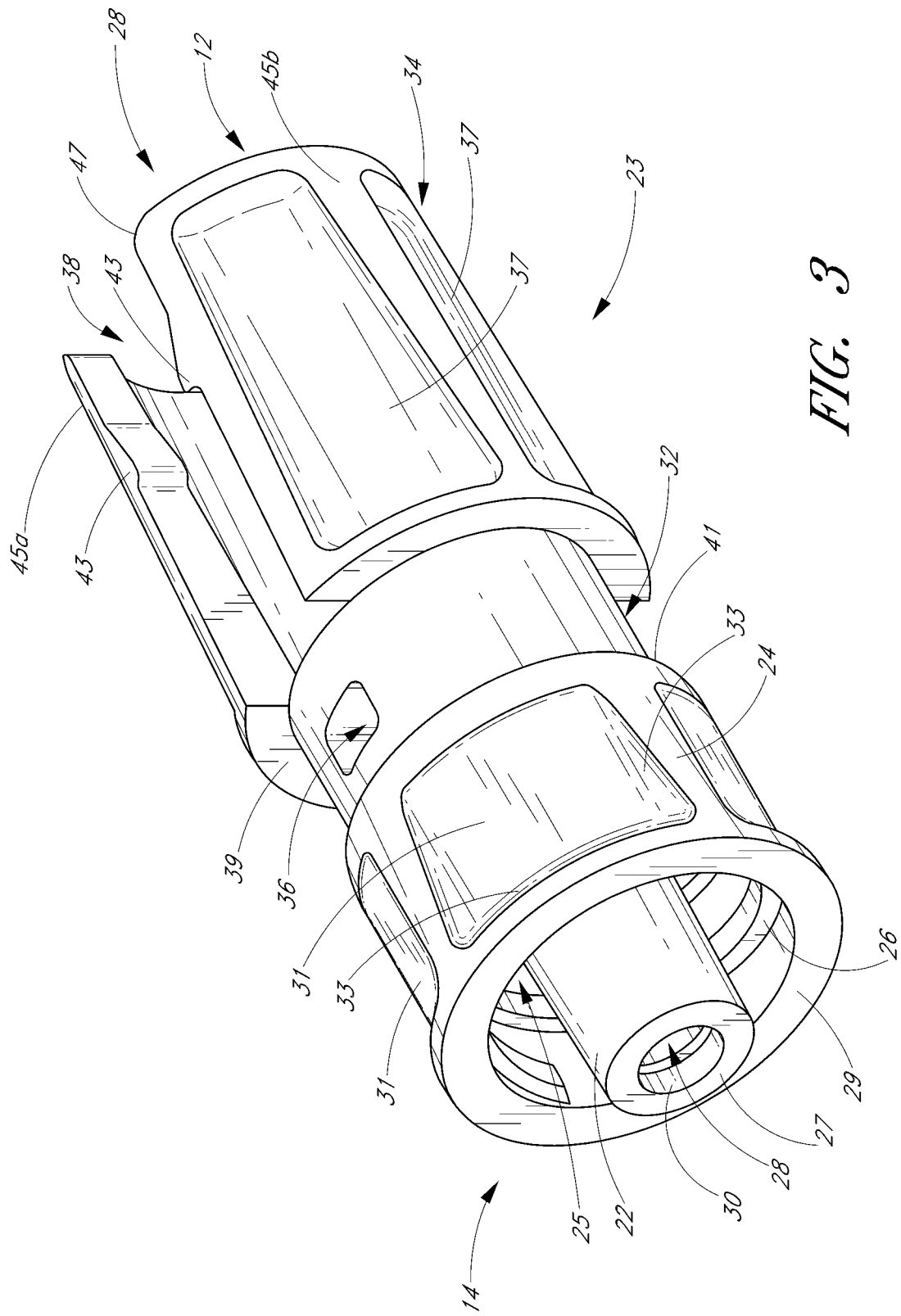
FIG. 3 shows a perspective view of a housing portion of the connector of FIG. 2.

FIG. 3 illustrates the housing 23 of the connector 10, apart from the other portions of the luer connector 10. The housing 23 is generally a tube-like structure with an axial passageway 28 that extends from the first end 12 of the connector 10 through the upper housing 34, and the middle portion 32, and the luer tip 22, to the second end 14 of the housing 23. In some embodiments, the length of the housing 23 from the first end 12 to the luer tip 22 is approximately 11/8 inches. The housing 23 is preferably, but not necessarily, less than or equal to about 11/2 inches from the first end 12 to the second end 14 so that the weight and bulk of the connector are minimized. The housing 23 can have any suitable length for a particular application. The luer tip 22 connects to the remainder of the housing 23 at a base 25 that is surrounded by a shroud 24. The end 27 of the luer tip 22 towards the second end of the luer connector 10 extends some distance beyond the edge 29 of the shroud.

The shroud 24 preferably has inner threads 26 on an interior wall that help securely attached the connector 10 in a removable fashion to another medical implement. In other embodiments, the shroud 24 can include other structures or materials for providing a releasable connection, including quick-release mechanisms and other means. The shroud 24 includes a plurality of depressions 31 on an outer surface to assist the user in firmly grasping and twisting the shroud 24 of the housing 23 with the fingers. The depressions 31 have upwardly tapering sidewalls 33 that prevent the fingers from sliding off the connector 10. On an end towards the first end of the connector 10 of each depression 31, the surface of the housing 23 is approximately co-planar with the surface of the depression 31, while on an end towards the second end 14 of the connector 12 of each depression 31, the surface of the housing 23 is offset from, and preferably lies above, the surface of the depression 31. This configuration allows the fingers to comfortably slide in a direction towards the second end 14 of the connector 10 along the housing 23 into a position for gripping or twisting the connector 10. Once the fingers are in the desired position, a tapered wall 33 on an end towards the second end 14 of the connector 10 of the depression 31 resists further movement by the fingers in the direction of the second end 14. A series of depressions 31 extend around substantially the entire outer surface of the shroud so that the user's fingers, when positioned on opposite sides of the connector 10, will likely encounter a depression 31 regardless of the orientation of the connector 10 during use.

In the illustrated embodiment, the tip 22 has a tapered external wall. The diameter of the tip 22 becomes gradually smaller from the base 25 towards the second end 27. The tip 22 includes a hole at its second end 27. At the base 25 of the luer tip 22, an interior hole 35 (see FIG. 8) leads into a region of the fluid passageway 28 in the middle portion 32 of the luer connector 10. The dimensions of the luer tip can be made to comply with applicable standards and/or regulations, such as the ANSI standards.

The interior wall of the luer tip 22 preferably includes a shelf 30 that extends radially inwardly toward the axis of the fluid passageway 28 surrounded by the luer tip 22, making the fluid passageway 28 narrower at its second end 27 than in the region adjacent to the second end 27. In the illustrated embodiment, the surface of the shelf 30 that faces radially inwardly toward the central axis of the connector 10 is tapered in a manner similar to the taper of the outer surface of the tip 22 (see FIGS. 8 and 9). In this configuration, the inner diameter of the shelf 30 narrows in a direction from the side towards the first end to the side of the shelf 30 towards the second end. As described in further detail below, the shelf 30 in the luer tip 22 helps to block and/or impede fluid flow through the connector 10 when the second end of the valve member 16 abuts against it.

The middle portion 32 of the housing 23 lies between the shroud 24 and the upper housing 34. As illustrated, the middle portion 32 has a smaller outer diameter than either the shroud 24 or upper housing 34. The middle portion 32 also has two generally rectangular openings 36 disposed on opposite sides of the housing 23 from each other. When the connector 10 is assembled, the middle portion 32 is generally covered by a portion of the resilient member 18 (see, e.g., FIG. 2). As a result, the middle portion 32 does not generally come into contact with the fingers during use. Thus, in some embodiments, a grippable surface need not be used for the middle portion 32. The middle portion 32 can therefore have a smaller diameter and smoother surface than either of the other sections of the housing 23.

The upper housing 34 is generally split into two wall sections 45a, 45b by two gaps 38 (only one shown in FIG. 3). The upper housing 34 includes a series of depressions 37 similar in shape and function to the depressions 31 on the shroud 24. The upper housing 34 may also comprise one or more protrusions 43 that extend into the gaps 38. In the assembled configuration, the protrusions 43 help to retain a portion of the resilient member 18 between the gaps 38 in the wall sections 45a, 45b (see FIG. 2). In some embodiments, the protrusions 43 are tapered from a smaller thickness on their ends towards the first end of the connector to a larger thickness on their ends towards the second end of the connector. The tapering of the protrusions 43 helps in the insertion and retention of the portion of the resilient member 18 in a desired position and orientation, while allowing for bending and contortion of the resilient member 18 during use. The protrusions 43 also help prevent the valve member 16 from advancing too far in the direction of the first end as the connector 12 is moved into the opened position by contacting the set of protrusions 44 toward the second end of the valve member 16. The tapering of the protrusions 43 allows the protrusions 44 of the valve member 16 to be advanced towards the second end during assembly into the housing 23 past the protrusions 43 of the housing 23. The corners 47 towards the first end of the connector on each of the wall sections are preferably rounded to prevent snagging, scratching, or other damage or irritation to the fingers or resilient member 18 during use.

As shown in FIG. 3, the exterior surface of the upper housing 34 includes a lower shelf 39 and the exterior surface of the shroud 24 includes a shelf 41 configured to help retain a central portion of the resilient member 18 around the housing 23 in the assembled configuration (see FIG. 2). The shelf 39 of the upper housing 34 is preferably substantially horizontal to discourage any sliding of the resilient member 18 in the direction of the first end of the connector. The shelf 41 of the shroud 24 is preferably tapered (see FIG. 8) to assist in the proper positioning of the resilient member 18 on the housing 23 during manufacturing of the connector 10.

The housing 23 can be constructed from any of a number of different materials. In some embodiments, the housing 23 can be constructed from a relatively rigid material, such as polycarbonate or other polymeric material. The housing 23 and/or valve member 16 of this embodiment, or components of other embodiments, can also be constructed of a hydrophobic material, such as Bayer Makrolon, or any other suitable material.

Figure 4A:
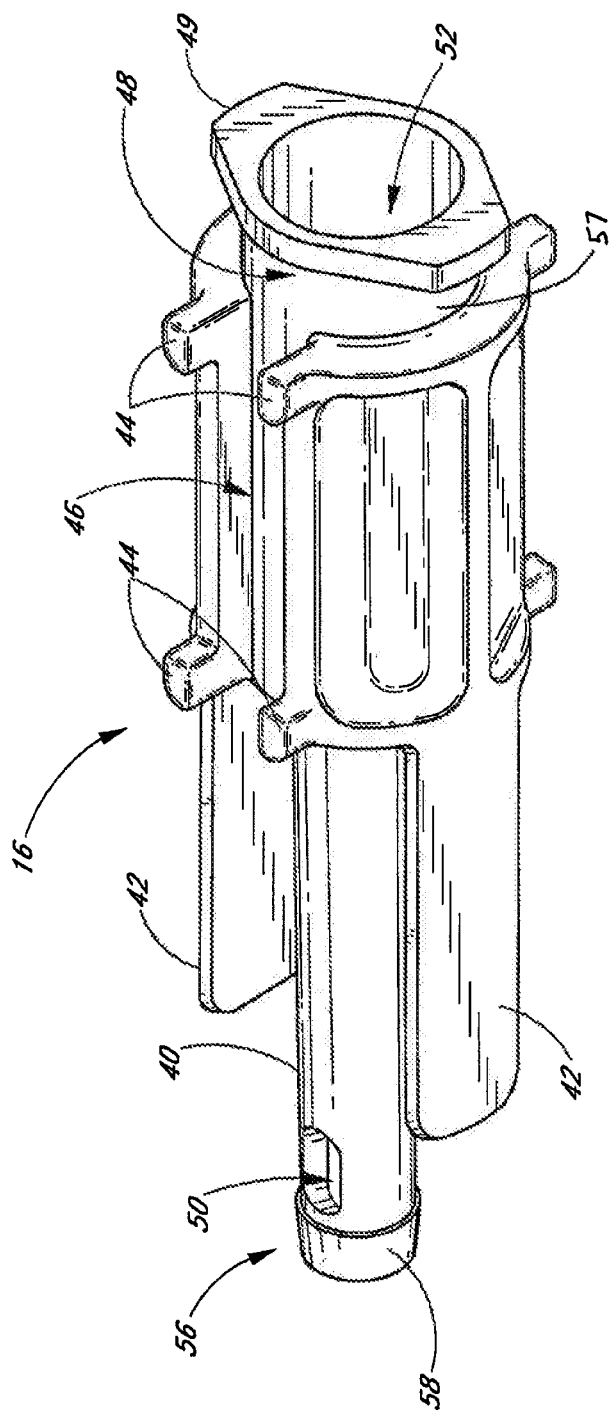
FIG. 4A shows a perspective view of a valve member portion of the connector of FIG. 2.

Referring now to FIG. 4A, the valve member 16 of the male luer 10 is illustrated apart from the other components of the connector 10. In some embodiments, the valve member 16 comprises a fluid passageway 52 of varying diameter extending from the first end 48 of the valve member 16 to the second end 56 thereof, surrounded by additional structures. Near the first end 48, the valve member 16 and corresponding section of the fluid passageway 52 are relatively wide to accommodate a section of standard-diameter medical tubing inserted therein. Near the middle of the valve member 16, a tube 40 surrounding a portion of the fluid passageway 52 is attached to the portion near the first end of the valve member 16. The tube is adjacent to two approximately parallel struts 42 along at least a portion of the tube 40. The tube 40 can have a circular cross-section or other appropriate cross-section. The struts 42 are preferably relatively thin and approximately planar. A first end of each strut 42 connects to the valve member 16 at approximately the middle section of the valve member 16, and a second end of each strut extends toward the second end 56 of the valve member 16. The second end 56 of the valve member 16 preferably extends further than the ends of the struts. There is preferably an open space between the inner wall of each strut 42 and the outer wall of the tube 40.

From near the middle of the valve member 16 to the first end 48 thereof, the fluid passageway 52 comprises a wider region with protrusions 44 along its external surface. Protrusions 44 form two channels 46 (only one is shown in FIG. 4A) lengthwise along opposing sides of the body of the valve member 16. In some embodiments, the struts 42 are spaced circumferentially from the channels 46, as illustrated.

Near the first end of the valve member 16 and tube 40, a circumferential channel 57 may be formed around the perimeter of the body of the valve member 16. Raised tabs 49 can be formed along the edge of the channel 57 toward the first end of the connector, while the raised middle portion of the valve member 16 can form the edge of the channel 57 toward the second end of the connector. In some embodiments, the raised tabs 49 do not extend evenly about the perimeter of the first end of the valve member 16, but instead have two larger sections that are spaced diametrically from each other.

The amount of material necessary to construct the valve member 16 can be reduced by indentations made in the outer layers of this portion. The tube 40 can have a passage 52 disposed therethrough. This passage 52 preferably extends from a hole at the first end of the valve member 16 to a pair of holes 50 (only one shown in FIG. 4A) positioned substantially adjacent to the second end of the valve member 16. In the illustrated embodiment, these holes 50 are generally rectangular in shape. The region of the tube 40 near the second end of the connector can also be formed with only one hole or more than two holes, and other shapes for one or more of the holes can also be employed. For example, the holes 50 can be formed with a tear-drop shape (e.g., narrow on one end and wider on an opposite end), which facilitates an injection molding process of manufacture. Further, in some embodiments, the valve member 16 can be constructed without a fluid path and function as a blocking plunger for fluid flowing around the valve member 16 rather than a means for conveying fluid between the first and second ends of the connector 10.

The tube 40 of the valve member 16 comprises, at its second end, a flange section 58. The flange section 58 preferably extends further in the radial direction than the adjacent portion of the tube 40. In some embodiments, the flange section 58 can be formed of the same or substantially the same material as the rest of the tube 40. The flange section 58 preferably tapers from the first end of the valve member 16 towards the second end of the tube 40. In some embodiments, the taper is formed at a 5-degree angle, and has a substantially identical taper to that of the radially inwardly facing surface of the shelf 30 of the housing 23. Other amounts of taper, or no taper, can also be used.

The valve member 16, like the housing 23 of FIG. 3, may be constructed from a number of different materials. Examples of such materials include polycarbonate or other polymeric materials. The valve member 16 can be approximately the same length or somewhat shorter than the housing 23. For example, the length of the valve member 16 can be approximately 1 inch. In some embodiments, the valve member 16 can be substantially shorter than the length of the housing 23. The valve member 16 can be formed from the same rigid materials as the housing 23. In certain applications, for example, semi-rigid or even more flexible materials may be desirable for use in the valve member 16, and more particularly for the flange section 58 toward the second end of the tube 40.

The valve member 16 can be manufactured through injection molding. In some embodiments, at least two gates are used to facilitate distribution of molten plastic throughout the mold. Preferably, one gate can be located along one of the sides of the valve member 16 between the end of the struts 42 towards the first end of the connector and the raised tabs 49 and another can preferably be located near the holes 50 in the valve member 16. The locations of the gates are not fixed, however, and other locations on the valve member 16 can be used for gates when injection molding the valve member 16. Constructing both the housing 23 and the valve member 16 of this or other embodiments out of the same material lessens the chance of deteriorated performance of the connector 10 due to thermal expansion/contraction or chemical interaction between the connector 10 and its environment.

Although the valve member 16 of the illustrated embodiment is configured as shown in FIG. 4A, many other configurations are possible. In some embodiments, the valve member 16 can be relatively smooth on its external surface, and can principally comprise the tube 40 defining the passage 52. In still other embodiments, different numbers of struts 42 can be disposed along the sides of the valve member 16.

Figure 4B:
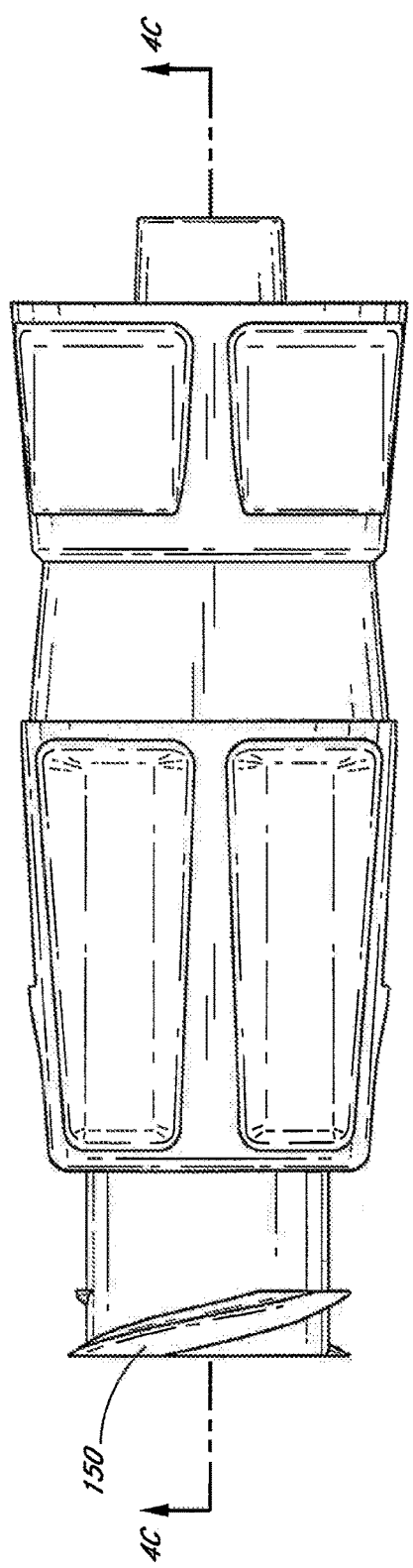
FIG. 4B shows a perspective view of another embodiment of a valve member portion of the connector of FIG. 2.

As can be seen in the embodiment illustrated in FIG. 4B, the raised tabs 150 near the first end of the valve member 16 can also comprise an external engaging surface 150, such as a screw thread, for removably attaching a medical implement (not shown), such as a syringe, with the first end of the valve member 16.

Figure 4C:
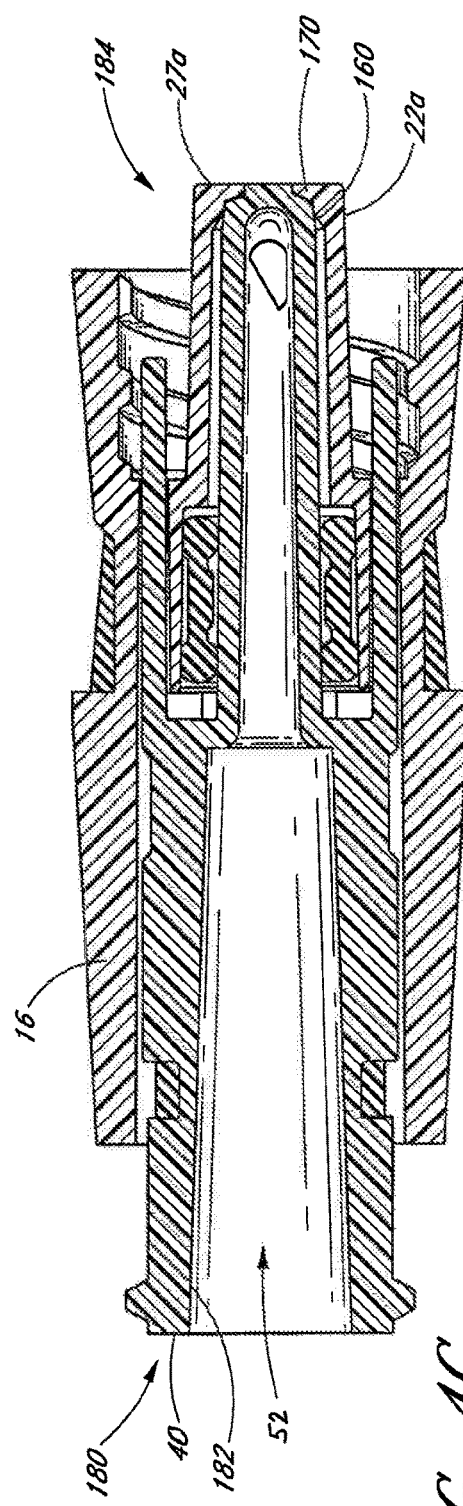
FIG. 4C shows a cross-sectional view of the embodiment of the valve member portion of the connector of FIG. 4B.

In the embodiment illustrated in FIG. 4C, the channel 52 additionally can be tapered along the internal surface 182. The taper of the channel 52 can result in a decrease in width of the channel with a larger size at the first end 180 of the valve member 16 and a smaller size towards the second end 184 of the valve member. The internal taper of the channel 52 can compliment and closely fit with the taper of a male luer. Such an internal taper can conform to ANSI standards and/or regulations, such as the standard for medical syringes. In the illustrated embodiment, the tube 40 of the valve member 16 does not have a flange section 58 that extends radially outwardly beyond the wall of the tube 40, as in the embodiment of FIG. 4A. Instead, the wall of the tube 40 tapers radially inwardly in the region of the second end. The second end 27a of the luer tip 22a can have a smaller cross-sectional second portion 170 which decreases the likelihood of fluid escaping along the internal surface of the second end 27a of the luer tip 22a. Near the second end 27a of the luer tip 22a, a larger cross-sectional region 160 can transition to the smaller cross-sectional portion 170 towards the second end of the connector in many different ways, such as with an abrupt stair-step transition as illustrated in FIG. 4C or with a gradual tapering transition, or other transitions. Some sample cross-sectional diameters of the opening at the second end 27a of the luer 22a include those of about 2 mm or less, including about 0.5 mm, 0.75 mm, 1.0 mm, 1.25 mm, 1.5 mm, and 1.75 mm. The diameters of the opening in the second end 27a can also be in the ranges of 0.4 mm-1.8 mm, 0.5 mm-1.5 mm, and 0.5-1.0 mm. Other diameters, either inside or outside the listed ranges can also be used. Additionally, the second end of the valve member 16 can be sized appropriately to occupy the space in the opening of the second end 27a of the luer 22a.

As shown in FIGS. 4B and 4C, the closeable male luer connector 10 has both a female end 180 and a male luer end 184. The closeable female connector 21 of FIG. 1C (referenced above) and 210 of FIGS. 10 and 11 (described in more detail below), as well as other standard female connectors with similar external structure, also have both female and male ends. In many embodiments, such female connectors utilize seals or other fluid barriers to impede the flow of fluid on the female end but not on the male end. In many of the embodiments of the closeable male luer connectors illustrated herein, there is no seal or other fluid barrier shown on the female end. However, the female end of any of the closeable male luer connectors disclosed herein can be configured to include a closeable female end. For example, the structure for selective fluid-impedence with the female connector 21 or 210, or any of the other standard female connectors, could be included within the female end of any of the closeable male luer connectors disclosed herein to provide a connector that selectively seals or impedes fluid flow on both ends. In some embodiments of this type with closeable female and male ends, it can be advantageous for a resilient seal element to be positioned at or near the female opening, as shown in U.S. Pat. No. 5,685,866. By positioning the seal element in this manner, it is possible to cleanse the female opening prior to use with antiseptic with a wiping motion to avoid a harmful accumulation of debris, bacteria, antiseptic, or other unwanted substances on the seal element and/or in the region between the seal element and the housing of the connector adjacent to the seal element.

Figure 5:
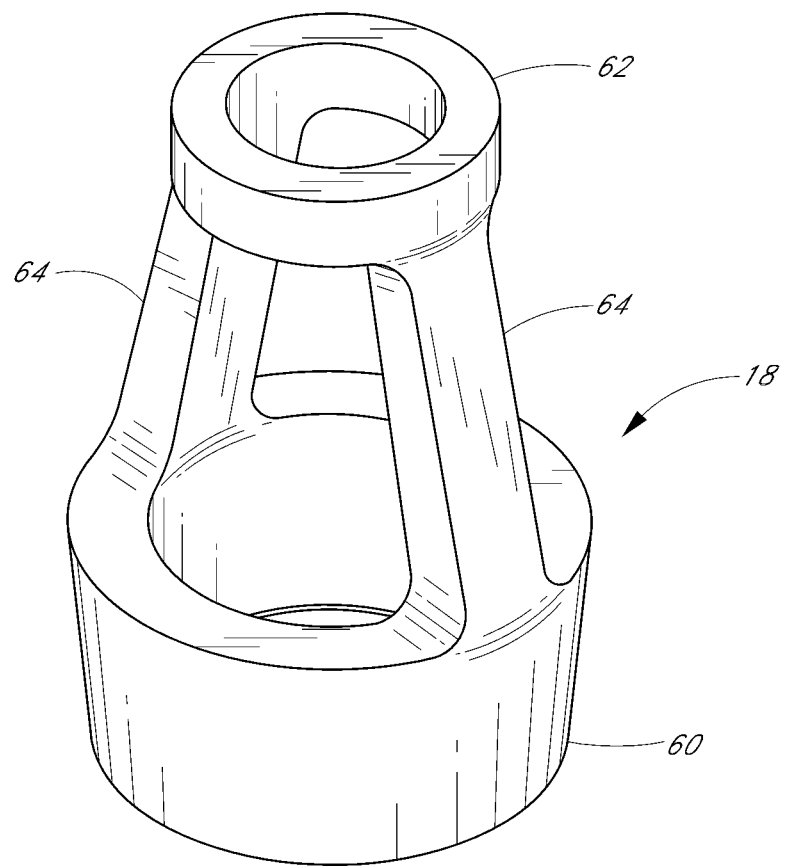
FIG. 5 shows a perspective view of a resilient member of the connector of FIG. 2.

Turning now to FIG. 5, the resilient member 18 is discussed in greater detail. In the illustrated embodiment, the resilient member 18 is formed from two rings 60, 62 separated by two elastic members 64. The rings 60, 62 and/or the elastic members 64 can be made of a deformable material configured to exert a restoring force when stretched. Thus, if the rings 60, 62 are pulled in opposing directions, the elastic members 64 function to restore the rings 60, 62 to their unextended configuration.

The elastic members 64 can be constructed from a number of elastic materials. In some embodiments, the elastic members 64 are made from a silicon rubber elastic material. In other embodiments, the elastic members 64 can be made from a shape-memory material. In still other embodiments, the elastic members 64 and/or the resilient member 18 can comprise springs or other structures capable of exerting a restoring force.

The rings 60, 62 can also be constructed from a number of materials. In some embodiments, the rings 60, 62 are constructed from the same deformable elastic material that comprises the elastic members 64. Thus, the rings 60, 62 can be stretched into a diameter to extend around the appropriate portion of the housing 23 to which each respective ring 60, 62 is attached. The resilience of the rings 60, 62 can function to effectively hold each ring 60, 62 in place on the housing 23. In other embodiments, the rings 60, 62 can be constructed from rigid or semi-rigid materials, and can, for example, comprise half-circles that can be snapped into and out of position. In some embodiments, the resilient member 18 can be integrated into the valve member 16 or housing 23. In some embodiments, other structures and/or configurations can be used to selectively urge the valve member 16 and the housing 23 together in a different manner than a resilient member 18.

Figure 6:
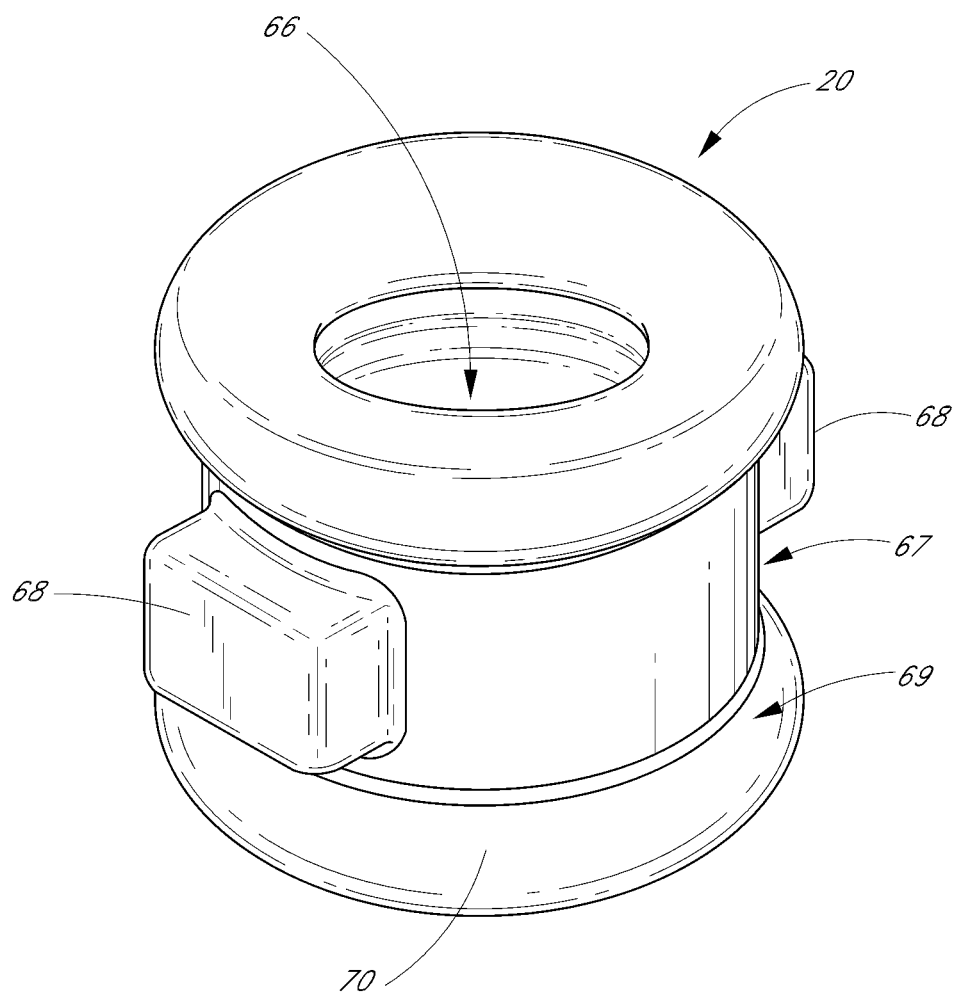
FIG. 6 shows a perspective view of a sealing portion of the connector of FIG. 2. The relative size of the sealing portion is increased in comparison with the components of the connector shown in other figures to facilitate viewing.

Turing now to FIG. 6, the sealing portion 20 is described in greater detail. In some embodiments, the sealing portion 20 is substantially cylindrical and has a bore 66 extending therethrough. In some embodiments, the sealing portion 20 further comprises a pair of generally rectangular protrusions 68 extending from the sidewalls of the cylindrical portion at diametrically opposed positions. The protrusions 68 can have different shapes and/or positions. The sealing portion 20 can also have a generally smaller-diameter middle portion 67 surrounded by two rings 69 at either end with larger diameters.

The sealing portion 20 can be constructed from a number of different materials. In some embodiments, the sealing portion 20 is made from a silicon-based deformable material 70. Silicon-based deformable materials are among those that form fluid-tight closures with plastics and other rigid polymeric materials. The sealing portion 20 can be made from the same material as the resilient member 18.

Figure 7:
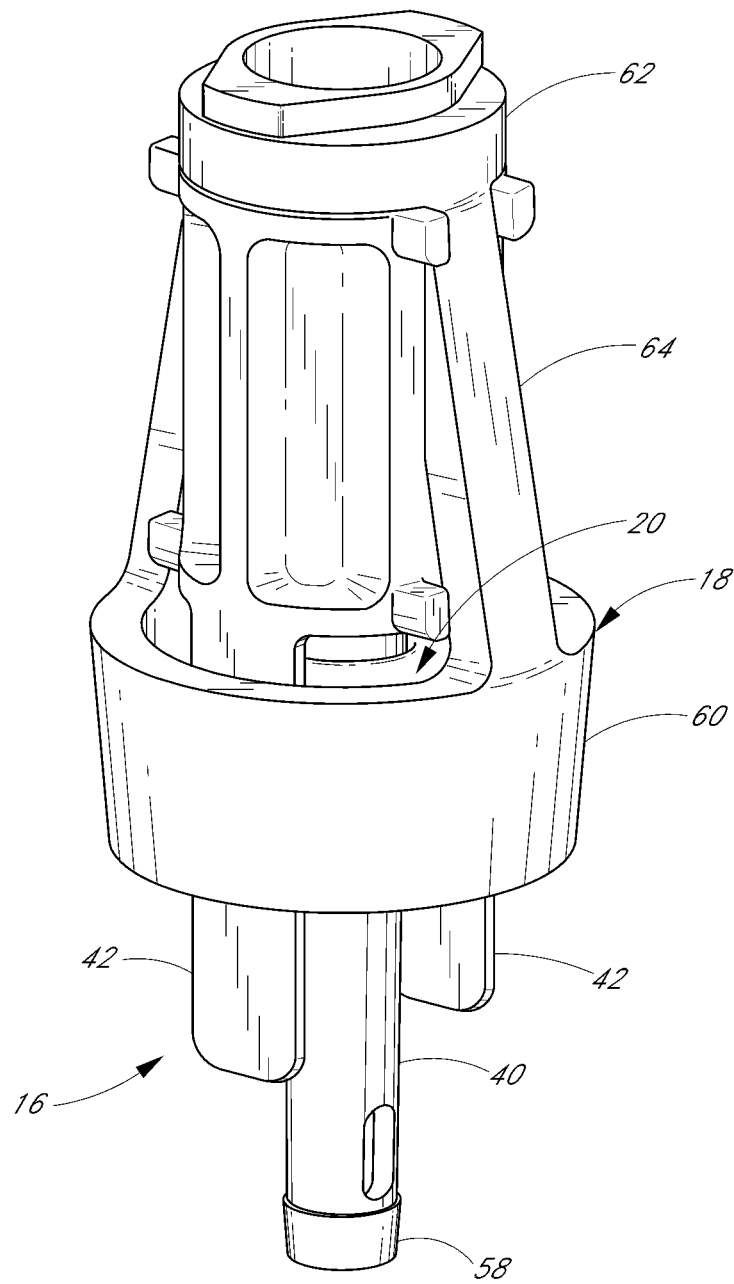
FIG. 7 shows a perspective view of certain components of the connector of FIG. 2 in a partially assembled configuration. The housing portion of FIG. 5 is not shown in FIG. 7.

In FIG. 7, certain components of the male luer 10 of an embodiment are shown. As illustrated, the housing 23 is omitted. The valve member 16, the resilient member 18, and the sealing portion 20 are shown in their respective assembled locations.

Certain interconnections between the various portions of the male luer 10 will now be discussed in further detail. As shown, the smaller ring 62 of the resilient member 18 fits within the circumferential channel 57 of the valve member 16. In some embodiments, the smaller ring 62 can be stretched until it has a larger inner diameter than the raised tabs 49 at the first end of the valve member 16. Once the small ring 62 has been advanced into position about the circular channel 57, it can be released, so that it wraps tightly about the circular channel 57, as shown.

The larger ring 60 of the resilient member 18 extends around the middle portion 32 of the housing 23 (as shown in FIG. 2), and can be stretched and positioned in a manner similar to that described above with respect to the small ring 62. The elastic members 64 of the resilient member 18 can then extend between the small ring 62 and the larger ring 60 of the resilient member 18 and preferably extend along and within the channels 46 in the valve member 16. Once located within these channels, the elastic members 64 are, in effect, trapped by the protrusions 44 along the channel outer walls. As seen in FIG. 2, the elastic members 64 can also extend along the gaps 38 in the upper housing 34 of the housing 23. The gaps 38 are generally located above the channels 46 in the illustrated embodiment. The resilient member 18 thereby provides an elastic connection between the housing 23 and valve member 16, pulling the valve member 16 into engagement with the housing 23.

The sealing portion 20, which is partially hidden by the resilient member 18 in FIG. 7, preferably fits snugly around the tube 40 and lies in between the struts 42 of the valve member 16.

Figure 8:
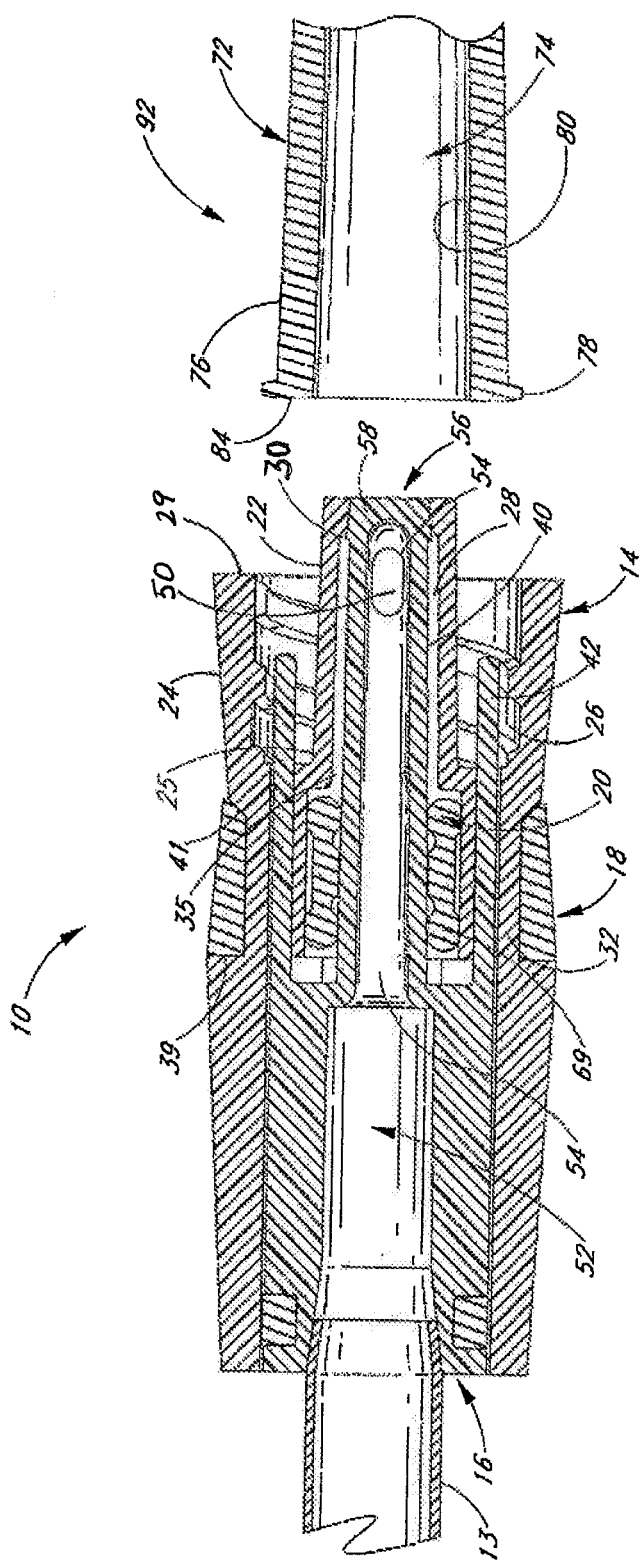
FIG. 8 shows a cross-sectional view of the connector of FIG. 2 adjacent a female portion of another medical implement. At this stage, fluid is impeded through the connector of FIG. 2.

FIG. 8 illustrates a cross-section of the male luer of the present embodiment adjacent an exemplary female connector 92. In this cross-sectional view, the interconnections and interactions between the housing 23, valve member 16 and sealing portion 20 can be seen in greater detail. The valve member 16 is configured to be positioned within the housing 23. As illustrated, the tube 40 of the valve member 16 can be inserted into and through the lumen 28. Meanwhile, the struts 42 are configured to pass through corresponding slots that extend lengthwise through the middle portion 32 of the housing 23. In an assembled configuration, the struts 42 are adjacent to the tip 22 along two sides, and the tube 40 is at least partially contained within the tip 22. The protrusions 44 are captured within the gaps 38 formed in the upper housing 34 of the housing 23.

A closing mechanism 56 is adapted to close the fluid passage extending through the closable male luer 10 from fluid communication with the external environment, preferably whenever the male luer 10 is not engaged with the female connector 92. In the illustrated embodiment, the fluid passageway 54 comprises the lumen 28 as well as the passage 52 of the valve member 16. The closing mechanism 56 of the illustrated embodiment comprises both the flange section 58 of the tube 40 and the internal taper of the raised portion 30 of the lumen 28. As these two surfaces contact, they can form a closure at or near the second end 20 of the male luer 10.

The substantially matched internal tapering surfaces of the raised portion 58 of the tube 40 and the raised portion 30 of the lumen 28 assist in providing closure of the female connector 92. Preferably a relatively fluid-tight closure is formed. The engagement between the raised portions 30 and 58 can also be created in a number of other ways. In some embodiments, the material of the flange section 58 and the material of the raised portion 30 of the lumen 28 are configured to fit closely together, and are made of sufficiently compatible materials, to form a fluid-tight closure. In other embodiments, the flange section 58, and/or additional portions of the valve member 16, can be constructed from a deformable material that more closely follows the contours of the internal surface of the lumen 28, and the lumen 28 need not have a taper. The sealing portion 20 is configured, in some embodiments, to prevent fluid from escaping from within the male luer connector 10. When the valve member 16 engages the housing 23, the sealing portion 20 sits between the middle portion 32 of the housing 23 and the tube 40. When fluid flows within the lumen 28 of the housing 23 and along the outer surface of the tube 40, the fluid is prevented from flowing past the middle portion 32 by the sealing portion 20, and more particularly by the rings 69 at either end of the sealing portion 20.

The sealing portion 20 is preferably held in position between the housing 23 and valve member 16 by the protrusions 68 (see FIG. 6) configured to fit within the holes 36 in the middle portion 32 of the housing 23. The protrusions 68 help to maintain the sealing portion 20 in proper alignment.

With reference to the embodiment illustrated in FIG. 8, the structure of an exemplary female connector 92 will now be discussed in further detail. The female connector 92 can comprise an elongate body 72 having a fluid passageway 74 therethrough, and the female connector 92 can have a tip 76 near its distal end. In some embodiments, the tip 76 of the female connector 92 has a radially extending surface 78 disposed on its external surface. The female connector 92 can have a fluid conduit positioned within the female connector 92. The fluid conduit is not included or required in all female connectors compatible with the connectors 10 disclosed herein. Along a proximal inner surface 80 of the female connector 92, the fluid passageway 74 is preferably tapered such that the diameter of the fluid passageway 74 decreases in the distal direction.

As shown in FIG. 8, the housing 23, the valve member 16, the resilient member 18, and the sealing portion 20 are in an assembled configuration, in which the closing mechanism 56 forms a closing engagement between the flange section 58 and the interior of the lumen 28. In addition, the sealing portion 20 is in closing engagement between the valve member 16 and the housing 23. Fluid from the passage 52 can flow through the windows 50 of the tube 40 of the valve member 16. In this position, the windows 50 communicate with the interior of the tip 22, but not yet with the external environment. The lumen 28 is closed at its second end by the closing mechanism 56 and at its first end by the sealing portion 20.

As shown in FIG. 8, the struts 42 of the valve member 16 extend through slots in the housing 23 such that their ends extend to positions near the end of the shroud 24 toward the second end of the connector. These struts 42 are configured to engage the proximal ends 84 of the female connector 92 as the female connector 92 advances into engagement with the closable male luer 10.

In FIG. 8, the male and female luers are shown in an unengaged configuration. To engage the male luer 10 and female connector 92, the radially extending surface 78 of the female connector 92 are screwed into the inner threads 26 of the male luer 10.

Figure 9:
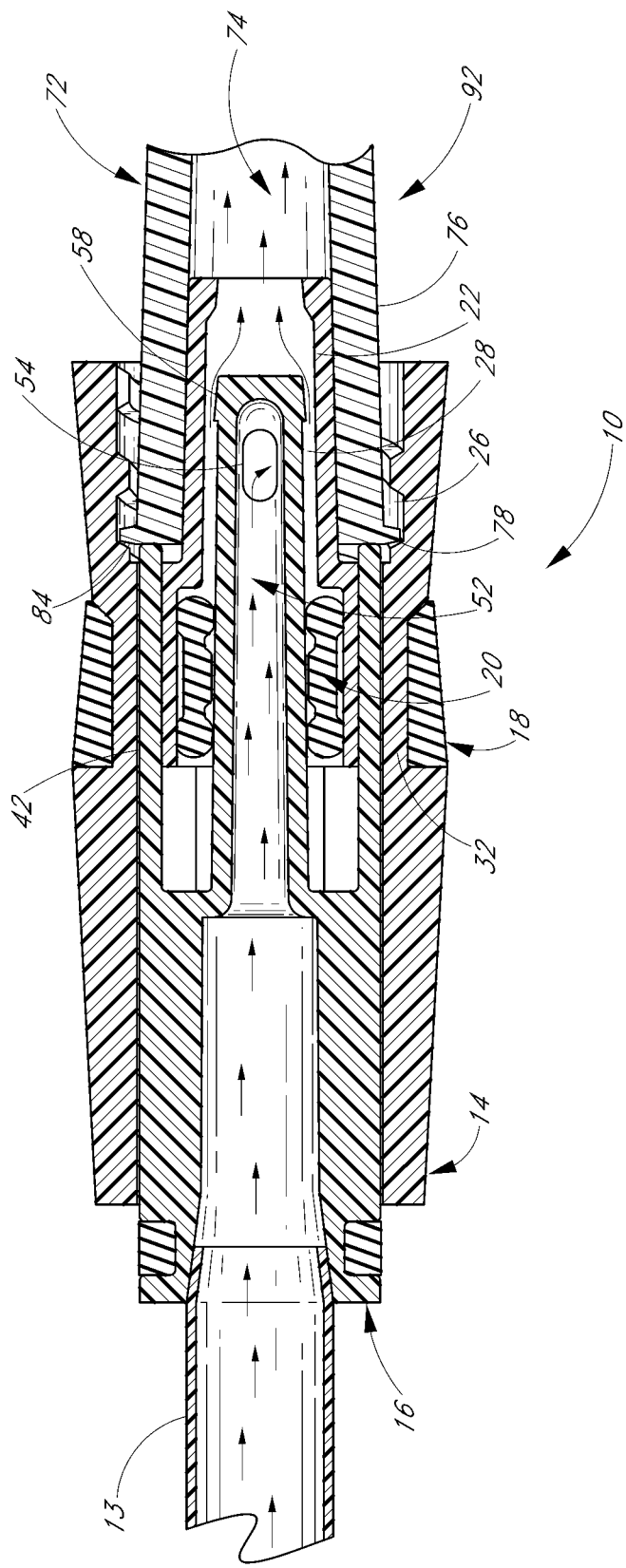
FIG. 9 shows a cross-sectional view of the connector of FIG. 2 in engagement with the medical implement of FIG. 8. Fluid is flowing through the engaged connectors.

As shown in FIG. 9, the two luers can be threadedly engaged towards one another until the taper of the inner surface 80 of the female connector 92 lies adjacent the correspondingly tapered external surface of the tip 22. In other embodiments, the two luers can be threadedly engaged until the second end of the tip 22 forms a closure with a corresponding surface (not shown) of the female connector 92.

As the male luer connector 10 and female connector 92 move towards each other into threaded engagement, the proximal end 84 of the tip of the female connector 92 contacts the struts 42 of the valve member 16. As the male luer connector 10 and female connector 92 move further into threaded engagement, the struts 42, and thereby the valve member 16, are moved in the direction of the first end of the male connector by the female connector 92, displacing the valve member 16 relative to the housing 23. Thus, the flange section 58 moves from the second end of the tip 22 of the housing 23 towards the first end of the male connector. As these two tapered surfaces separate, a space forms between the valve member 16 and the housing 23 and fluid is allowed to pass through the hole 30' into the fluid passageway 74 of the female connector 92, or vice versa. When used with some embodiments of the female connector 92, an internal fluid conduit contacts the second end of the valve member 16 before the housing of the female connector 92 contacts the struts 42 to open the male connector 10. In some embodiments, the closure remains intact until the inner surface 80 of the tip of the female connector 92 has formed a closing engagement with the outer surface of the tip 22 of the male luer 10. Thus, the passage 54 of the male luer 10 need not be in fluid communication with the external environment.

As the valve member 16 moves relative to the housing 23, the elastic members 64 (not shown in FIG. 9) of the resilient member 18 distend and exert a restoring force. As long as the female connector 92 engages the male luer 10, this restoring force can be resisted by the radially extending surface 78 of the female connector 92 contacting the inner threads 26 of the housing 23. However, when the female connector 92 is withdrawn from the male luer 10, the resilient member 18 returns the valve element of the valve member 16 to closing engagement with the lumen 28.

Despite the relative movement between the housing 23 and the valve member 16, the sealing portion 20 preferably maintains a fluid barrier between the outer surface of the tube 40 and the inner surface of the lumen 28. In some embodiments, the position of the sealing portion 20 is maintained by the protrusions 68. In other embodiments, the sealing portion 20 can be positioned by gluing the outer surface of the deformable material 70 to the inner surface of the lumen 28 of the housing 23. Other means of fixing the sealing portion 20 can also be used.

As shown in FIG. 9, in the opened configuration, the fluid passageway 74 of the female connector 92 can fluidly communicate with the passage 52 of the valve member 16. Fluid can thereby flow from tubing 13 attached to the male luer 10, into the passage 52 of the valve member 16, through the windows 50 into the lumen 28, out from the lumen 28 through the hole 30' at the second end of the tip 22 into the fluid passageway 74 of the female connector 92, and vice versa. Fluid is prevented from escaping the male luer 10 through the gap between the housing 23 and valve member 16 by the sealing portion 20. A fluid-tight closure can also be formed between corresponding tapers of the tip 22 of the housing 23 and the inner surface 80 of the female connector 92.

Figure 10:
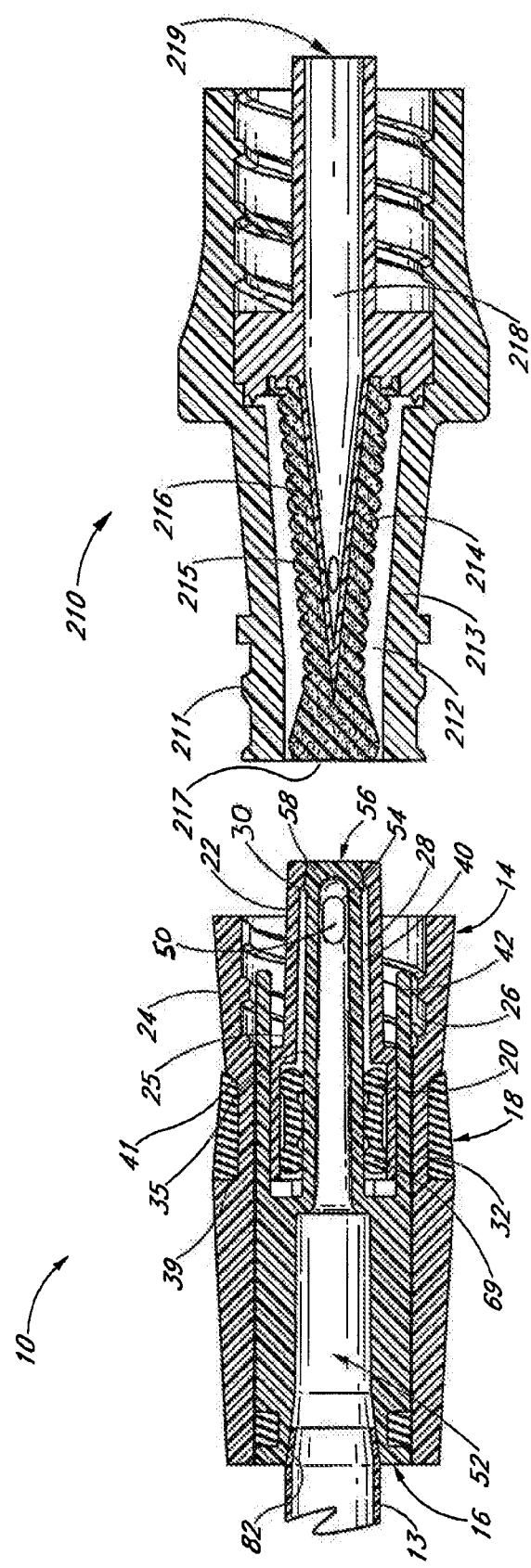
FIG. 10 shows a cross-sectional view of the connector of FIG. 2 adjacent another medical implement with a closeable female luer connector. At this stage, fluid is impeded through the connector of FIG. 2 and the female luer connector.

Turning to FIG. 10, the connector 10 is displayed adjacent to a closeable female luer connector 210. In the sample embodiment illustrated here, the closeable female luer connector 210 comprises an outer housing 213, a void space 212, a fluid passageway 218, a fluid conduit 216 with one or more holes 215, a compressible seal element 214 with a proximal surface 217, and a threaded engagement region 211. The closeable female connector 210 is positioned with its proximal end adjacent the second end 56 of the male connector 10. The threaded engagement region 211 of the closeable female connector 210 can conform to standard sizing for luer connectors, such as those that meet ANSI standards. The compressible seal element 214 can be composed of water-impermeable, resilient material which can reduce in size when a force is exerted upon it. The fluid conduit 216 can be composed of a rigid material, such as polycarbonate plastic, which is capable of resisting deformation when a force sufficient to compress the seal element 214 is exerted upon the closeable female connector 210. The fluid passageway 218 can place the fluid conduit 216 in fluid communication with the second end 219 of the closeable female connector 210. At least one hole 215 in the fluid conduit 216 can be sealed by the compressible seal element 214 to prevent the fluid passageway 218 from being in fluid communication with the void space 212 between the compressible seal element 214 and the inner wall of the housing 213 and/or with the exterior of the housing 213. The hole or holes 215 can be sized appropriately small enough to permit fluid to pass between the fluid passageway 218 and the void space 212 at an appropriate flow rate. One such size for the hole or holes 215 is approximately one millimeter in diameter, although irregular shapes and other sizes can be used. Holes of at least about 1 mm or approximately 1 mm-3 mm, or less than about 1 mm can also be used. The connector 10 can be engaged with a tubing 13 containing a fluid.

Figure 11:
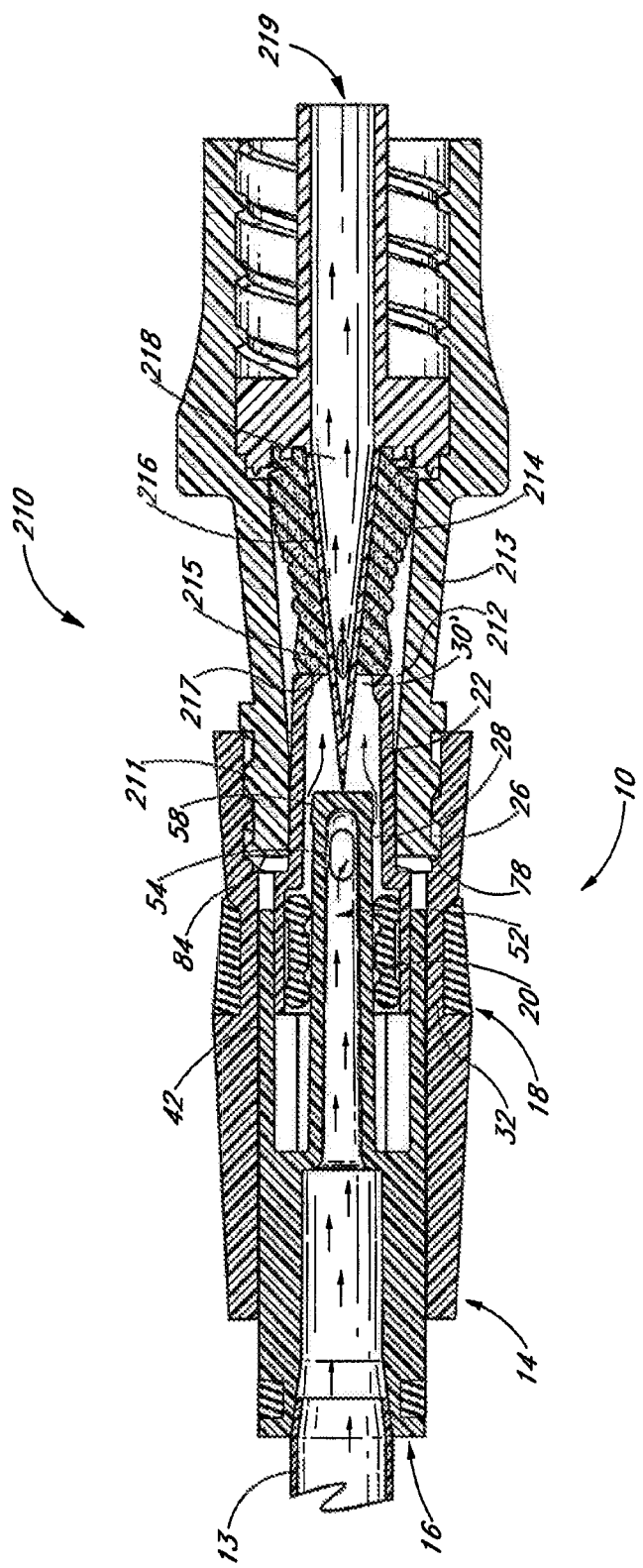
FIG. 11 shows a cross-sectional view of the connectors of FIG. 10 after engagement. Fluid is flowing through the engaged connectors.

With reference to FIG. 11, the connector 10 can be threadedly engaged with the closeable female connector 210. The threaded region 211 of the closeable female connector 210 can engage with the inner threads 26 of the male connector 10 to engage the connectors 10, 210, as illustrated. In the illustrated engagement, the luer tip 22 advances into the closeable female connector 210 by compressing the compressible seal element 214. As can be seen, the luer tip 22 contacts the compressible seal element 214 on the proximal surface 217 of the compressible seal element 214. The force exerted to engage the connectors 10, 210 and engage the threaded regions 26, 211 is sufficient to compress the seal element 214 to expose the holes 215 in the fluid conduit 216. With the seal element 214 compressed, the fluid passageway 218 is in fluid communication with the interior space of the luer tip 22.

As the luer tip 22 advances further into the closeable female connector 210, the fluid conduit 216 contacts the end of the valve member 16 towards the second end of the male connector. The valve member 16 is displaced towards the first end of the male connector by the contact and continued advancement of the luer tip 22. The resilient member 18 exerts a closing force in a direction towards the second end of the male connector on the valve member 16. As a result, the tip of the valve member 16 towards the second end of the male connector generally maintains contact with the fluid conduit 216 throughout the engagement. As the valve member is moved in a direction towards the first end of the male connector, the flange section 58 of the valve member 16 separates from the interior surface of the housing 23 through which the hole 30' passes. As a result, the windows 50 are opened to fluid communication with the closeable female connector 210. The compressed seal element 214 inhibits fluid flow into the interior of the closeable female connector 210 beyond the luer tip 22. In this configuration, fluid can flow from the tubing 13 at the end of the valve member 16 toward the second end of the male connector and into the tube 40 through the windows 50 into the interior of the lumen 28, out the hole 30' in the luer tip 22, into the interior of the outer housing 213 of the closeable female connector 210, in the holes 215 of the fluid conduit 216 and into the fluid channel 217 in the interior of the fluid conduit 216. Thus, the second end of the connector 210 is placed in fluid communication with the proximal end 219 of the closeable female connector 210. Additionally, the sealing portion 20 preferably maintains a fluid barrier between the outer surface of the tube 40 and the inner surface of the lumen 28, confining the flow of fluid towards the closeable female connector 210. When the surface of the valve member towards the second end of the connector is directly contacted by a female connector member such as the fluid conduit 216, the struts 42 may not be engaged by the female connector.

The connectors 10, 210 can be threadedly disengaged. During engagement, the force exerted by the resilient member 18 can return the connector 10 to its pre-engaged state by directing the valve member 16 to engage the flange section 58 of the end of the valve member 16 toward the second end of the male connector with the internal surface of the luer tip 22. Likewise, the resilient material of which the compressible seal is composed can return to its shape in the closed position and the proximal surface 217 can seal the proximal tip of the closeable female connector 210.

Figure 12:
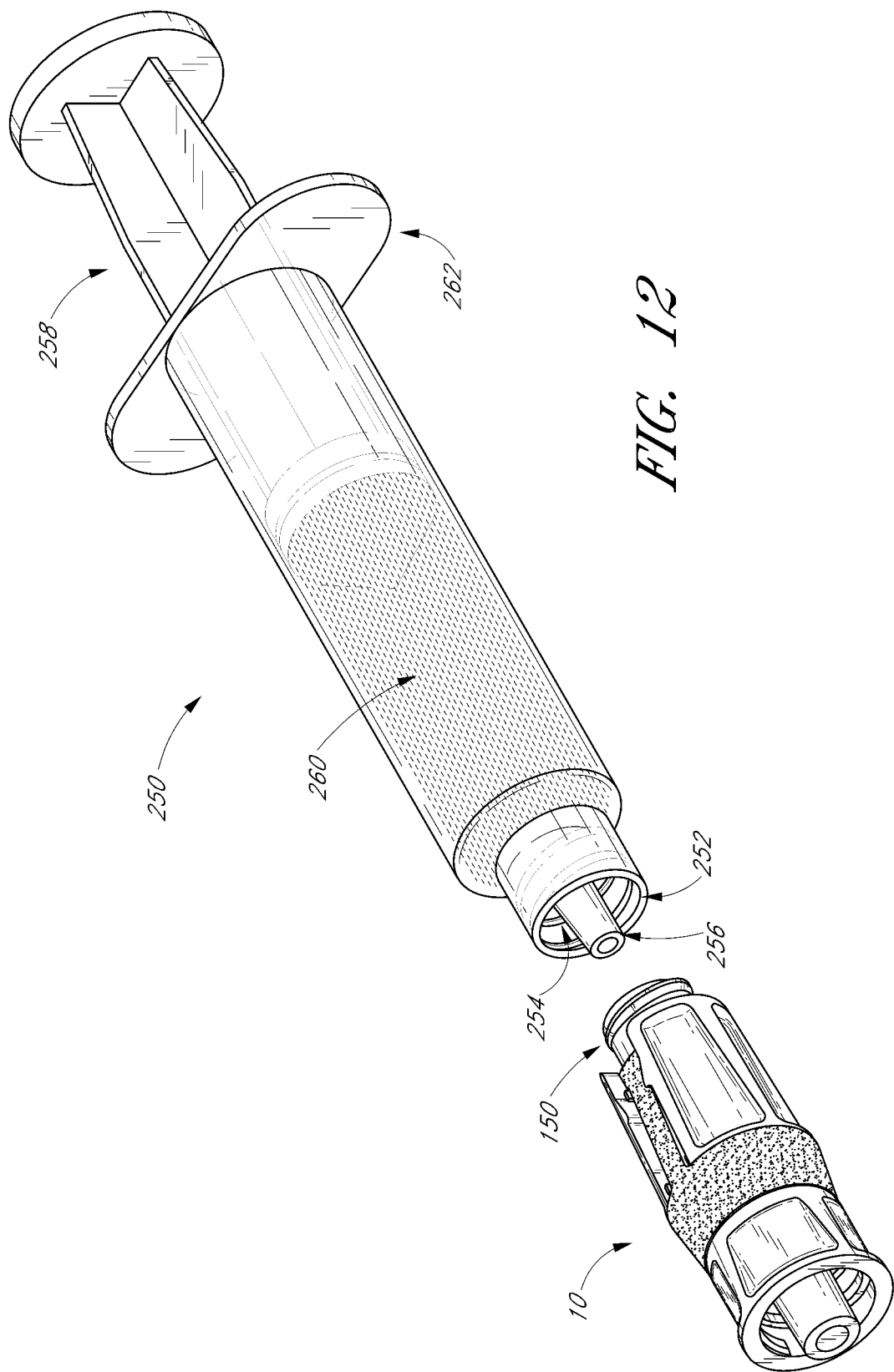
FIG. 12 shows a perspective of the connector of FIG. 2 adjacent a syringe with a male luer tip. At this stage, fluid is impeded through the connector.

Referring now to FIG. 12, the connector 10 can be engaged with a syringe 250. In FIG. 12, the syringe 250 and connector 10 are displayed adjacent to each other. The syringe can comprise a male luer connector 252, a plunger 258, a reservoir 260, and convenient finger anchors 262. The luer connector 252 can further comprise an internally threaded shroud 254 and a syringe luer tip 256. In the illustrated embodiment of the connector 10, a threaded surface 150 is disposed on the outside surface of the first end of the valve member 16.

Figure 13:
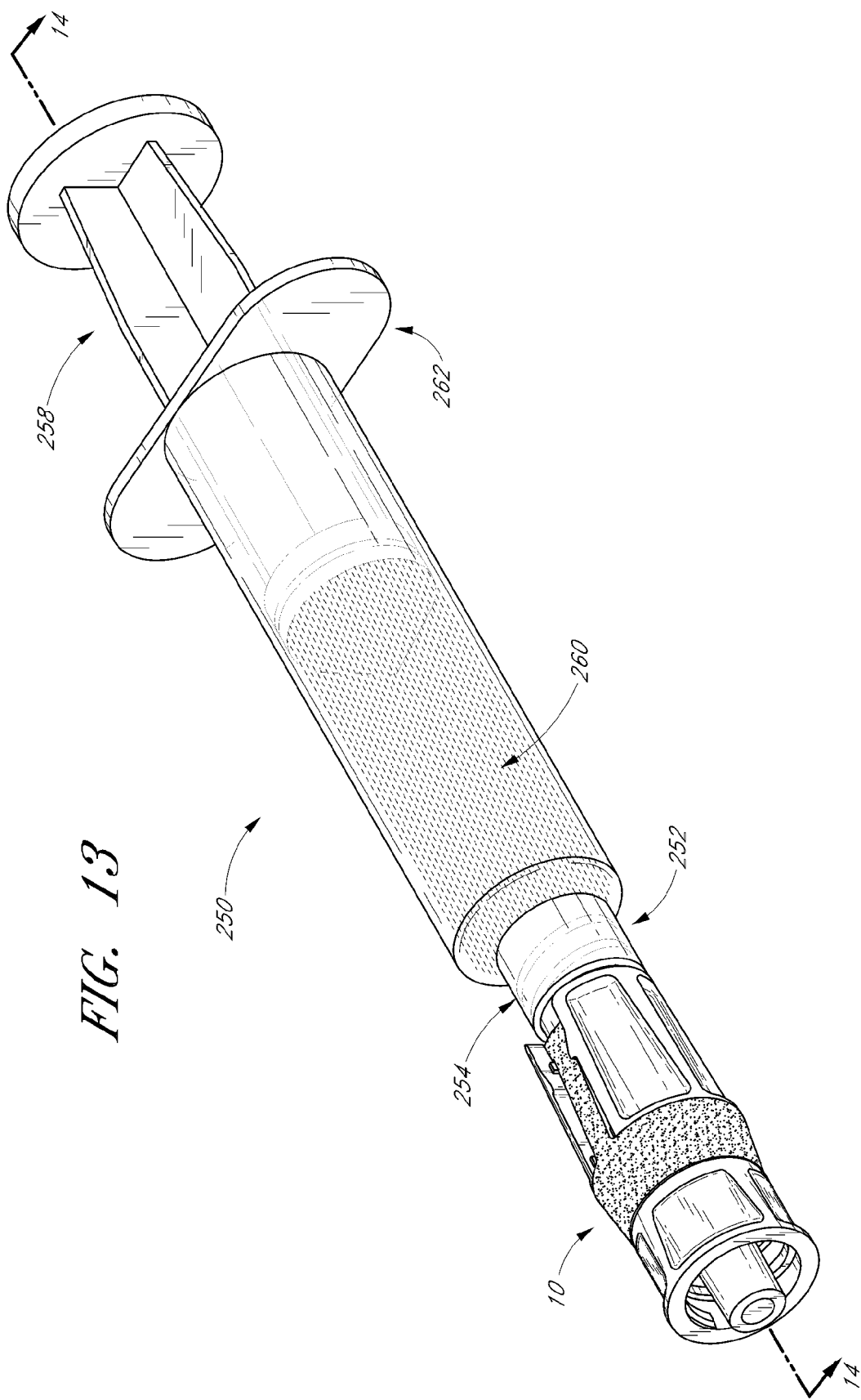
FIG. 13 shows a perspective view of the components of FIG. 12 after engagement. At this stage, fluid is still impeded through the connector.

With reference now to FIG. 13, the connector 10 can be threadedly engaged with the syringe 250. The shroud 254 can engage with the end 16 of the valve member toward the first end of the connector to connect the connector 10 to the syringe 250. The reservoir 260 of the syringe 250 can be placed in fluid communication with the tube 40 interior to the valve member 16.

Figure 14:
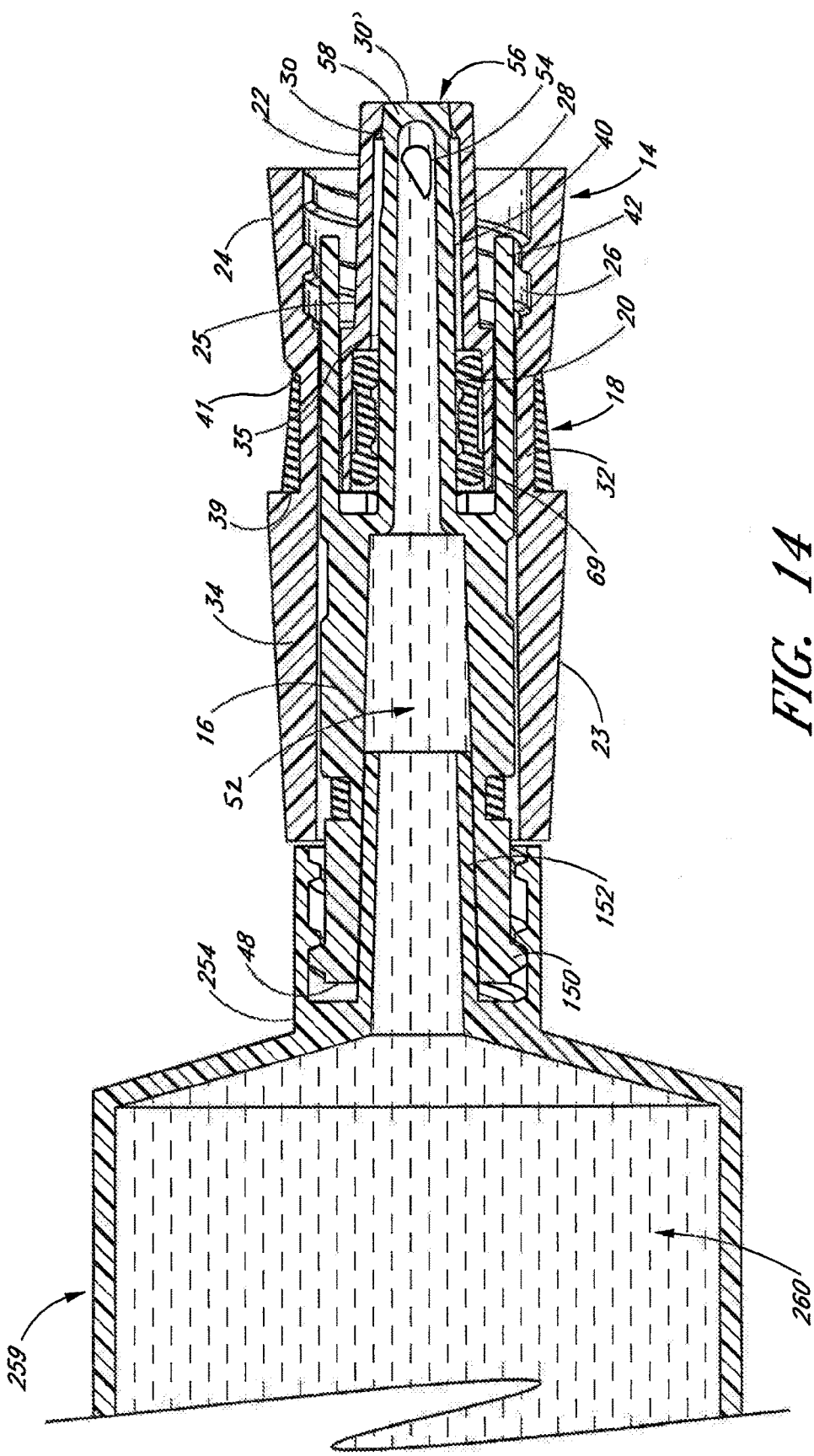
FIG. 14 shows a cross-sectional view of the connector and the male luer tip of the syringe of FIG. 13.

Turning to FIG. 14, the engagement illustrated in FIG. 13 is shown in a cross-sectional view. The syringe 250 is threadedly engaged with the connector 10 by the engagement between the shroud 254 and the threaded surface 150 of the valve member 16. The luer tip 252 of the syringe 250 is extended into the tube 40 of the valve member 16. The reservoir 260 of the syringe, shown here with a fluid in the reservoir 260, is in fluid communication with the interior of the valve member 16. The fluid can pass through the tube 40 and towards the luer tip 22 of the connector 10. In the illustrated embodiment, the fluid cannot exit the connector 10 out its male luer tip 22 because the flange section 58 is in contact with the interior surface of the lumen 28. Accordingly, the hole 30' in the tip of the housing 23 towards the second end of the connector is blocked by the valve member 16. In order for the syringe 250 and connector 10 to transition from the stage shown in FIG. 12 to the stage shown in FIG. 14, the valve member 16 may need to be temporarily opened to release air (as described in more detail below).

Figure 15:
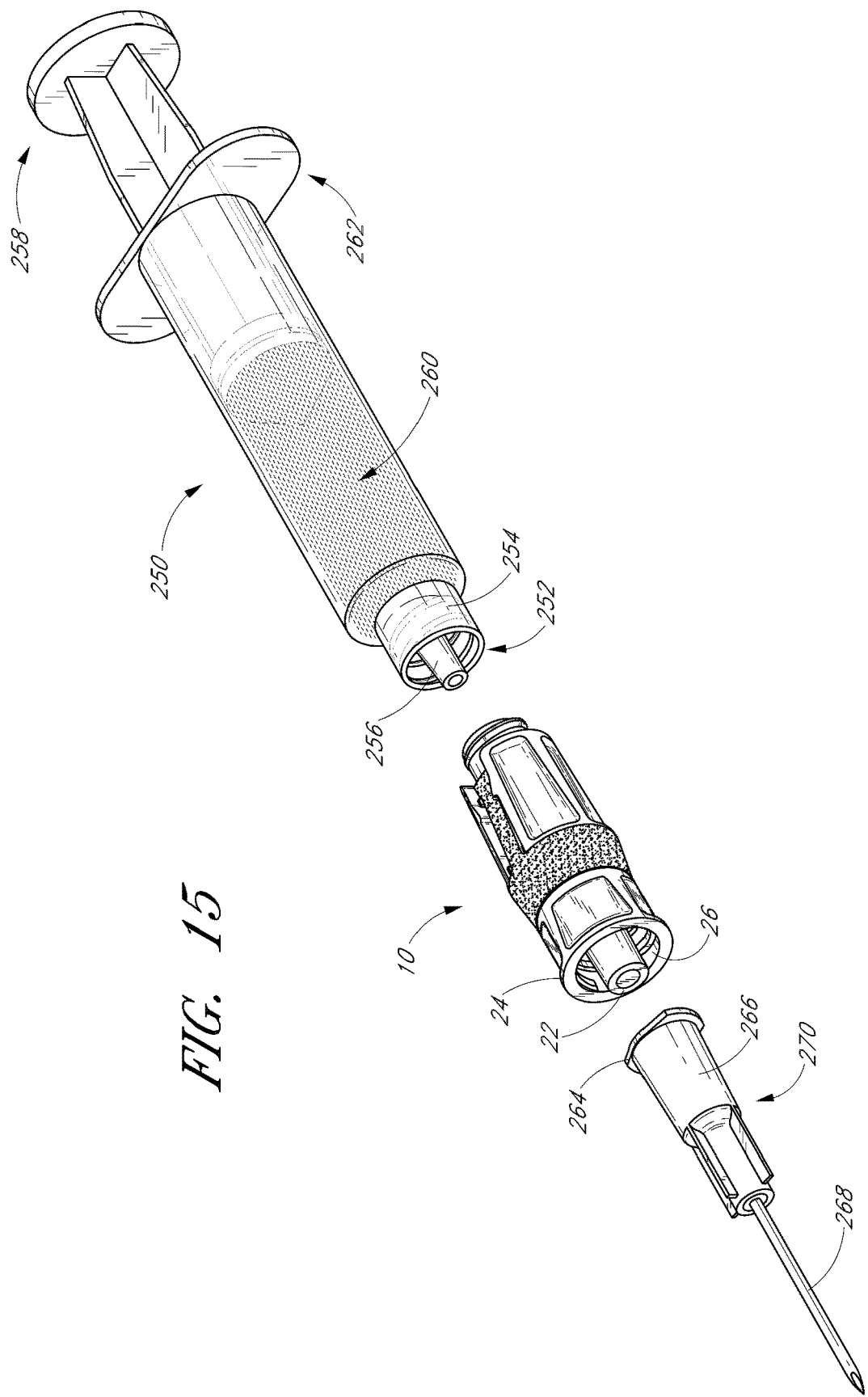
FIG. 15 shows a perspective view of the a closeable male luer connector located with its first end adjacent a syringe with a male luer tip and with its second end located adjacent a hypodermic needle with a female luer attachment portion.

Referring to FIG. 15, the connector 10 is shown adjacent to and between a syringe 250 and a hypodermic needle with sheath 270. The syringe 250, like that of FIG. 12, can comprise a male luer connector 252, a plunger 258, a reservoir 260, and convenient finger anchors 262. The luer connector 252 can further comprise an internally threaded shroud 254 and a syringe luer tip 256. The needle with sheath 270 can comprise a housing 266 with raised tabs 264 on the engagement end and a needle 268.

Figure 16:
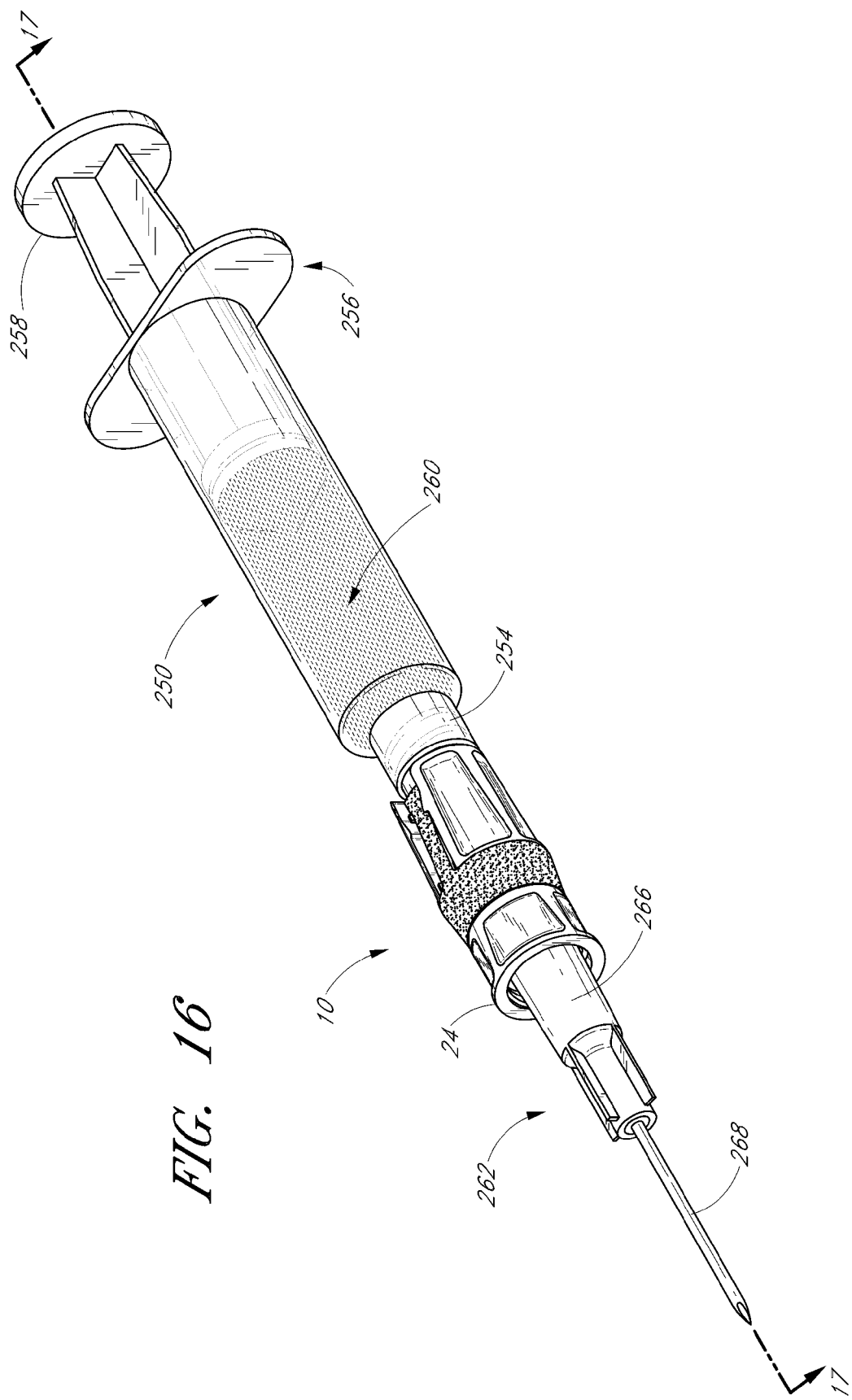
FIG. 16 shows a perspective view of the components of FIG. 15 in engagement. At this stage, fluid can flow through the connector.

With reference to FIG. 16, the connector 10 is shown threadedly engaged with both the syringe 250 and needle with sheath 270. The threaded surface 150 of the valve member 16 of the connector 10 can engage with the threaded shroud 154 of the syringe 250. Accordingly, the luer tip 256 can protrude into the tube 40 of the valve member 16. Similarly, the raised tabs 264 can engage with the inner threads 26 of the shroud 24 of the connector 10. The luer tip 22 of the connector 10 can protrude into the housing 266 of the needle sheath.

Figure 17:
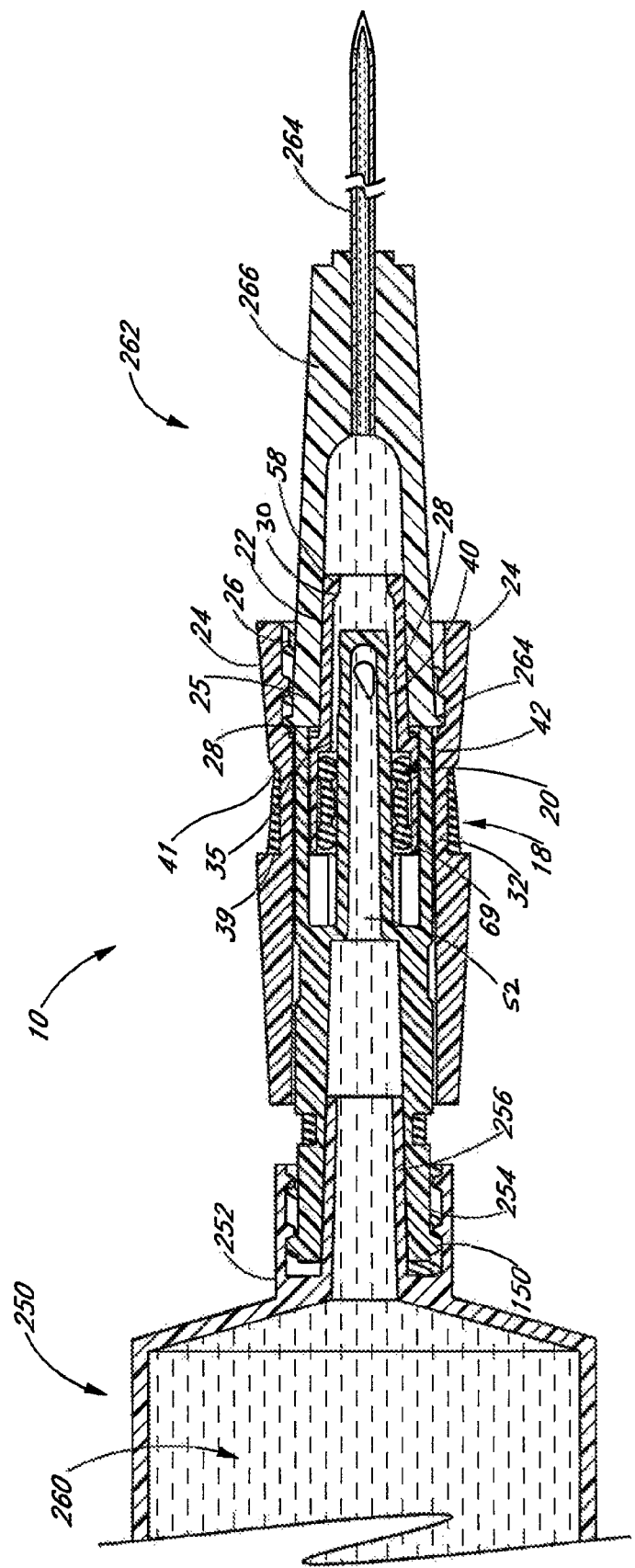
FIG. 17 is a cross-sectional view of the connector, male luer tip of the syringe, and hypodermic needle of FIG. 16. At this stage, fluid can flow through the connector.

In FIG. 17, the engagement shown in FIG. 16 is illustrated in a cross-sectional view. The connector 10 is engaged by a syringe 250 and a needle with a sheath 270. The syringe 250 is threadedly engaged with the threaded surface 150 of the valve member 16 of the connector 10. The needle with sheath 270 is threadedly engaged with the inner threads 26 of the shroud 24.

The luer tip 256 of the syringe 250 protrudes into the tube 40 of the valve member 16. The reservoir 260 of the syringe 250 is in fluid communication with the tube 40 of the valve member 16 through the luer tip 256.

The connector 10 is engaged with the needle with a sheath 270. The housing 266 of the needle with sheath 270 has raised tabs 264 near its proximal end. The raised tabs 264 threadedly engage the inner threads 26 of the shroud 24 of the connector 10. As the luer tip 22 advances into the housing 266 of the needle 268, the proximal end of the housing 266 can contact the struts 42 of the valve member 16. When the needle with sheath 270 is fully engaged with the connector 10, the valve member 16 has been displaced a distance which separates the flange section 58 from the tapered interior wall of the lumen 28 sufficiently to permit fluid to flow out the windows 54 of the valve portion 16. The fluid can then flow out the hole 30' in the end of the luer tip 22 and into the housing 266 of the needle with sheath 270. The hollow needle 268 permits the fluid to flow from within the housing 266 out the distal tip of the needle 268. The sealing portion 20 preferably maintains a fluid barrier between the outer surface of the tube 40 and the inner surface of the lumen 28, confining the fluid in the lumen and the direction of flow toward the hole 30' in the luer tip 22. Thus, at this stage, the syringe 250 is in fluid communication with the distal tip of the needle 268. As was previously illustrated in FIGS. 13 and 14, in some embodiments, the connector 10 will generally not permit fluid to flow out of the syringe 250 without a component engaged with the second end 14 of the connector 10. The component illustrated in FIGS. 15-17 is a needle with a sheath 270; however, other components, such as those which permit fluid flow and possess a female luer engagement portion, can also be used.

Figure 18A:
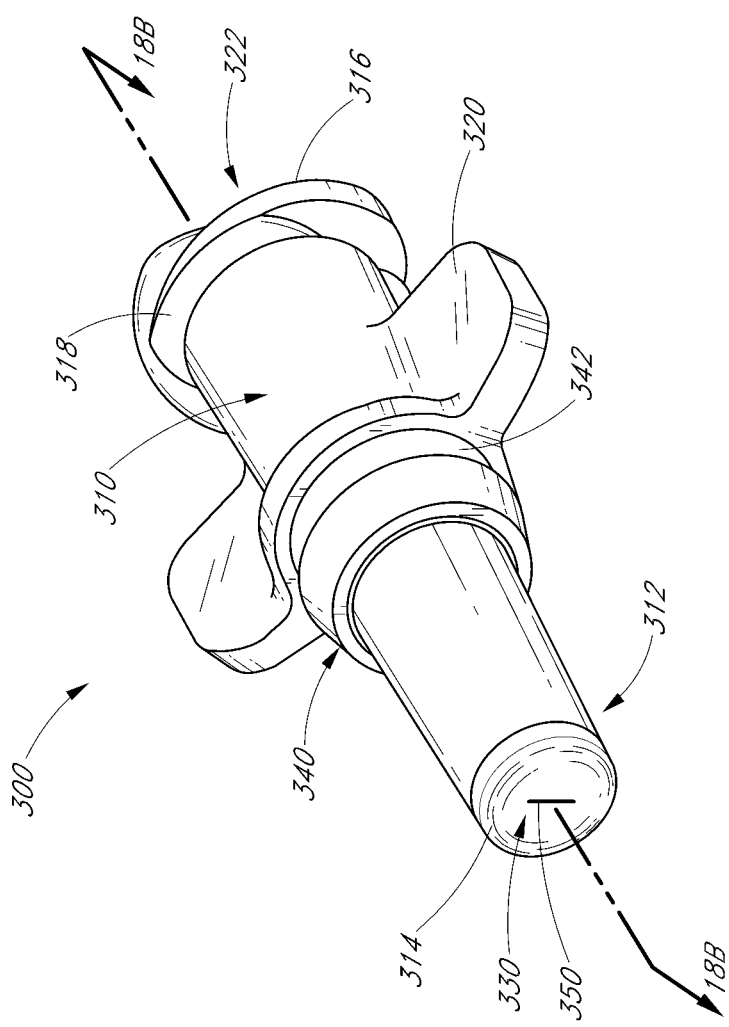
FIG. 18A is a perspective view of another embodiment of a closeable male luer connector.

FIG. 18A displays a perspective view of another embodiment of a closeable male luer. The rotatable connector 300 is comprised of a housing 310, an internal passageway 322 and a seal element 330. The housing is further comprised of a luer tip 312, a luer receiver 316 at the first end of the connector 300, an engagement portion 318, a manipulation portion 320, and a raised portion 340. The seal element 330 can have an opening 350 along its face 314 in a transverse direction. The internal passageway 322 can extend from the luer receiver 316 to the luer tip 312. The housing 310 can be composed of a water-impermeable material, such as a polycarbonate plastic. The housing 310 can also be composed of a hydrophobic plastic. Other examples of materials suitable for construction of the housing 310 are glassed-filled GE Valox 420 or polypropylene. Depending on the application, many other materials can also be used.

The housing 310 illustrated is configured to receive a male luer tip at the luer receiver 316 by threadedly engaging the male luer at its engagement portion 318. The receiver 316 can conform to ANSI standards for a luer receiver. The illustrated manipulation portion 320 has two tabs extending radially from the central axis of the housing 310. The manipulation portion 320 is configured to aid the user in grasping and rotating the connector 300.

The housing 310 illustrated is also constructed to provide a closeable male luer at its second end. The luer tip 312 at the second end can be constructed to ANSI standards for a male luer tip. The luer tip joins the main body of the housing 310 at the raised portion 340. The raised portion 340 is constructed to inhibit the luer tip 312 from advancing too far into a luer receiver. The housing 310 can also have a recessed portion 342 behind the raised portion 340. The luer tip 312 can also have a seal element 330 which has a face 314 towards the second end of the connector. The seal element 330 can be any water-impermeable, resilient material, including without limitation, silicone. The selection of the material for construction of the seal can be accomplished by one skilled in the art. The luer tip 312 can taper smaller in a direction from the raised portion 340 as it approaches its second end.

The seal element 330 can also have an opening 350 in the face 314 toward the second end of the connector prior to engagement with any other component. The opening 350 can be a slit in a transverse direction to the longitudinal axis of the housing 310. The opening 350 can be centered across the face 314, or located in another position on the face 314. The seal element 330 can cover the entire second end of the luer tip 312, or only a portion thereof. The seal element 330 can be attached to the housing by an overmolding process, among other attachment methods. In such an overmolding process, the housing 310 can be formed by injection molding in a first step, and then in a second step, the housing 310 can be re-inserted into a mold (or remain in a mold) and an appropriately sized molding pin (not shown) can be inserted through a wider end of the housing 310, such as the second end. Silicone material can then be injected into the mold to form the seal element 330. In other embodiments, the seal element 330 can be glued or otherwise adhered into the housing 310.

As can be seen from the illustrated embodiment in FIG. 18A, the seal element 330 can inhibit fluid from flowing through the housing 310 when the luer tip 312 is not engaged with another component. Thus, when a fluid-containing component (not shown) with a male luer connector is connected to the luer receiver 316, the connector 300 can be used to control flow of fluid through its luer tip 312. For example, when a fluid-containing component such as a syringe is engaged with the connector 300, fluid is permitted to fill the housing 310 of the connector 300 by flowing through the internal passageway 322, but the seal element 330 can substantially inhibit flow of fluid out the luer tip 312. If the interior space of the housing is filled with air or another gas before the fluid enters, the connector 300 may need to be opened to allow the air or other gas to escape before the fluid can enter. In some embodiments, as described in detail below, the internal surface of the seal element 330 can be adapted to increase the resistance against the widening of the opening 350, which could allow fluid to escape when the fluid (not shown) exerts a pressure against the seal element 330 from the internal passageway 322. Thus, the connector 300 inhibits flow of fluid from a fluid-bearing component when the connector 300 is attached to the male luer of the fluid-bearing component without another component connected to the luer tip 312 of the connector 300.

In some modes of use, the opening 350 on the face 314 of the seal element 330, normally closed in the position shown, can be opened when the luer tip 312 comes in contact with a suitable female connector, such as a Clave® connector sold by ICU Medical, San Clemente, Calif. An illustrated engagement of this configuration is discussed in detail below. The engagement can be achieved in many other ways, and with many other structures, including connectors other than the Clave connector.

FIG. 18B is a cross-sectional view of the connector 300 illustrated in FIG. 18A. The connector 300 can have an internal passageway 322 which connects the luer receiver 316 to the luer tip 312. The engagement portion 318 can be configured to receive an internally threaded shroud of a male luer connector (see FIG. 19). The manipulating portion 320 can extend radially away from the internal passageway 322, as shown. The seal element 330 can extend along at least part of the internal passageway 322, and can be disposed across at least part of the second end of the connector 300. The seal element 330 can extend beyond the end of the luer tip 312. The seal element 330 can have a cross-sectional area approximately equal to the housing 310 at the end of the luer tip 312. In those embodiments where the luer tip 312 and seal element 330 are generally circular, the outside diameter of the seal element 330 can be equal to the outside diameter of the luer tip 312. The seal element 330 is not confined to a circular shape (nor are any other structures disclosed herein), and other shapes can be used. In other embodiments, the seal element 330 does not extend beyond the end of the housing 310 towards the second end of the connector 300, but can have a maximum outer dimension equal to that of the inner dimension of the luer tip 312. The seal element 330 can have a closing portion 324. The closing portion 324 can permit fluid flow through the seal element 330 of the connector 300, but is biased to generally close the opening 350 in the seal element 330. The structure of the closing portion 324 can be adapted to resist permitting fluid (not shown) from exiting the opening 350 when the luer tip 312 is not engaged with another component, as described in further detail below.

As can be seen in FIG. 18C, which is a detail of the cross-sectional view presented in FIG. 18B, the seal element 330 can comprise the entire face of the second end of the connector 300. In other embodiments, the seal element 330 may not extend beyond the housing 300. The internal passageway 322 can extend to the seal at the second end of the connector 300.

Figure 19:
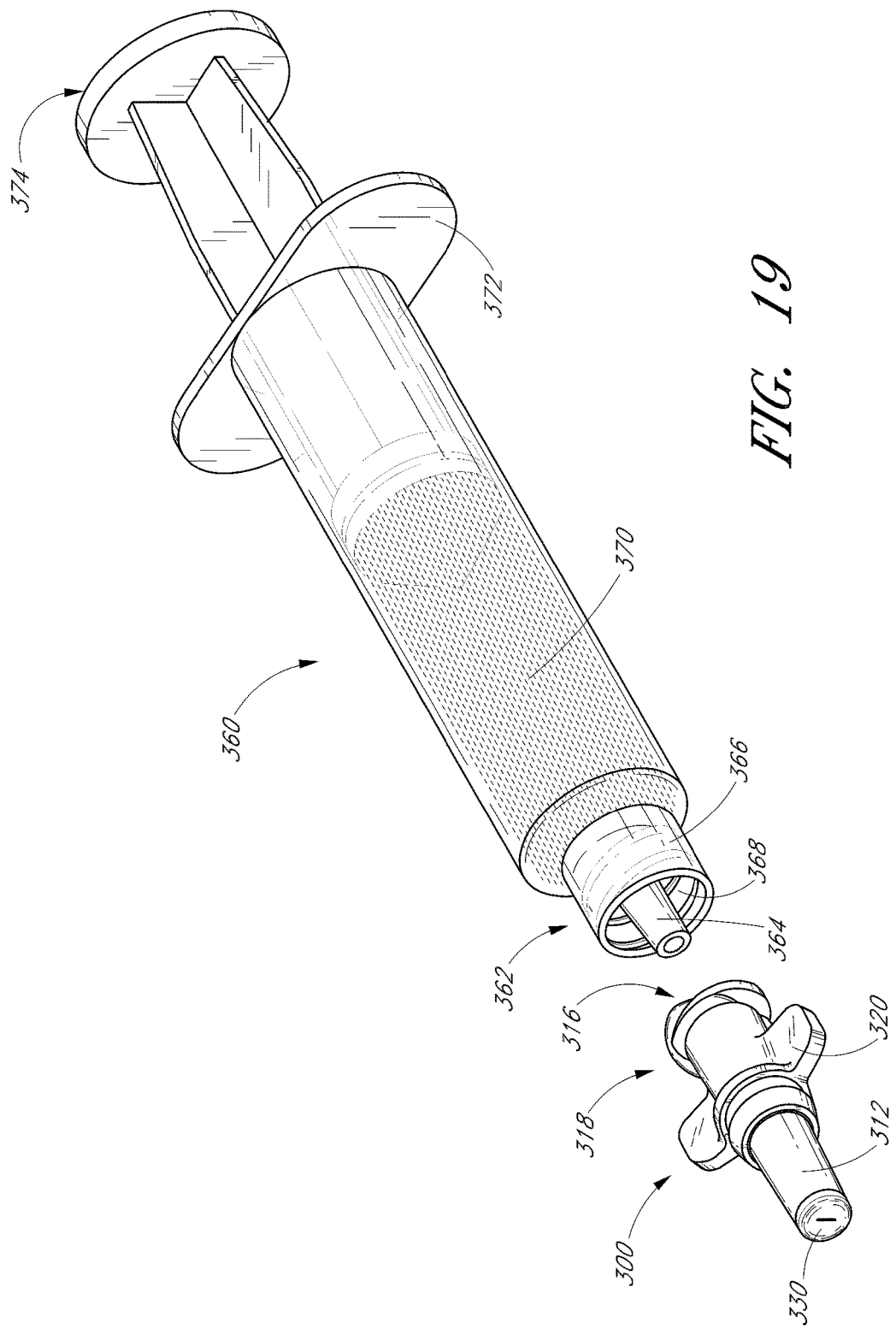
FIG. 19 is a perspective view of the connector of FIG. 18A located adjacent a syringe with a male luer tip.

FIG. 19 illustrates a perspective view of the connector 300 adjacent a syringe 360. As in previous descriptions, the syringe can comprise a male luer connector 362, a fluid reservoir 370, a plunger 374, and finger anchors 372. The luer receiver 316 of the connector 300, which can be of appropriate size and shape to engage with standard luer connectors, is positioned to receive the luer tip 364 of the syringe 360. The internal threads 368 of the shroud 364 of the syringe 360 are properly aligned to threadedly connect with the engagement portion 318. In this way, the receiver 316 can engage the luer connector 362 and connect the connector 300 to the syringe 360. Before engagement of the syringe 360 with the connector 300, the fluid within the reservoir 370 is not inhibited from exiting the luer tip 364 by any physical component.

Figure 20:
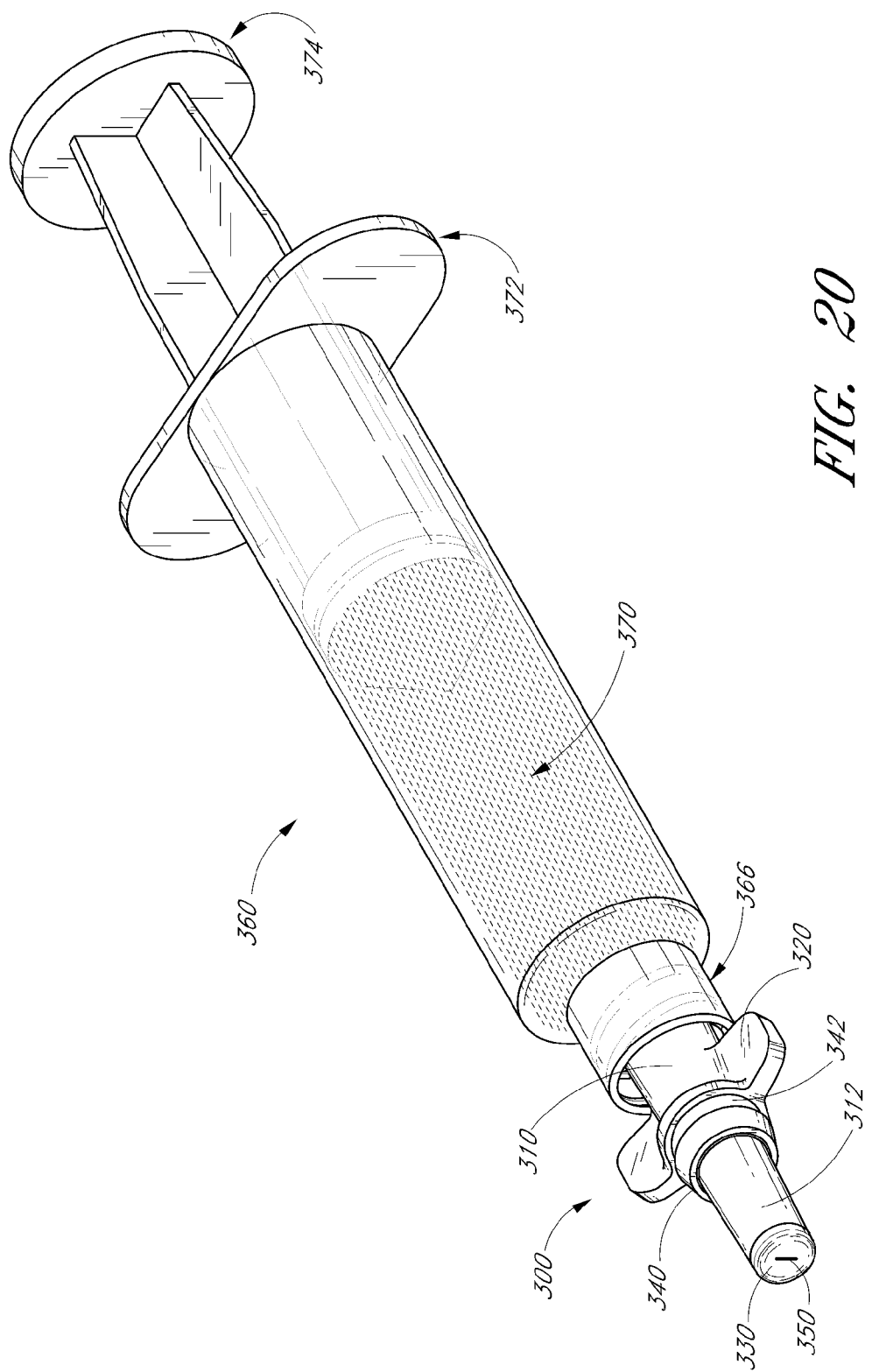
FIG. 20 is a perspective view of the components of FIG. 19 in engagement.

Referring now to FIG. 20, a perspective view of the connector 300 threadedly connected to a syringe 360 is shown. The connector 300 can be connected to the syringe 360, or other medical implement, by many other means, such as glue, adhesive, solvent, ultrasonic welding, epoxy, interference fits, mechanical connections, and/or unitary constructions. The receiver 316 (not shown) contains at least part of the luer tip 364 of the syringe 360. The luer tip 364 extends at least partially into the internal passageway 322. The threaded engagement portion 318 is engaged with the internal threads 368 of the shroud 364 of the syringe 360. Fluid from the reservoir 370 can then flow freely within the housing 310 of the connector 300, by way of the internal passageway 322. If the interior space of the housing is filled with air or another gas before the fluid enters, the connector 300 can be opened to allow the air or other gas to escape before the fluid can enter. In some cases, the housing 310 of the connector 300 may be filled with a gas, such as air. Before the fluid enters the housing 310, the connector may need to be opened to allow the gas to escape before the fluid can flow. The seal element 330 inhibits fluid from leaving the connector 300. The luer tip 312 of the connector 300 can be used to connect the connector-syringe 300, 360 combination to other components for controlled fluid transfer. The connector 300 can also be formed integrally with the syringe 360 (not shown), such that the housing 310 of the connector is formed by the fluid-delivery end of the syringe. During use of this combination connector-syringe, the male luer tip 312 of the connector 300 can, in effect, replace the luer tip 364 of the syringe for connection purposes.

Certain medications, such as chemotherapy medications, are contact toxins, and avoiding exposure to the skin is desirable. Such medications are often stored in a syringe with a hypodermic needle, such as depicted in FIGS. 15 and 16. Under certain conditions, without the use of a closeable male luer connector, it can be possible for the toxic fluid to flow out of the syringe. Even if steps are taken to avoid accidental fluid flow, such as orienting the syringe with attached needle such that gravity aids the retention of the medication within the syringe, the medication can also vaporize and seep out of the hypodermic needle in a gaseous state. The use of a closeable male luer between the syringe and hypodermic needle inhibits the uncontrolled flow of medication, in both liquid and gaseous states. Accordingly, risk of accidental exposure to such toxic medications is minimized.

Figure 21:
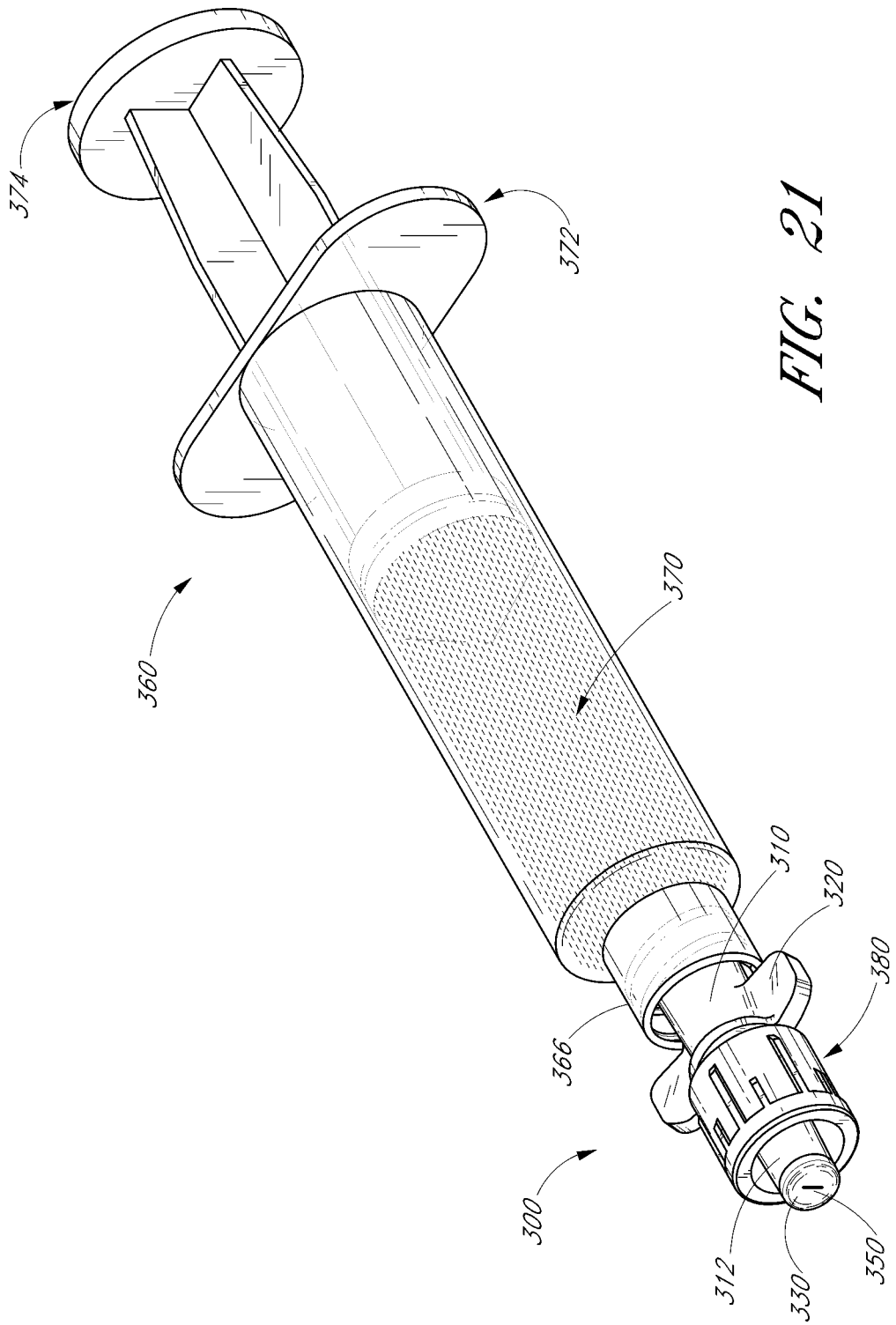
FIG. 21 is a perspective view of another embodiment of a closeable male luer connector engaged with a syringe with a male luer tip.

Referring now to FIG. 21, the closeable male luer connector 300 is illustrated in another embodiment, wherein an internally threaded shroud 380 is disposed on the housing 310. The shroud 380 at least partially or entirely encircles the housing 310 at approximately the recessed portion 342 (visible in FIG. 18A). In some embodiments, the shroud 380 is not attached to the connector 300, and instead can rotate freely about the longitudinal axis of the connector 300. The raised portion 340 (visible in FIG. 18A) can inhibit the movement of the shroud 380 towards the luer tip 312 of the connector 300. Additionally, the manipulation portion 320 of the connector 300 can inhibit the movement of the shroud 380 towards the luer receiver 316. The shroud 380 can be threaded consistent with ANSI specifications for luer connectors. The shroud 380 can assist the luer tip 312 in forming a connection between the connector 300 and other components (not shown).

With reference now to FIG. 22A, the cross-section of a closeable male luer connector 400 with a continuously tapering internal passageway 402 is illustrated. The housing's 404 tapering internal passageway 402 permits for varied injection molding techniques of manufacture. For example, if the taper is wider at an end with a luer receiver 406, a molding pin can be tapered in a corresponding manner to closely fit against the wall of the internal passageway 402, producing a seal 408 that is shorter than the seal illustrated in FIG. 18B.

With reference to FIG. 22B, the seal 408 in the illustrated embodiment has a closing portion 412 similar to that of the closing portion 324 in FIG. 18B. In addition, the internal surface of the seal 408 can be adapted to increase resistance against permitting fluid from exiting the opening 410 when a fluid (not shown) in the internal passageway 402 exerts a pressure against the seal 408. The internal surface of the closing portion 412 can include slanted surfaces against which such fluid presses to urge the opening 410 more tightly closed.

Figure 23A:
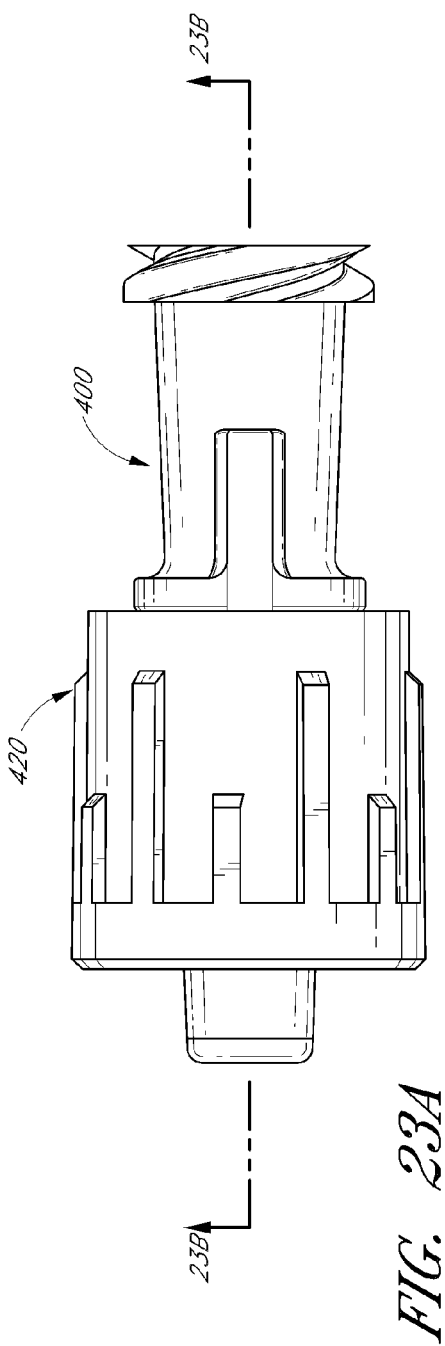
FIG. 23A is a side view of another embodiment of a closeable male luer connector with a shroud.

Turning to FIG. 23A, a side view of another embodiment of the connector 400 of FIG. 22A is displayed. An internally threaded shroud 420 is disposed about the outer surface of the housing 404.

Figure 23B:
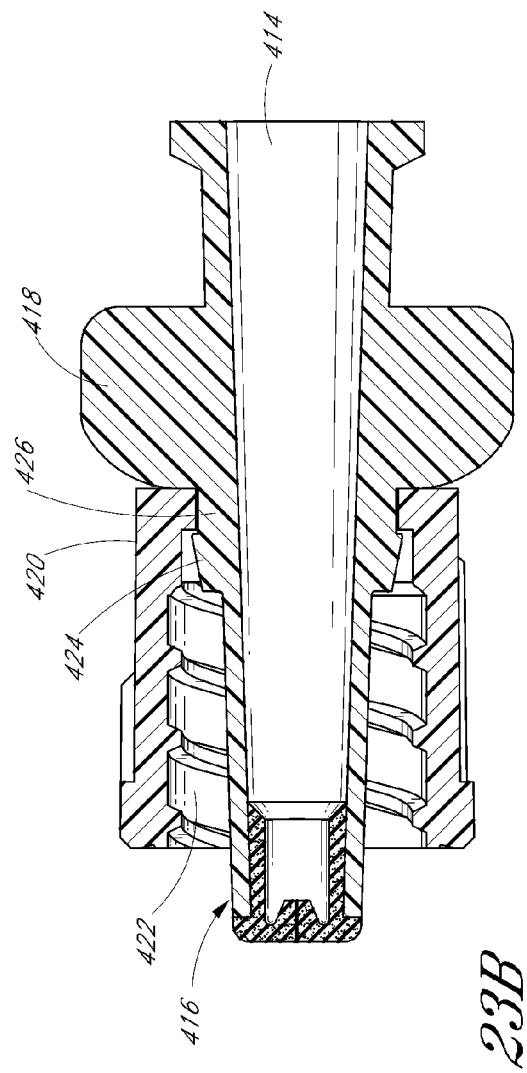
FIG. 23B is a cross-sectional view of the connector of FIG. 23A.

As can be seen in FIG. 23B, the housing 404 can have a raised portion 424 which inhibits axial movement of the shroud 420 toward the luer tip 416. The housing 404 can also have a manipulation portion 418 which extends radially outwardly from the longitudinal axis of the connector 400. The housing 404 also has an internal passageway 428 extending from the luer receiver 414 to the seal element 430. The manipulation portion 418 can inhibit movement of the shroud towards the luer receiver 414 of the connector 400. The manipulation portion can also be a convenient place for the user to place his or her fingers while turning the connector 400. Additionally, there can be a recessed portion 426 of the connector 400. The recessed portion 426 can be a portion of the connector 400 with a smaller outer diameter than the outer diameter of the raised portion 424 or the manipulation portion 418. The shroud 420 can be disposed on the connector 400 such that a narrow portion of the shroud 420 encircles the connector 400 about the recessed portion 426. The shroud 420 can be unaffixed to the housing 404 and thus free to rotate. The internal threads 422 of the shroud can conform to ANSI standards for luer connectors, allowing the shroud to assist the luer tip 416 in engaging the female connector of another component (not shown).

Figure 23C:
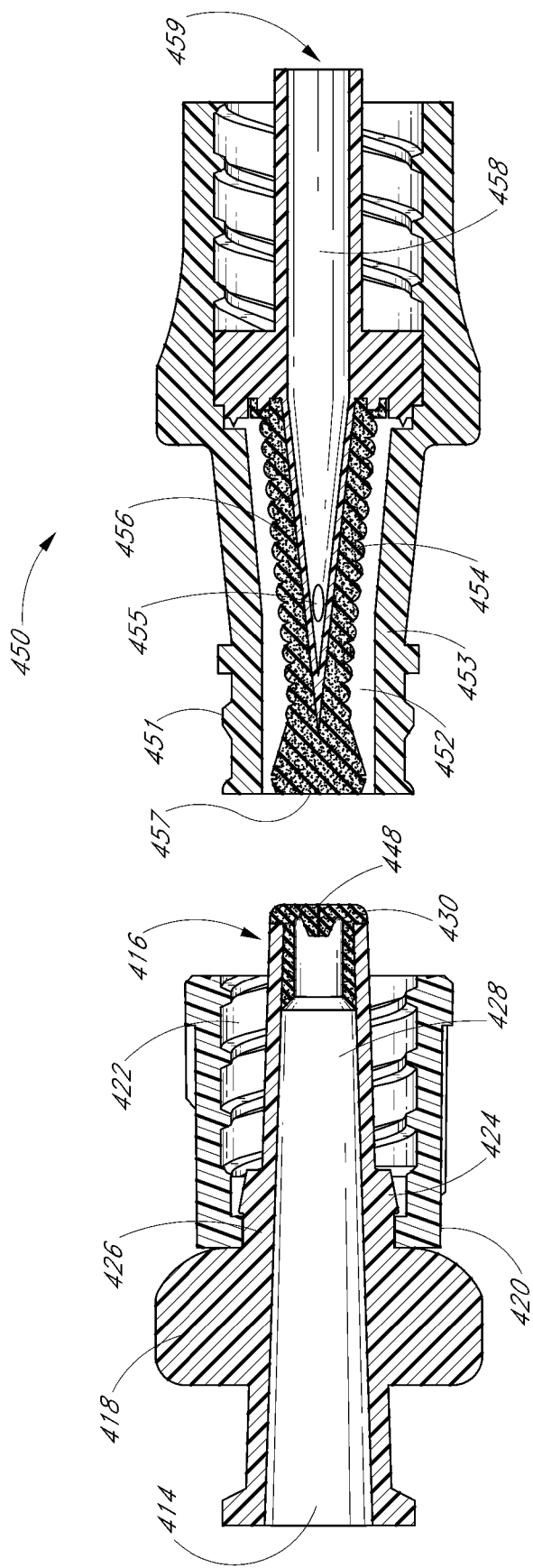
FIG. 23C is a perspective view an embodiment of a closeable male luer connector adjacent a closeable female connector. At this stage, fluid flow is impeded through the female luer connector.

FIG. 23C depicts the closeable male luer connector 400 of FIG. 23B in the proximity to a suitable female connector 450, such as a Clave® connector sold by ICU Medical, San Clemente, Calif. The female connector 450 is similar to that illustrated in FIG. 10.

Figure 23D:
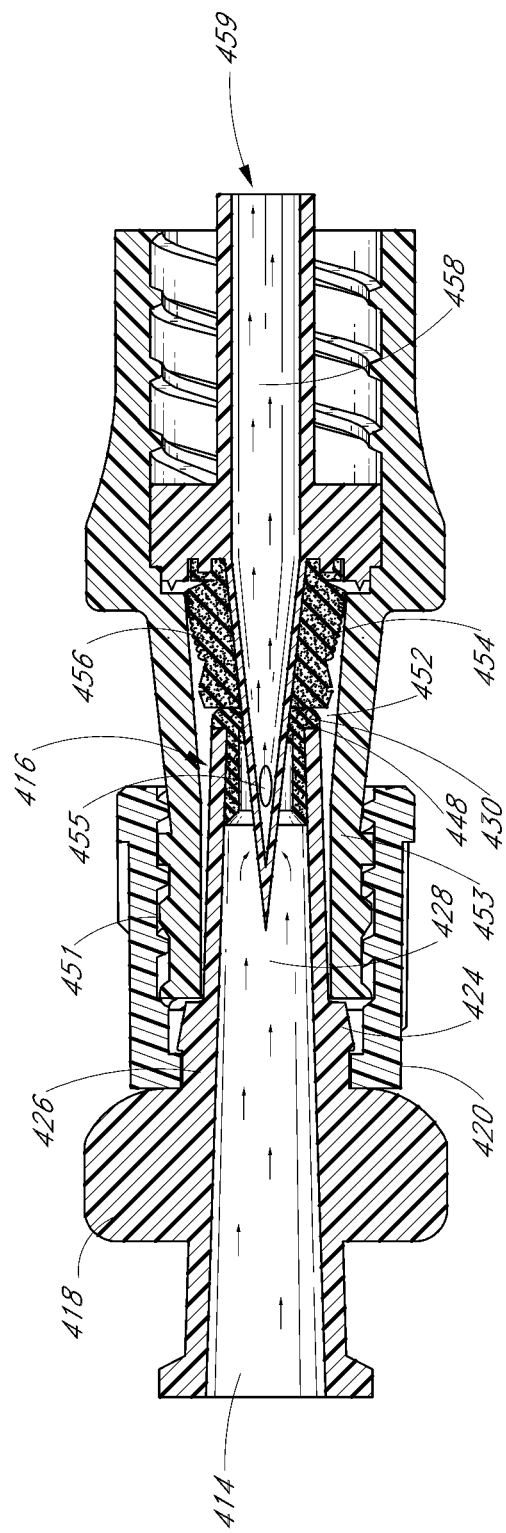
FIG. 23D is a perspective view of the components of FIG. 23C in engagement.

FIG. 23D illustrates an engagement between the male luer connector 400 and female connector 450. The internal threads of the shroud 420 can engage with a threaded region 451 of the female connector 450. The luer tip 416 of the male luer connector 400 can advance into the female connector 450 by compressing a compressible seal 454. As the male connector 400 advances, a stationary fluid conduit 456 of the female connector 450 can penetrate the opening 448 in the seal element 430 of male connector 400. The fluid conduit 456 can advance far enough into the male connector 400 that the holes 455 advance into the internal passageway 428 of the male connector 400. Once the holes 455 of the female connector 450 are disposed within the internal passageway 428 of the male connector, fluid can flow from the luer receiver 414 of the male connector 400 through the internal passageway 428 of the male connector 400 to the holes 455 of the fluid conduit 456 of the female connector 450. The fluid can then flow through the holes 455 and into a fluid conduit 458 of the female connector 450. Thus, fluid can flow from the first end of the male connector 400 to the distal end of the female connector 450 when the two are engaged. When the connectors 400, 450 are disengaged, the fluid conduit 456 withdraws from the internal passageway 428 and the seal element 430 closes, thereby inhibiting fluid flow through the male connector 400. Additionally, the compressible seal 411 of the female connector 450 returns to its original position, and inhibits flow through the holes 455 in the fluid conduit 456.

With reference now to FIG. 24A, a closeable male luer connector 500 is displayed in a perspective view. The connector 500 has a housing 510 and a seal 514. The housing is comprised of a manipulation portion 512. In this exemplary illustration, the manipulation portion 512 includes wings 516. The wings 516 are adapted to provide a place for the user to grasp and rotate the housing 510 of the connector 500.

Referring now to FIG. 24B, the connector 500 of FIG. 23A is shown in cross-section. The wings 516 are shown as extending outward from the longitudinal axis of the connector 500 and towards the luer receiver 518 of the connector. The internal passageway 520 of the housing 510 has a continual taper, as described in the embodiment of the connector 400 in FIG. 22A.

Turning to FIG. 25A, a side view of a closeable male luer connector 600 is illustrated. The connector 600 has a housing 610, a seal element 614, and a shroud 620. The housing comprises an internal passageway 640, a luer tip 612, and a manipulation portion 616. The manipulation portion can be constructed to comprise two wings 630, as described in FIG. 24A. The shroud can have internal threading 622, and such threading can be constructed to comply with ANSI specifications for luer connectors. The seal element 614 can be biased closed when not engaged.

With reference now to FIG. 25B, a cross-sectional view of the connector 600 from FIG. 25A is displayed. The shroud 620 can encircle the housing 610 at a recessed portion 652 of the housing 610. A raised portion 650 can inhibit motion of the shroud 620 in the direction of the second end of the connector 600 while the manipulation portion 616 can inhibit motion of the shroud in the direction of the first end of the connector 600. The internal threading 622 of the shroud 620 can be used to engage other components (not shown) when used in conjunction with the luer tip 612. The continuously tapering internal passageway 640 has characteristics that assist in injection molding as discussed with regard to FIG. 22A.

Figure 26A:
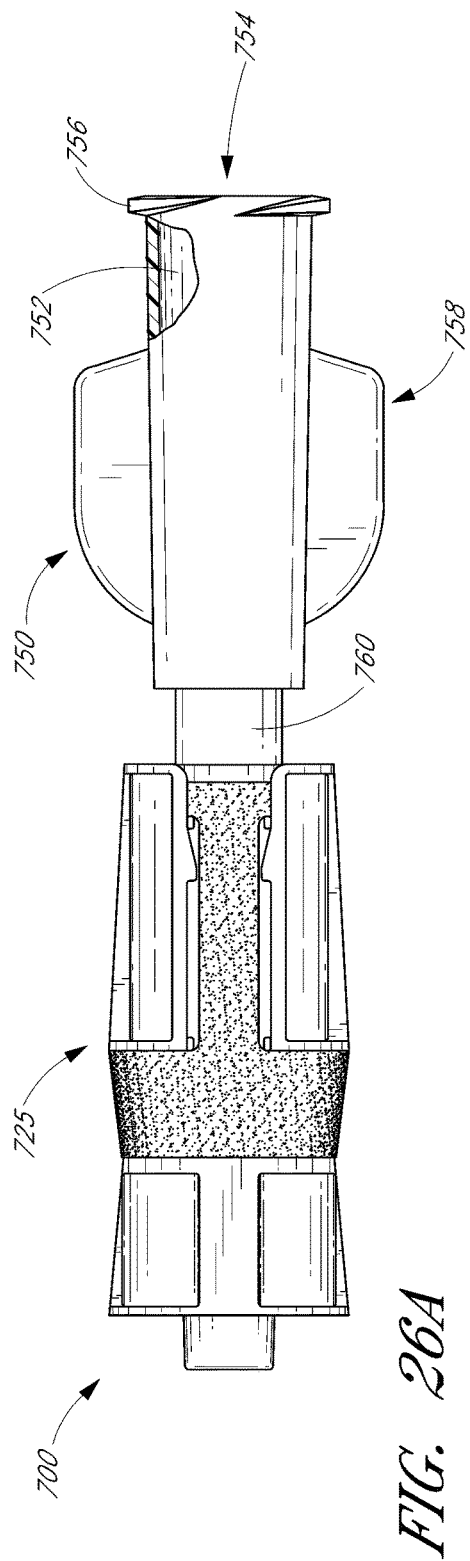
FIG. 26A is a perspective view of another embodiment of a closeable male luer with a flexibly connected female luer connector.

Referring to FIG. 26A, a perspective view of a closeable male luer assembly 725 comprising a closeable male luer 700 and a flexibly connected female luer connector 750 is displayed. The closeable male luer 700 can embody any number of the aspects and features described in this application. The female luer connector 750 is adapted to receive a standard male luer connector (not shown). The female luer connector 750 is located adjacent the male luer connector 700 and flexibly connected to it. The female luer connector 750 comprises an internal passageway 752, a luer receiver 754, and an engagement portion 756. The internal passageway 752 places the luer receiver 754 in fluid communication with an internal passageway of the closeable male luer connector 700. The closeable male luer connector 700 can be attached to the female luer connector 750 through a flexible segment 760. In some embodiments, such a segment 760 can include an accordion-like flexible portion of resilient material. In other embodiments, a straight, flexible material can be used. In other embodiments, both a flexible outer segment and a flexible tube can be used to connect the closeable male luer 700 with the female luer 750.

The flexible segment 752 permits the user to orient the female connector 750 of the assembly 725 in a different attitude than that of the closeable male luer connector 700. As an example, the closeable male luer 700 can remain stationary against a patient's arm while the female connector 750 is angled away from the arm to assist in easy connection with a syringe or other component (not shown). By flexibly connecting the closeable male luer 700 to the female luer connector 750, the moment generated by moving the female luer connector 750 is accepted at a point between the two components of the assembly 725 and is less likely to be transmitted to another component (not shown) attached to the closeable male luer connector 700. Such a component could include an I.V. site, where angling of the connection could result in harm to the patient. Moreover, the moment will be less likely to bend and/or dislodge the tip of the tube 40 from the interior of the lumen 28 (see, e.g., FIG. 28).

Figure 26B:
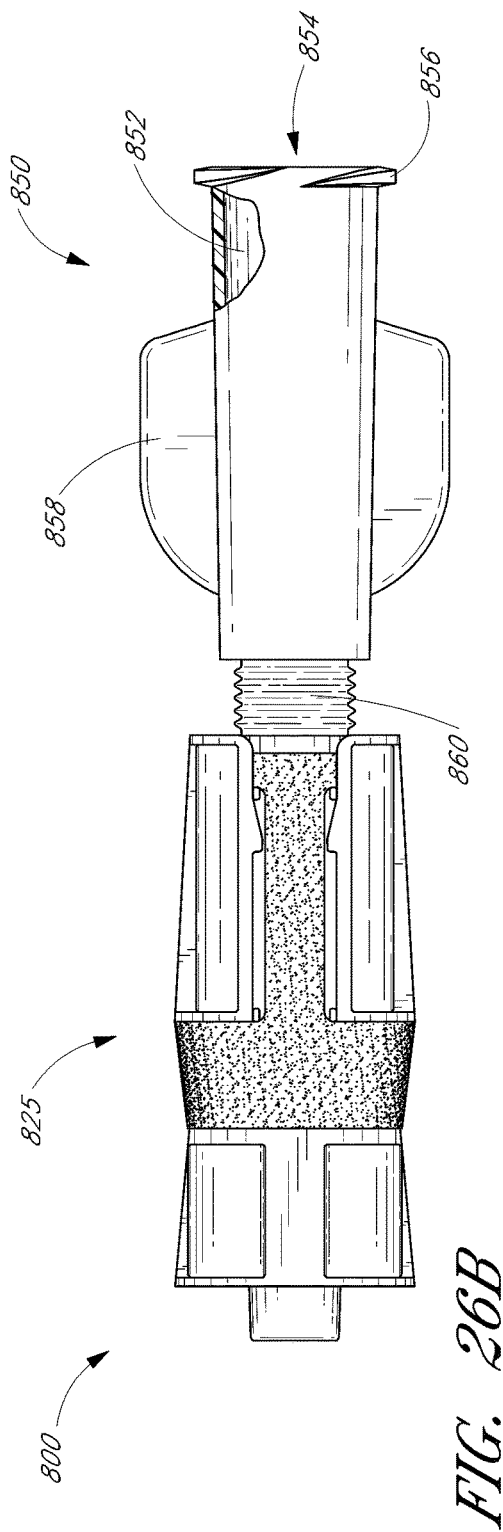
FIG. 26B is a perspective view of another embodiment of a closeable male luer with a flexibly connected female luer connector.

FIG. 26B illustrates another embodiment of a closeable male luer assembly 800 comprising a closeable male luer connector 825 and a flexibly connected female luer connector 850. The connectors 825, 850 and their components are similar in many respects to the embodiment depicted in FIG. 26 and can embody any number of the aspects and features described above. The closeable male luer connector 825 and the female luer connector 850 are flexibly connected by a connecting member 860. The connecting member 860 places the connectors 825, 850 in fluid communication. The connecting member 860 illustrated here comprises an accordion-shaped plastic conduit. The connecting member 860 is configured to permit the closeable male connector 825 and the female luer connector 850 to be positioned at different angular orientations. By way of example, the closeable male luer connector 825 can remain stationary while the female luer connector 850 can be positioned at an angle to the closeable male luer connector 825. In another example, the female luer connector 850 can remain stationary while the closeable male luer connector can be positioned at an angle to the female luer connector 850. In yet another example, the closeable male luer connector 825 and the female luer connector 850 can both be placed at an angle.

FIGS. 27-32 illustrate another embodiment of a closeable male luer connector 900 with a male end 902 and a female end 904. In some respects, the connector 900 is similar in structure and assembly to other embodiments disclosed and illustrated herein. For example, the connector 900 can include an outer housing 906, a shroud 908, a resilient member 910, an internal valve member 912, and an internal sealing portion 914. All of the descriptions, illustrations, and features of each embodiment disclosed herein can be applied to other embodiments disclosed herein. As described below, the connector 900 can be effective in preventing or minimizing the potential dripping of fluid out of the male end 902 when the male end 902 is in the process of closing.

Figure 28:
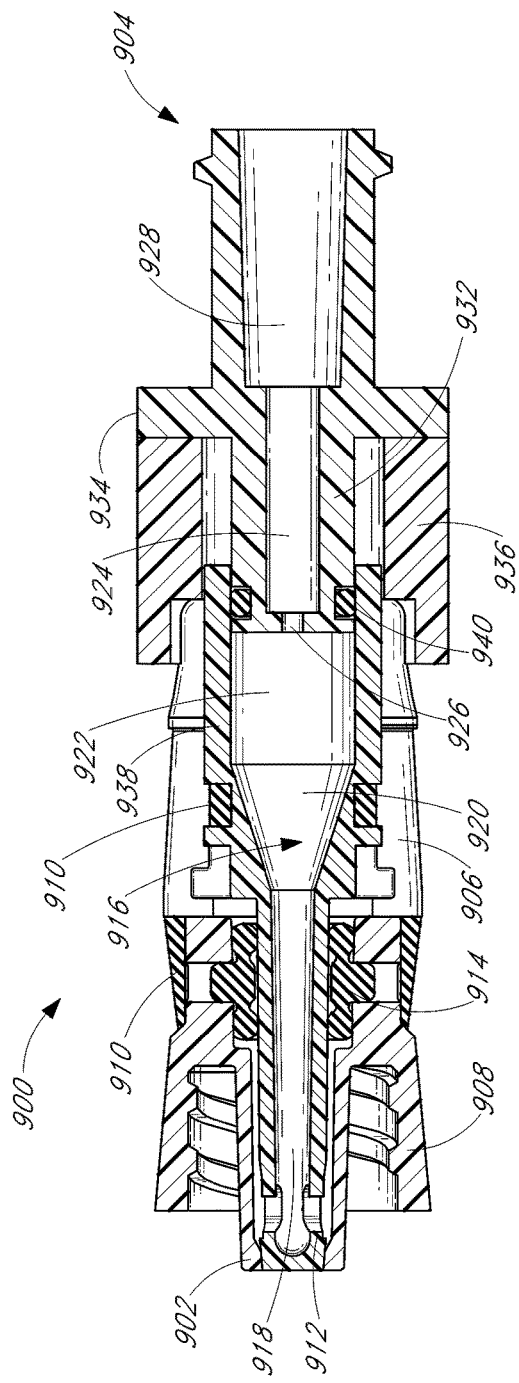
FIG. 28 is a cross-sectional view of the connector of FIG. 27.
Figure 29:
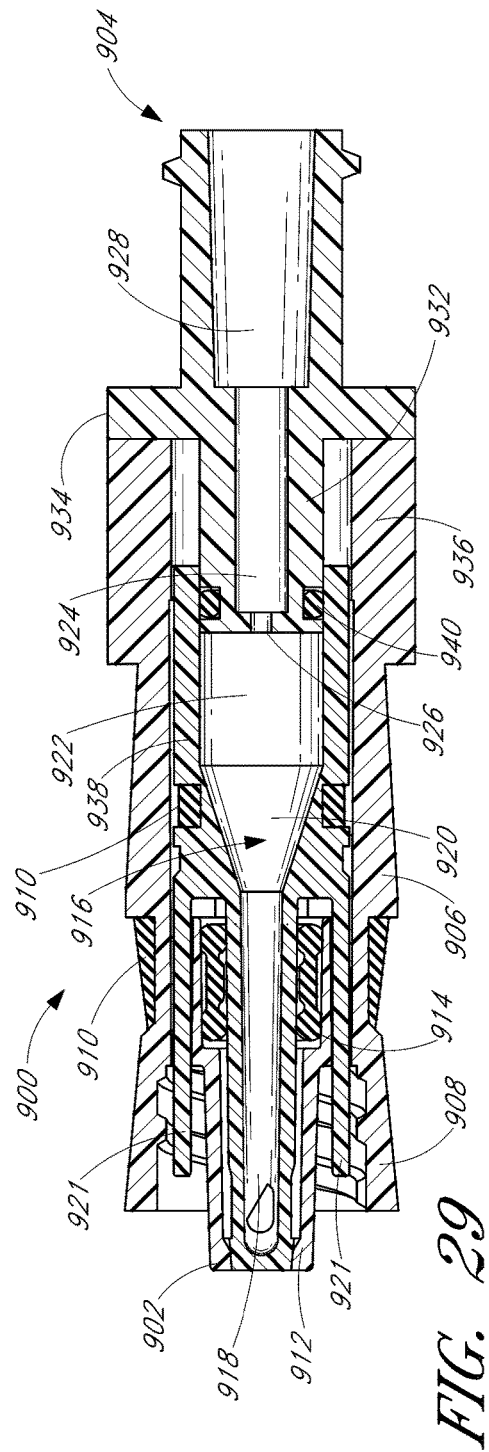
FIG. 29 is another cross-sectional view of the connector of FIG. 27.

As illustrated in FIGS. 28 and 29, the valve member 912 can have an internal fluid passageway 916 with a varying cross-sectional area. In some embodiments, the valve member 912 does not have an internal passageway and fluid instead flows around the valve member 912. As shown, the cross-sectional area of a region 918 of the passageway 916 positioned generally within the male end 902 of the housing 906 can be relatively narrow; the cross-sectional area of a region 920 of the passageway 916 positioned generally in the middle of the connector 900 can be wider and have a tapering wall as shown; a region 922 of the passageway 916 positioned closer to the female end 904 can have a larger internal volume than the second region 920; a region 924 of the passageway 916 can be connected to region 922 by way of a narrow opening 926; and a region 928 can be connected to region 924. In some embodiments, region 928 can be connected to region 924 by way of a narrow opening (not shown). In some embodiments, the connector 900 can also include one or more struts 921 to facilitate opening the connector 900.

As discussed above, the region 928 and the female end 904 of the housing 906 can be structured to include one or more of the components of the closing female end of connectors 21, 210 (and/or any components from other types of closing female connectors) to permit the female end 904 of the connector 910 to be selectively opened or closed to fluid flow.

An internal conduit 932 can partially or completely surround the region 924 of the internal fluid passageway 916. The conduit 932 can be secured to a base 934, and the base 934 can be secured to the female end 904 on one side and to an intermediate portion 936 on the other side. In the illustrated embodiment, the outer perimeter of the base 934 extends to the outer perimeter of the housing 906, but it can be configured in many other ways. The intermediate portion 936 can be secured to the remainder of the housing 906. On the end of the valve member distal from the male end 902, an internal conduit 938 can surround region 922 of the fluid passageway 916. In the illustrated embodiment, the internal conduit 938 of the valve member is larger in cross-sectional area and in internal volume than is the internal conduit 932 surrounding region 924. A seal element 940 can be positioned in a region of interface between internal conduits 932, 938 to prevent or minimize leakage of fluid out of the passageway 916 at such interface, while permitting relative axial movement between internal conduits 932, 938. In some embodiments, internal conduits 932, 938 are rigid and do not flex or bend under normal operating conditions. In some embodiments, outer housing portions 906, 908, 934, and 936 are molded into a single, contiguous housing. In other embodiments, they may be molded separately and later joined together to form the housing.

Figure 30:
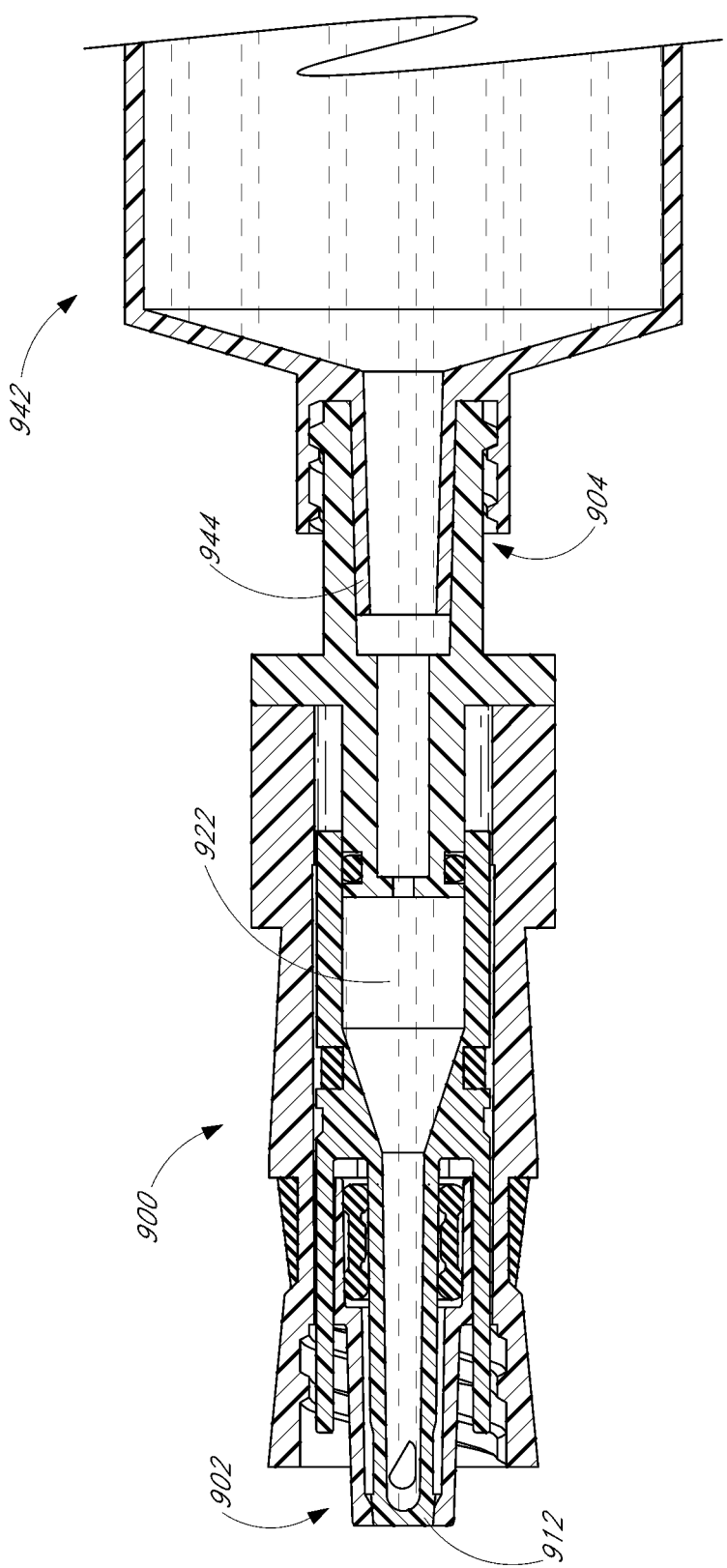
FIG. 30 is a cross-sectional view of the connector of FIG. 27 engaged with a syringe with a male luer tip. At this stage, fluid flow is impeded through the male luer connector.

As shown in FIG. 30, the female end 904 of the connector 900 can be connected to a male portion 944 of another medical implement such as a syringe 942. In this and in all other embodiments disclosed herein, any of a wide variety of other types of medical implements can be attached to the disclosed connectors. In the configuration illustrated in FIG. 30, the connector 900 and syringe 942 are filled with a fluid, such as chemotherapy medication. The fluid cannot escape from the connector 900 under normal conditions because it is impeded on one side by the interface between the valve member 912 and the male end 902 and on the other side by the fluid pressure or structure within the medical implement 942.

Figure 31:
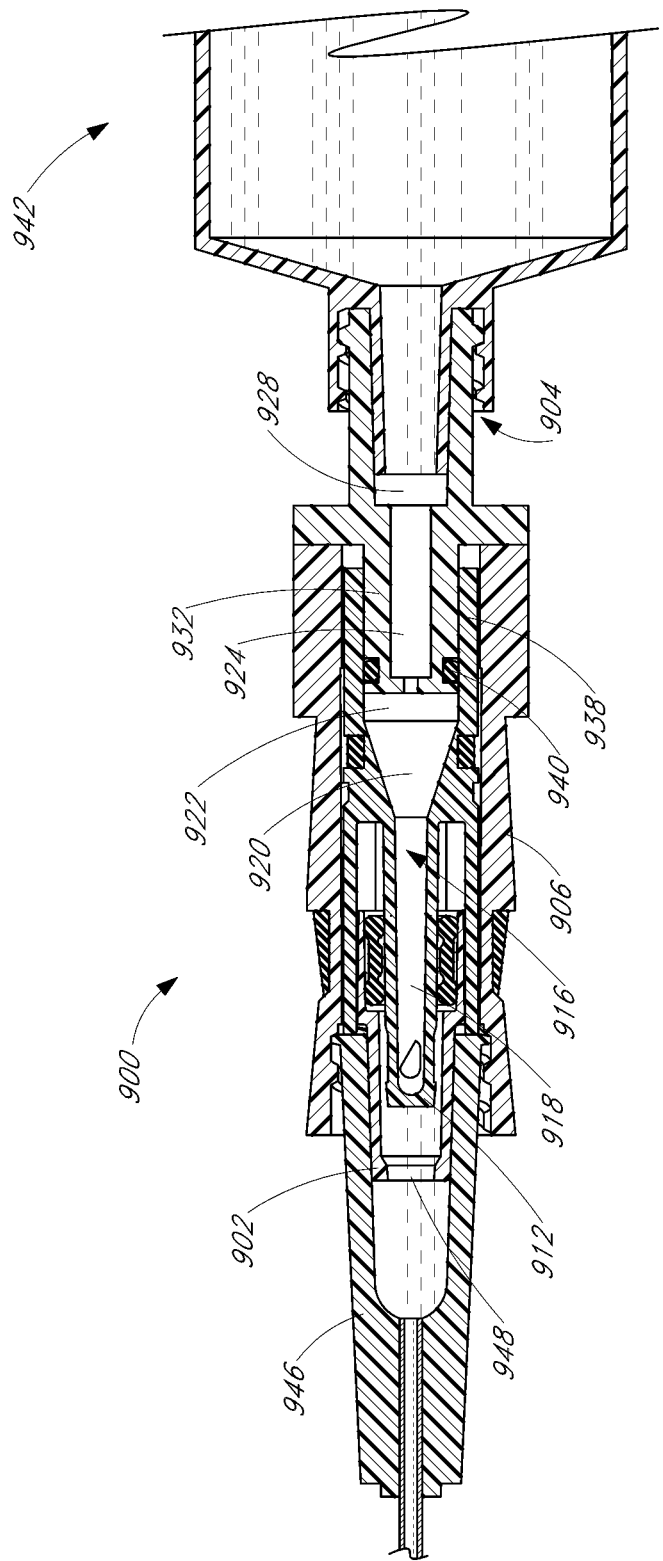
FIG. 31 is a cross-sectional view of the connector and syringe of FIG. 30 engaged with a tube having a female luer attachment portion. At this stage, fluid flow is permitted through this assembly.

As illustrated in FIG. 31, when the valve member 912 is urged away from the male end 902 upon attachment of connector 900 to another medical implement (such as the female connector housing 946 of a plastic IV tube), internal conduit 938 moves in the direction of the female end 904, overlapping at least a portion of internal conduit 932. Fluid is then permitted to flow between medical implements 942, 946 by way of the connector 900. In this second, opened configuration or position, region 922 is smaller than it was in the first, closed configuration or position (see FIG. 30). On the other hand, regions 918, 920, and 928 generally remain about the same size. In some embodiments, including some in which the valve member 912 does not have an internal flow path, a region of changing volume within the connector 900 can be provided by overlapping structures in sliding engagement without directing the fluid flow through the valve member 912. For example, if the valve member is solid, it can be advanced into and withdrawn from conduit 932, and a suitable opening (e.g. in conduit 932 or base 934) can permit fluid to flow through the housing 906 to the male end 902. In some embodiments, including some in which the valve member 912 does not have an internal flow path, the valve member could include a sleeve that can be overlapped over conduit 932 and a suitable opening (e.g. in conduit 932 or base 934) can permit fluid to flow through the housing 906 to the male end 902.

In some embodiments, upon disconnection of the medical implement 946 from the connector 900, the male end 902 can automatically close when the valve member 912 moves within the housing 906 toward the male end under the biasing force of the resilient element 910. In certain circumstances, the movement of a valve member within a fluid passageway could push a small volume of fluid within the male end through the male opening and outside of the connector, resulting in a drip induced by the closing of the valve. However, in the illustrated embodiment, such a drip is generally prevented or minimized.

Figure 32:
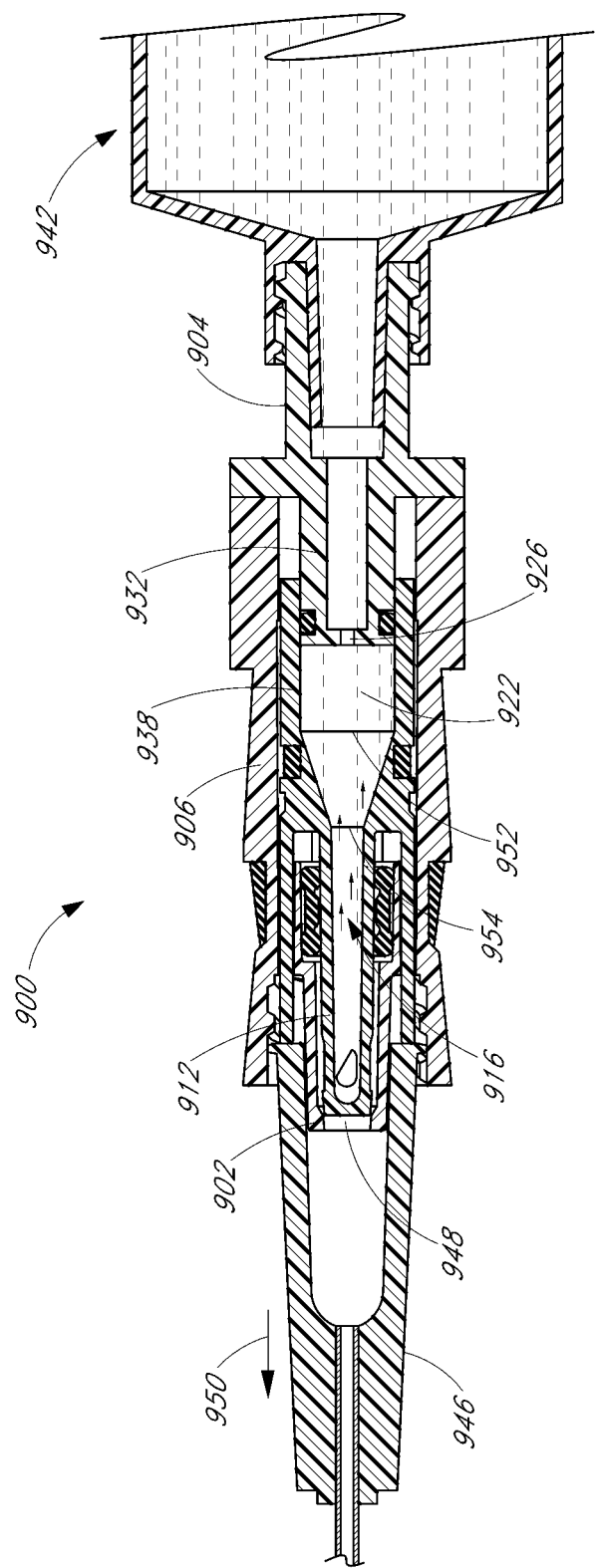
FIG. 32 is another cross-sectional view of the connector, syringe, and tube of FIG. 31. At this stage, the connector is in the process of closing.

As shown in FIG. 32, as the medical implement 946 and the valve member 912 advance in the direction of arrow 950, the region of overlap between internal conduits 932, 938 can decrease and the volume of region 922 of the fluid passageway 916 can increase. The volume of region 922 can eventually return to its approximate original volume in the closed configuration (see FIG. 30). The expanding volume of region 922 during closure of the male luer urges fluid from elsewhere in the passageway 916 to move into region 922.

In some embodiments, the growing void in region 922 cannot be filled by fluid between region 922 and the syringe or other medical implement 942 because the movement of such fluid is prevented by structures in the medical implement 942 (such as the stem seal within the syringe, not shown). Moreover, in some embodiments, such as that shown in FIG. 32, the opening 926 between region 922 and the end of the female connector 904 is substantially smaller than the openings 952, 954 between regions 922, 920, and the remainder of the fluid passageway 916 within the male luer. In this configuration, there can be less fluid resistance within the male end 902 than within the female end 904. In some embodiments, the cross-sectional area of opening 926 is less than one-half the cross-sectional area of opening 954. In some embodiments, the cross-sectional area of opening 926 is less than one-quarter the cross-sectional area of opening 954. In some embodiments, the cross-sectional area of opening 926 is less than one-fifth the cross-sectional area of opening 954. This configuration makes it more likely that fluid will be drawn from the male end 902 into the connector rather than from the female end 904.

As a result of the void in region 922, fluid between the valve member 912 and the internal wall of the male end 902 is pulled back within the body of the connector 900 toward region 922 rather than being pushed out of the male opening. As the connector 900 closes, the increasing volume in the interior of the connector 900 tends to draw fluid in from the opening 948 rather than permit the fluid to be expelled. In the illustrated embodiment, this is achieved in part by providing a cross-sectional area of the region 922 that is substantially larger than the cross-sectional area of opening 948. The volume in region 922 increases faster than the volume in 948 decreases as the valve member 912 moves into the closed position. In some embodiments, the rigid walls of the overlapping internal conduits 938, 932 can sustain extended repeat movement and usage with minimal wear. The walls of the overlapping internal conduits 938, 932 generally do not deform or weaken, which could otherwise affect the size of the void created inside of the connector during closure. Moreover, the walls of the overlapping internal conduits 938, 932 generally do not bulge or buckle under relatively high fluid pressures within the connector, nor do they generally permit the valve member 912 to become misaligned within the internal cavity of the housing 906 under most conditions.

In some embodiments of a closeable male luer connector disclosed herein, it may be difficult to "prime" the connector (i.e., replace air inside of the connector with fluid) without forcing air into one or more medical implements to which the connector is attached. In such embodiments, a separate priming cap can be attached to the male end of the connector. The priming cap can be structured in many different ways.

Figure 33:
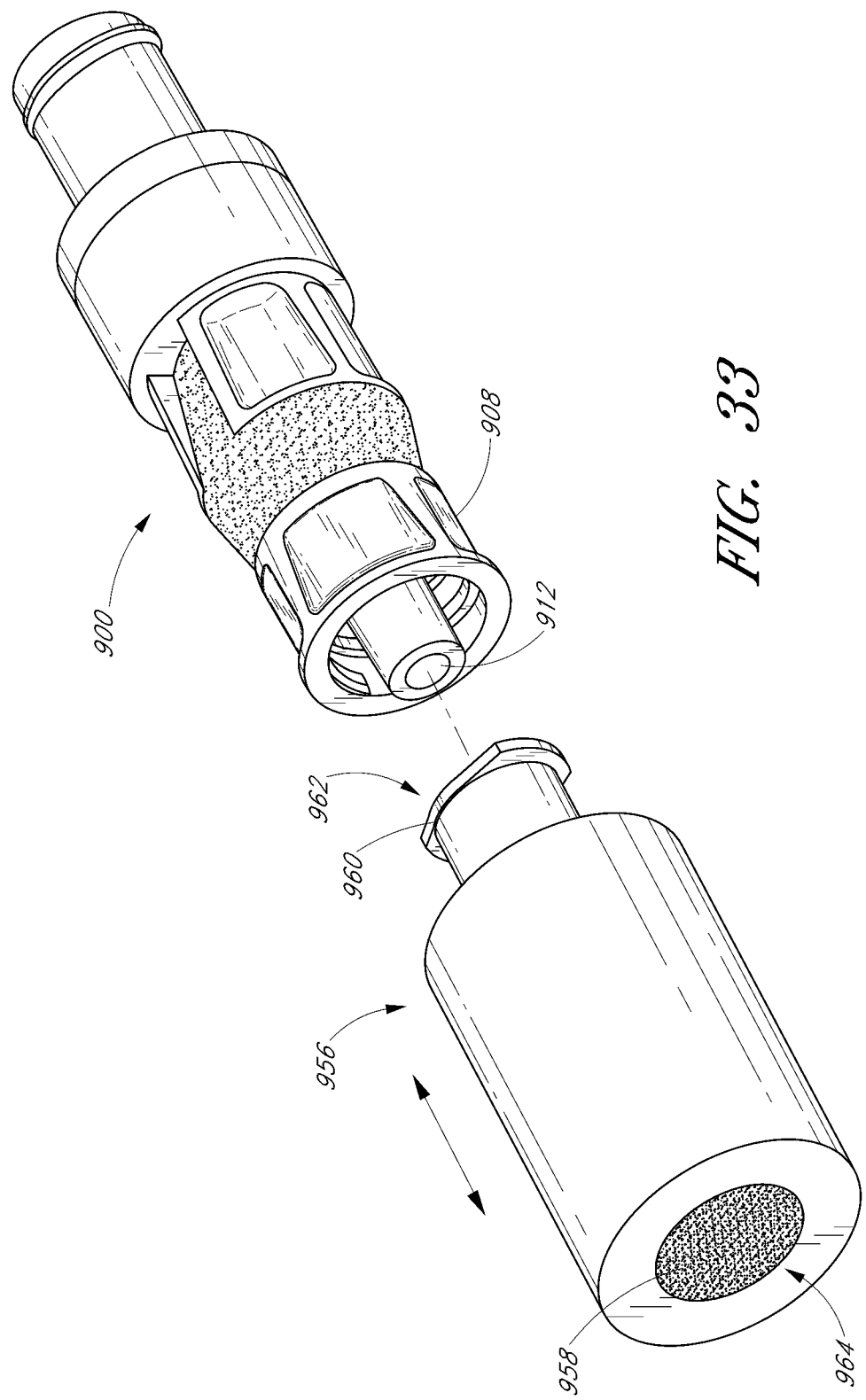
FIG. 33 is a perspective view of the connector of FIG. 27 prior to engagement with an embodiment of a priming cap.

FIG. 33 provides an example of a priming cap 956 that can be used with a closeable male luer connector 900. A suitably configured priming cap can be used with any of the embodiments of the male luer connectors disclosed herein. In some embodiments, the priming cap 956 can include a structure to open the closeable male luer connector 900 (such as a rigid internal conduit, not shown, for pushing against the valve member 912 or a female end 962 with a housing wall 960 configured to abut the struts inside of the shroud 908), permitting fluid to escape from inside of the closeable male luer connector 900. The priming cap 956 can also include an internal fluid passageway (not shown) through which fluid from the opened male luer connector 900 can pass. The fluid passageway can lead to an exit bore 964. The priming cap 956 can also include a filter 958 through which the escaping air can pass but not the advancing liquid. In the illustrated embodiment, the filter 958 is positioned in the exit bore 964. Thus, the air can be evacuated from the male luer connector 900, through the priming cap 956, and out of the exit bore 964, while the liquid generally remains inside the male luer connector 900 and priming cap 956. When priming is completed, the priming cap 956 can be removed and discarded, which automatically closes the closeable male luer connector 900, and another medical implement can be attached to the closeable male luer connector 900. Many other structures and configurations of priming caps also can be used.

Figure 34:
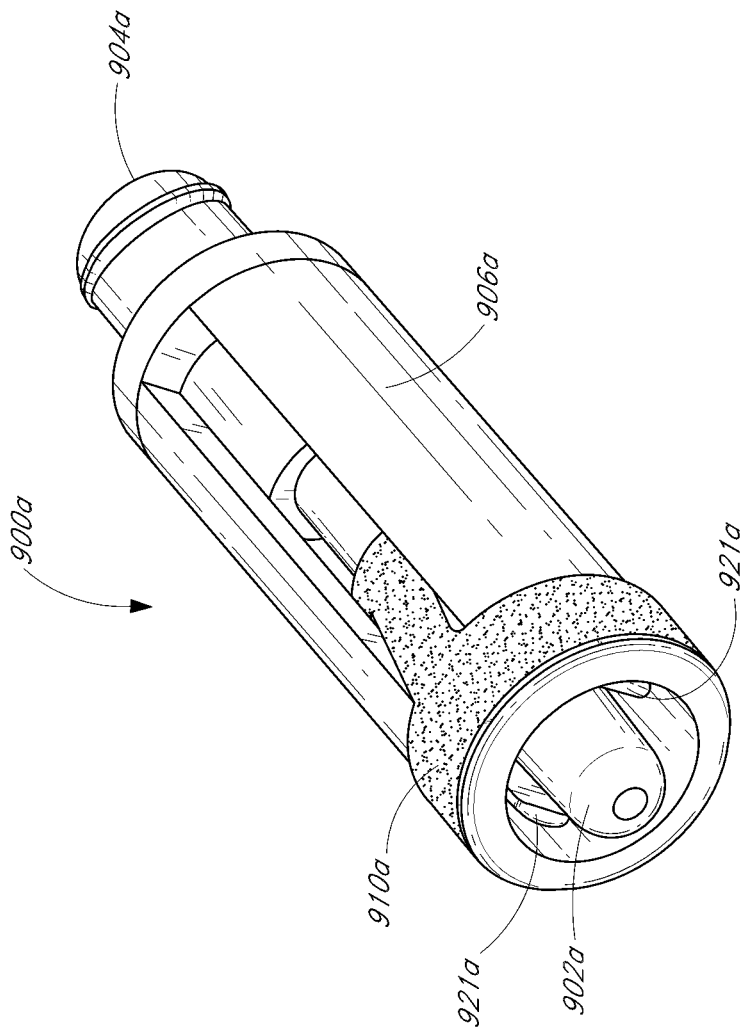
FIG. 34 is a perspective view of another embodiment of a closeable male luer connector.
Figure 35:
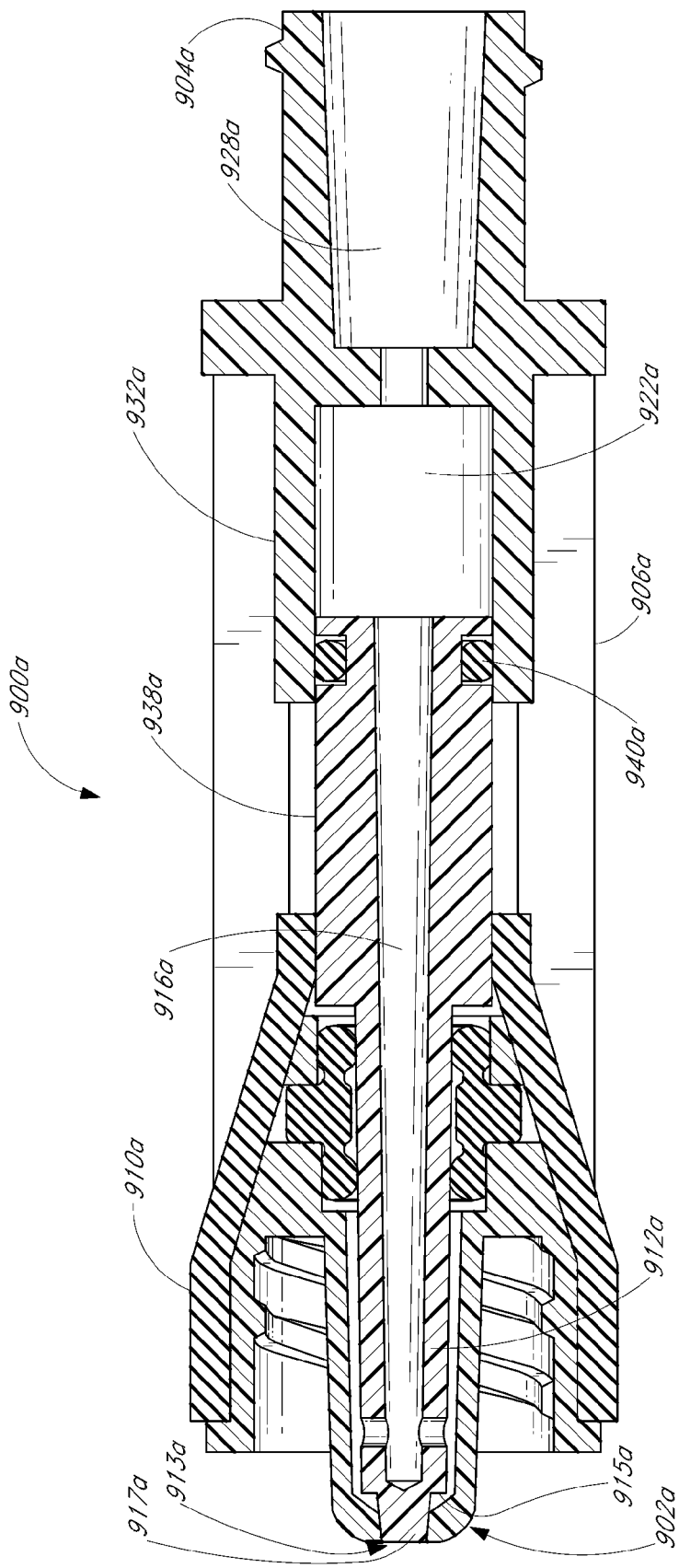
FIG. 35 is a cross-sectional view of the connector of FIG. 34.

FIGS. 34-35 illustrate another embodiment of a closeable male luer connector 900a with a male end 902a, a housing 906a, a female end 904a, and a resilient member 910a, and struts 921a. As shown in FIG. 35, an end 913a of the valve member 912a near the tip of the male end 902a can have a first surface 915a with a larger cross-sectional surface area than a second surface 917a configured to abut an internal side of the tip of the male end 902a. This configuration can assist in creating an interface that is further resistant to leakage from the male luer connector 900a through the male end 902a. In the embodiment of FIG. 35, the internal conduit 938a is smaller in cross section than is the internal conduit 932a. The relative moment between conduits 932a, 938a produces a change in the volume of region 922a, as in the embodiment illustrated in FIGS. 27-32. A resilient seal 940a prevents or minimizes fluid leakage at the interface between the conduits 932a, 938a. When the closeable male luer connector 900a is in the first, closed position, as shown, the volume of region 922a is larger than when the closeable male luer connector 900a is in the second, opened position. Internal passageway 916a may have straight walls such that the passageway 916a maintains a relatively constant cross-sectional area. In some embodiments, the walls of passageway 916a may include a taper. In many respects, the closeable male luer connector 900a functions in a similar manner to the closeable male luer connector 900 of FIGS. 27-32.

Figure 36:
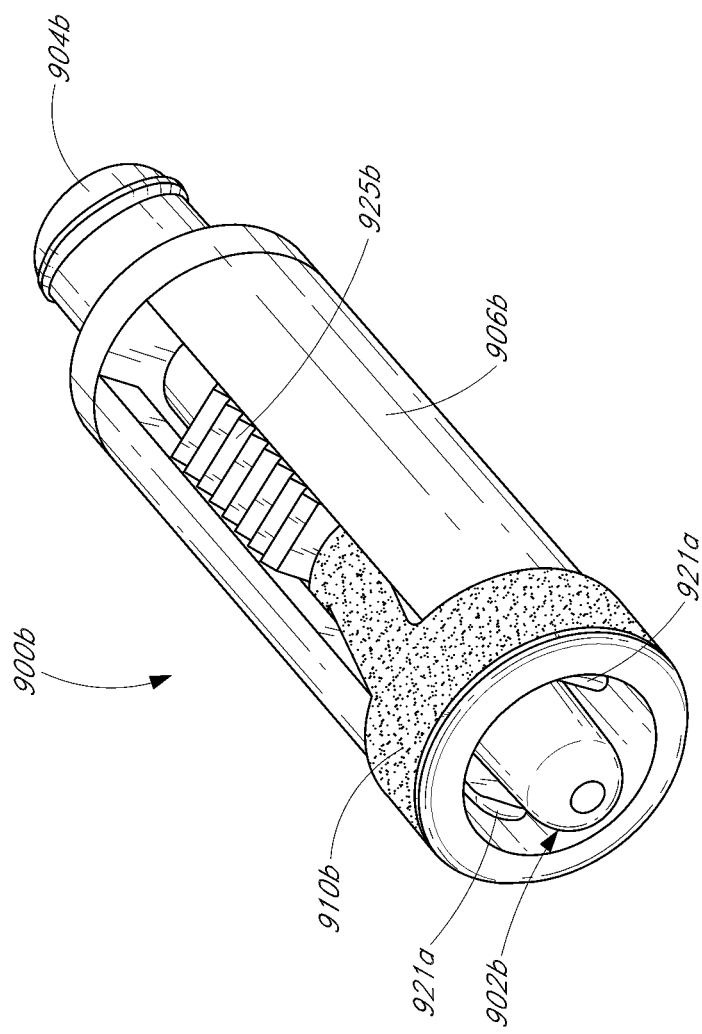
FIG. 36 is a perspective view of another embodiment of a closeable male luer connector.
Figure 37:
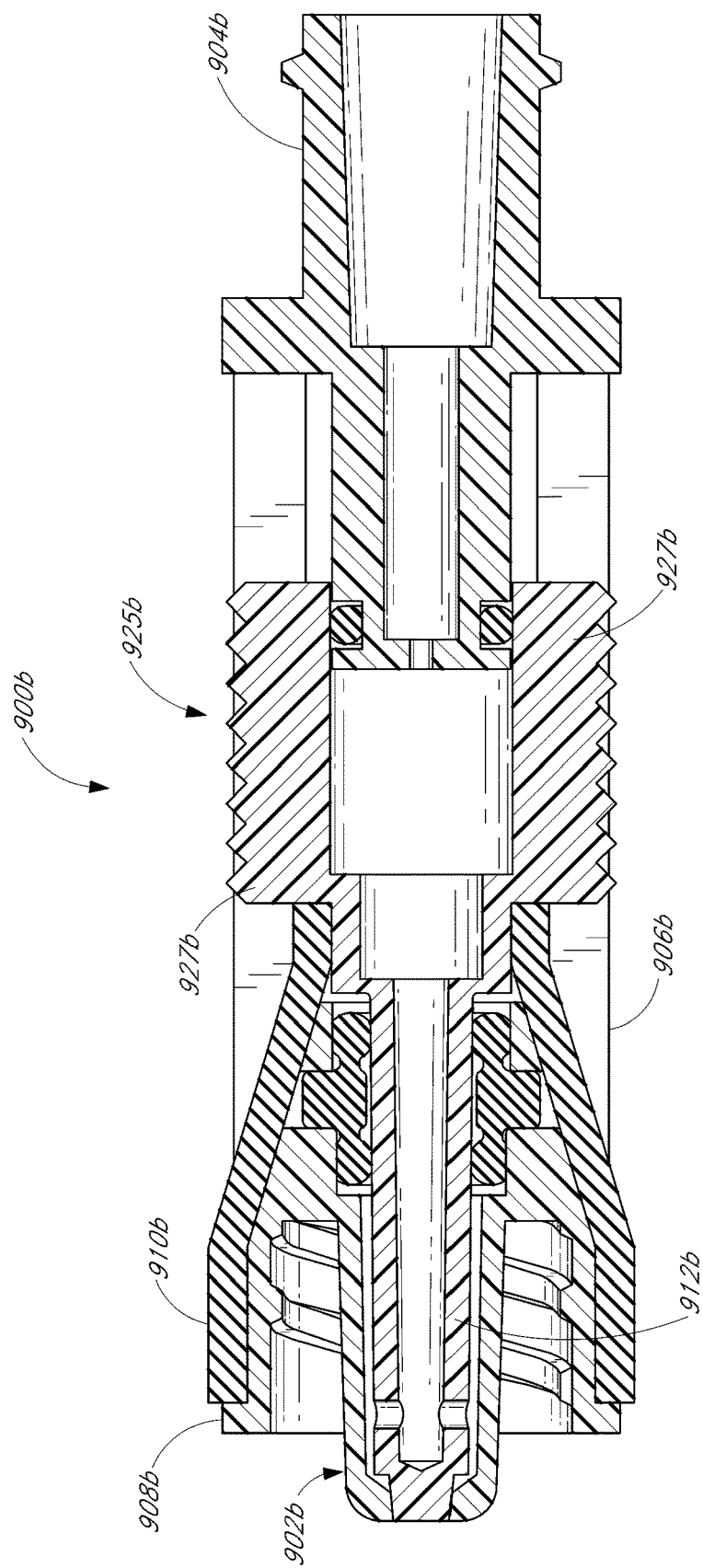
FIG. 37 is a cross-sectional view of the connector of FIG. 36.

FIGS. 36-37 illustrate another embodiment of a closeable male luer connector 900b with a male end 902b, a housing 906b, a female end 904b, and a resilient member 910b. This embodiment also includes an actuator 925b for manually opening and closing the male luer connector 900b. Many different types of manual actuators can be used, including those employing springs, buttons, levers, and other structures. In the illustrated embodiment, the valve member 912b includes at least one lateral side 927b that can be contacted by the fingers and advanced toward either the male end 902b or toward the female end 904b. In the illustrated embodiment, the valve member 912b includes struts 921b within the shroud 908b. As such, when the lateral side 927b is moved toward the male end 902b, the male luer connector 900b can be closed unless the male luer connector 900b is attached at its male end 902b to another medical implement. When the lateral side 927b is moved toward the female end 904b, the male luer connector 900b can be opened, even when another medical implement has not yet been attached at the male end 902b of the connector 900b. As shown in FIG. 36, the exterior surface of the actuator 925b can be serrated or otherwise textured to avoid slipping of the fingers, and the exterior surface of the actuator 925b can be positioned slightly below the outer perimeter of the housing 906b to avoid unintentional opening or closing of the connector 900b, especially during installation or other movement of the connector 900b. In some embodiments, the valve member 912b may not include struts within the shroud 908b.

The actuator 925b, or some other structure for manual opening and closing of the connector 900b, can be particularly advantageous in some applications during priming of the closeable male luer connector 900b. It allows for the connector 900b to be opened while air within the connector 900b is evacuated into the environment before the connector 900b is attached to another implement (which would otherwise cause the evacuated air to be forced into such other implement). A priming cap may not be necessary when manual means are provided for opening and closing the connector 900b.

Figure 38:
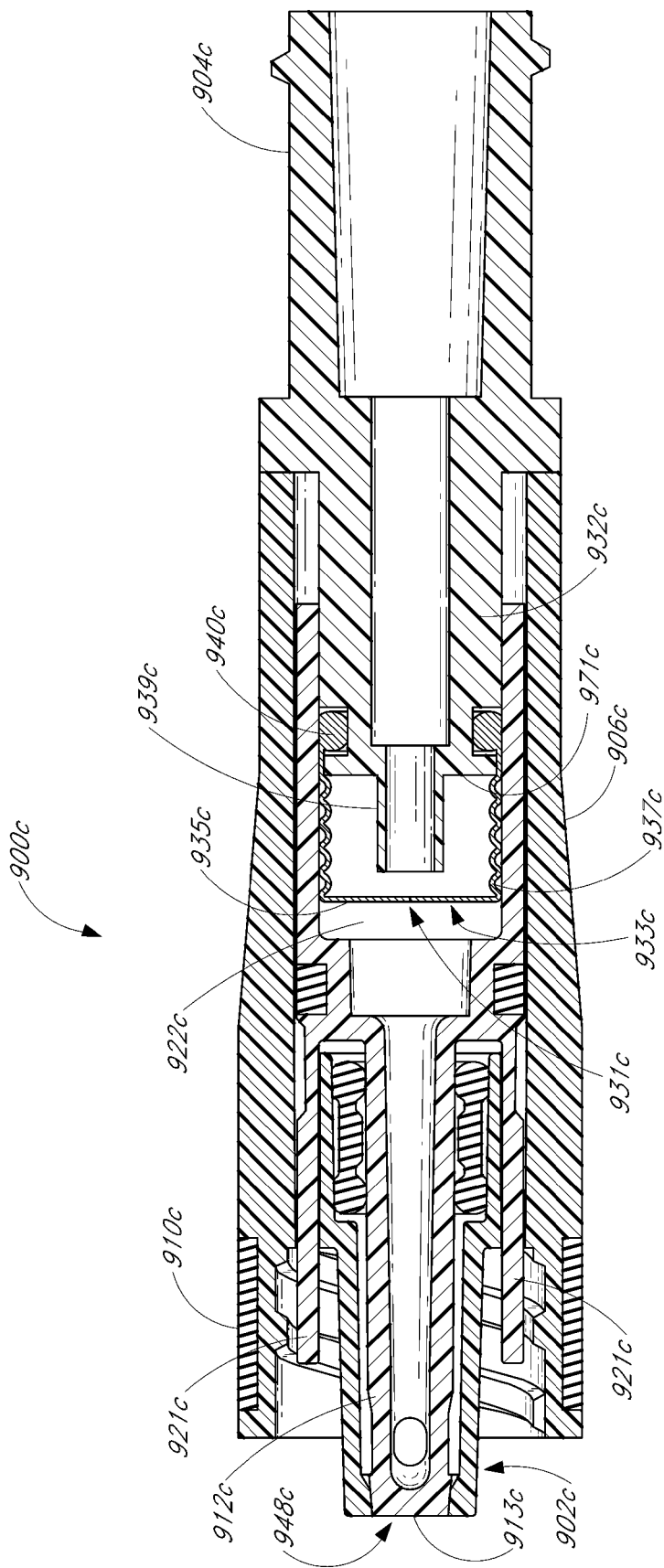
FIG. 38 is a cross-sectional view of another embodiment of a closeable male luer connector.
Figure 39:
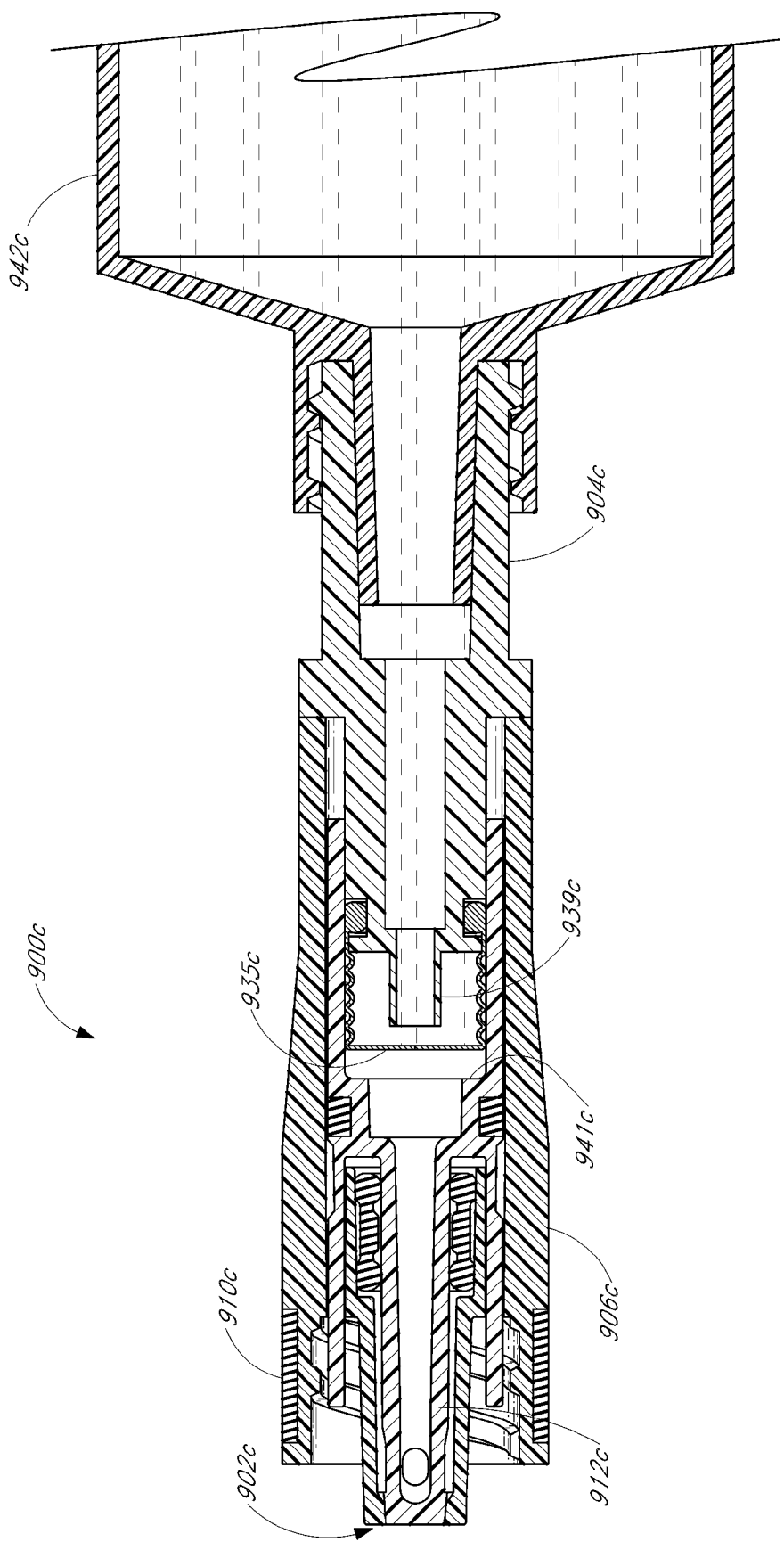
FIG. 39 is a cross-sectional view of the connector of FIG. 38 engaged with a syringe with a male luer tip. At this stage, fluid flow is impeded through the male luer connector.
Figure 39A:
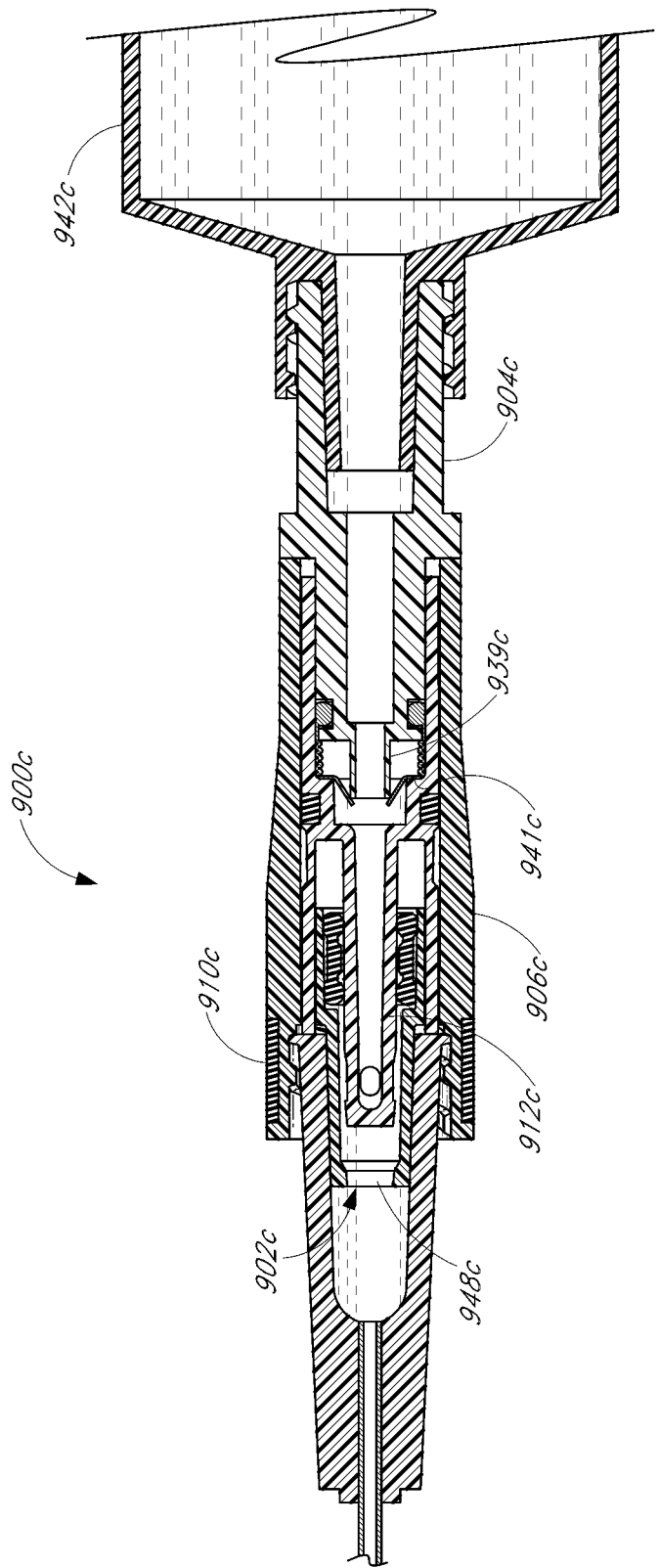
FIG. 39A is a cross-sectional view of the connector and syringe of FIG. 39 engaged with a tube having a female luer attachment portion. At this stage, fluid flow is permitted through this assembly.

FIGS. 38-39A illustrate another embodiment of a closeable male luer connector 900c with a male end 902c, a housing 906c, a female end 904c, and a resilient member 910c. This embodiment also includes an internal structure for impeding or halting the flow of fluid. A resilient covering 933c is positioned generally within region 922c. The covering 933c can include a forward surface 935c, which is generally flat in the illustrated embodiment, a slit 931c, and a sidewall 937c. The sidewall 937c can be corrugated to facilitate axial compression of the covering 933c. The sidewall 937c can be connected to a seal element 940c as shown, or the sidewall 937c can be attached to a forward end 971c of the conduit 932c. The conduit 932c can be in fluid communication with a secondary conduit 939c.

As shown in FIG. 39A, when the valve member 912c is moved toward the female end 904c, an internal shoulder 941c on the valve member 912c comes into contact with the forward surface 935c of the covering 933c, causing the covering 933c to compress or otherwise move in the direction of the female end 904c. On the other hand, the secondary conduit 939c generally remains stationary and abuts against the other side of the forward surface 935c of the covering 933c. The opposing forces exerted against the covering 933c by the shoulder 941c and the conduit 939c cause the covering to bend and the slit 931c opens up to permit fluid flow through the connector 900c. The selective opening of the covering 933c (or another type of internal fluid impedance structure) can be accomplished in many other ways and in many other configurations. The selective opening within the connector 900c allows the female end of the region 922c to close or substantially close before the end 913c of the valve member 912c engages the opening 948c of the male end 902c of the connector 900c. With one end closed and the region 922c expanding as the valve member 912c continues to move toward the male end 902c, the increasing volume urges fluid from the male end 902c and into the region 922c.

Figure 40:
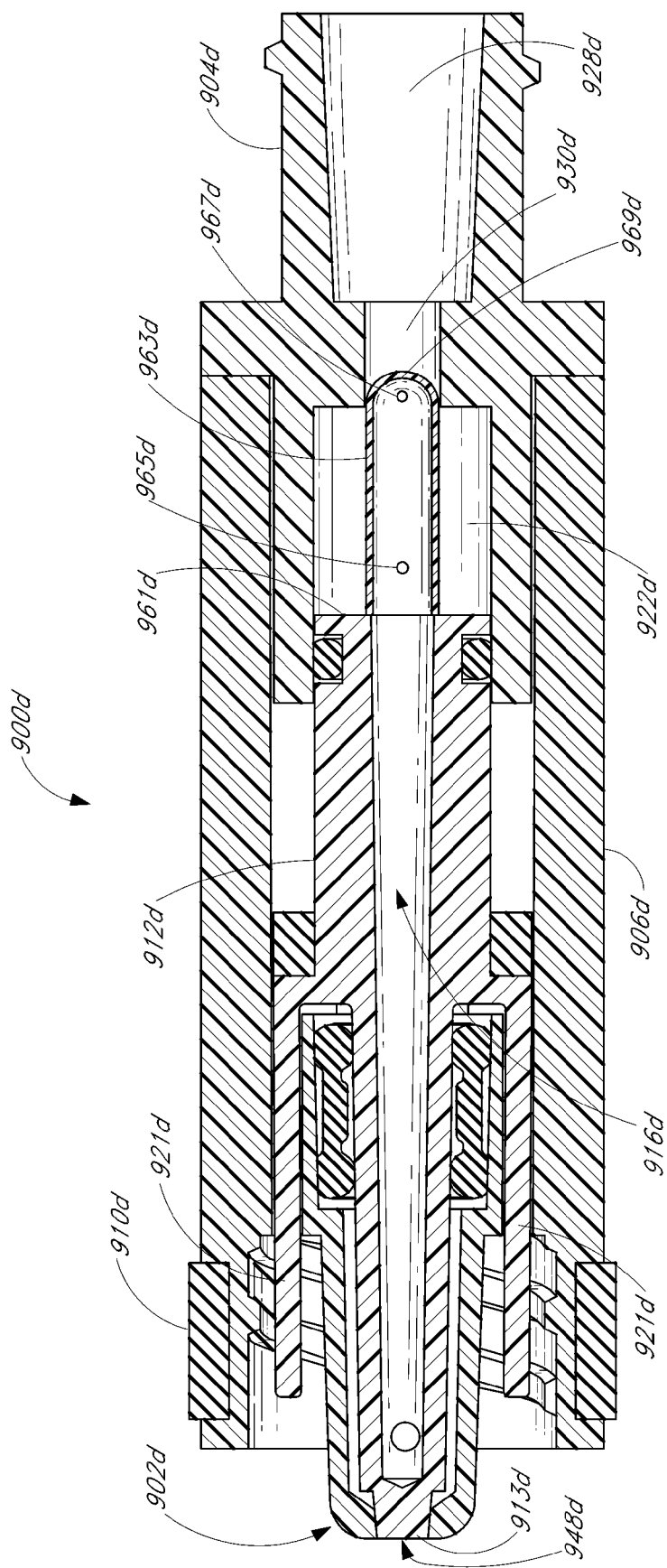
FIG. 40 is a cross-sectional view of another embodiment of a closeable male luer connector.

FIG. 40 illustrates another embodiment of a closeable male luer connector 900d with a male end 902d, a housing 906d, a female end 904d, and a resilient member 910d. As with the embodiment of FIGS. 38-39, this embodiment also includes an internal structure for impeding or halting the flow of fluid between the female end 904d and the internal cavity of the connector 900d. On an end of the valve member 912d, a fluid chamber 963d is positioned in fluid communication within the passageway 916d of the valve member 912d. In the closed position of the illustrated embodiment, the fluid chamber 963d has a hole 965d positioned in the region 922d and a hole 967d positioned in the passage 930d, between region 922d and the region 928d of the female end 904d. In many circumstances, the flow of fluid is blocked or diminished between the female end 904d into the interior of the connector 900d due to the close peripheral fit between the conduit 963d and the passage 930d. However, when the valve member 912d is advanced toward the female end 904d, and the tip 969d of the fluid chamber 963d moves out of the passage 930d and in the direction of the female end 904d, the hole 967d becomes exposed to the region 928d of the female end 904d. This enables fluid communication between the female end 904d and the interior of the connector 900d. When the valve member 912d is returned to its original closed position, the fluid chamber 963d returns to its position within the region 922d and the tip 969d is positioned within the passage 930d, once again preventing or impeding fluid flow between the female end 904d and the interior of the connector 900d. As the valve member 912d returns to its original closed position, fluid flow between the female end 904d and the interior of the connector 900d is generally impeded as soon as the hole 967d moves into passage 930d, preferably before the end 913d of the valve member 912d engages the opening 948d of the male end 902d of the connector 900d. With fluid flow in the region 922d in the direction of the female end 904d of the connector 900d impeded, fluid is preferably drawn from the male end 902d and into the expanding region 922d. Many other structures and configurations can be used to accomplish the selective communication of fluid between the female end 904d and the interior of the connector 900d.

Figure 41:
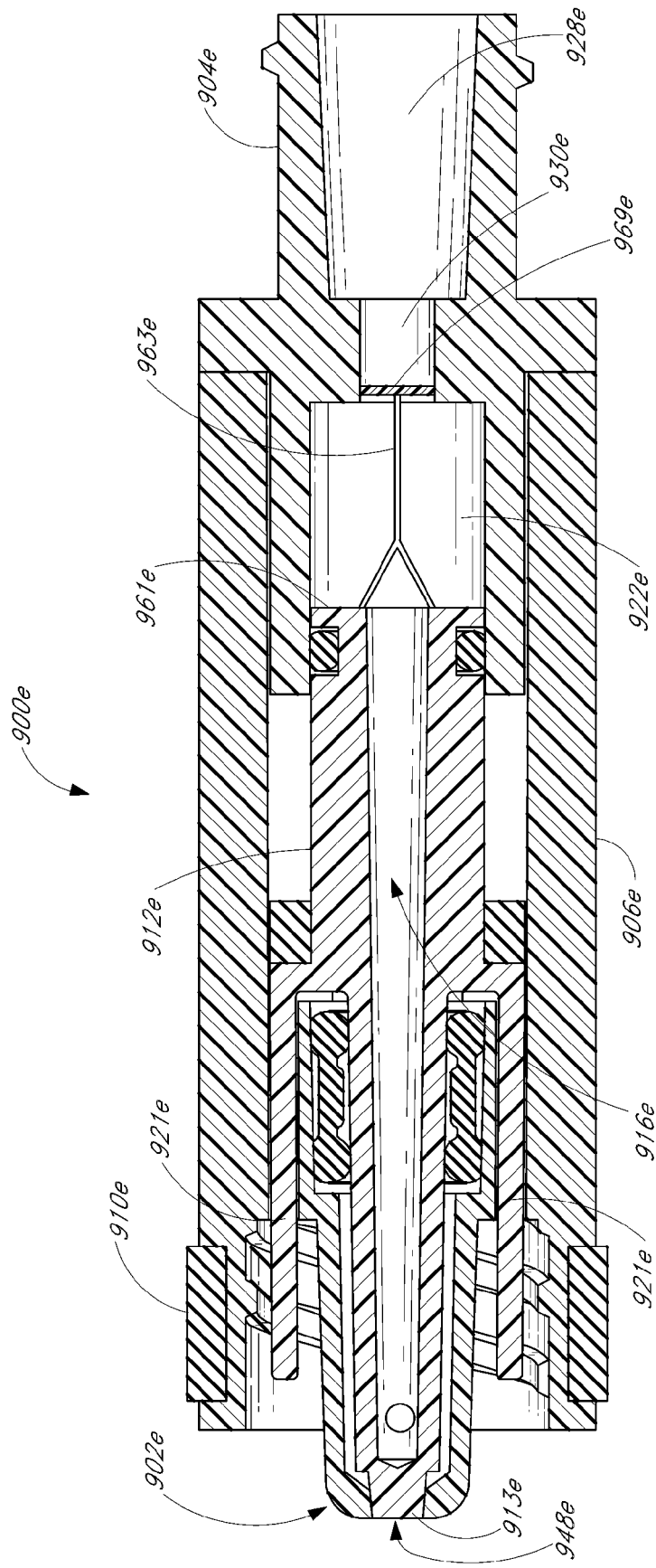
FIG. 41 is a cross-sectional view of another embodiment of a closeable male luer connector.

FIG. 41 illustrates another embodiment of a closeable male luer connector 900e with a male end 902e, a housing 906e, a female end 904e, and a resilient member 910e. As with the embodiments of FIGS. 38-40, this embodiment also includes an internal structure for impeding or halting the flow of fluid between the female end 904e and the internal cavity of the connector 900e. On an end of the valve member 912e, a poppet 963e is positioned in fluid communication within the passageway 916e of the valve member 912e. Poppet 963e may include a first end engaging an outer surface 961e of the valve member 912e and a second end 969e. Alternatively, poppet 963e may be formed integrally with the valve member 912e. The walls of the poppet 963e generally rigid and generally do not deform or weaken. Moreover, the walls of the poppet 963e generally do not bulge or buckle under relatively high fluid pressures within the connector, nor do they generally permit the second end 969e to become misaligned within the internal cavity of the connector 900e under most conditions. Many configurations of the poppet 963e are possible. For example, the walls of the poppet 963e near the surface 961e may include holes or slits to facilitate fluid flow therethrough. The walls may be formed from legs extending from surface 961e with separation between the legs to facilitate fluid flow therethrough. In some embodiments, the poppet 963e includes 3 legs. In some embodiments, the poppet 963e includes 4 or more legs.

In the closed position of the illustrated embodiment, the second end 969e of poppet 963e is positioned in the passage 930e between region 922e and the region 928e of the female end 904e. In many circumstances, the flow of fluid is blocked or diminished between the female end 904e into the interior of the connector 900e due to the close peripheral fit between the second end 969e of the poppet 963e and the passage 930e. However, when the valve member 912e is advanced toward the female end 904e, at least a portion of the second end 969e of the poppet 963e moves out of the passage 930e and in the direction of the female end 904e, enabling fluid communication between the female end 904e and the interior of the connector 900e. When the valve member 912e is returned to its original closed position, the poppet 963e returns approximately to its original position within the region 922e and the second end 969e is positioned within the passage 930e, once again preventing or impeding fluid flow between the female end 904e and the interior of the connector 900e. The second end 969e may include one or more flanges (not shown) extending in the direction of the male end 902e of the connector 900e. These flanges would at least partially remain within the passage 930e when the connector 900e is in the opened position to assist maintaining the axial alignment of the poppet 963e. As the valve member 912e returns to its original position, fluid flow between the female end 904e and the interior of the connector 900e is generally impeded as soon as the second end 969e moves into passage 930e, preferably before the end 913e of the valve member 912e engages the opening 948e of the male end 902e of the connector 900e. With fluid flow in the region 922d in the direction of the female end 904d of the connector 900d impeded, fluid is preferably drawn from the male end 902d and into the expanding region 922d. Many other structures and configurations can be used to accomplish the selective communication of fluid between the female end 904e and the interior of the connector 900e.

As described above, some medications, including those used during chemotherapy, can be harmful in certain forms of exposure to a patient. For example, exposure to the skin can sometimes result in a chemical burn. Inhalation of aerosolized forms of some medications can be harmful. Thus, control over the containment of the medication is highly desirable.

At present, some potentially harmful medications are distributed in sealed vials. The medication is removed from the vial by inserting a needle, and drawing the medication into a syringe. The needle is then withdrawn from the vial and the medication can be dispensed. However, by inserting the needle into the medication for drawing into the syringe, medication is disposed on the outside of the needle, which can inadvertently come in contact with the skin and cause harm. Alternatively, an injector which penetrates the vial with a withdrawal mechanism can be used. In such an injector, the medication is drawn through the mechanism and passed directly to a needle for injection without the additional step of withdrawing the mechanism from the vial. Even if such an injector is used, there is still the possibility of latent medication remaining on the needle used to inject the medication, or on the mechanism after the vial is decoupled.

Additionally, some medications can be distributed by attaching a needle to a syringe with the medication located therein. The engaged syringe with medication and needle is sterilized and placed into a vacuum-sealable container. The container is then evacuated and sealed. This type of arrangement can result in the draw of medication out through the syringe when the container is evacuated. While in the sealed container, the medication may aerosolize or coat the outer surface of the components.

Additionally, when the ambient atmospheric pressure of the treatment location is different, particularly lesser, than that of the internal pressure of the medication within a container, there is the possibility that an uncontrolled spray of the medication occurs when fluid communication between the medication and the ambient atmosphere occurs. For example, medication may escape when a vial with a greater internal pressure than the ambient atmosphere is penetrated by a needle for drawing the medication into a syringe. Alternatively, medication may escape when the needle is withdrawn from the vial before the vial seal completely closes.

With a closeable male luer, flow of the medication out of a syringe with a needle is inhibited, except during desired application. For example, in some embodiments, a syringe with a closeable male luer connected will not leak medication when packaged for shipment, even if the package is vacuum-sealed. Once the package is opened, the male luer connector can be engaged with a female luer connector of an IV tube, for example, and the medication dispensed only when the connection is engaged. Following flow of the medication from the syringe through the engaged connectors and into the IV tube, the male luer connector can be disengaged from the female luer connector. As described above, the male luer connector can close on disengagement, preventing excess flow through the connector. When a closeable female luer connector, such as a Clave® connector sold by ICU Medical, San Clemente, Calif., is used, flow is inhibited from exiting the female connector as well.

Additionally, a syringe with a closeable male luer can be engaged with a needle as described above. Flow through the needle can thus be controlled by proper use of the closeable male luer connector.

Medication can also be disposed within a syringe with an integrally formed, and/or permanently attached, closeable male luer.

Thus, direct exposure of the dangerous medications described can be essentially limited to the highly controlled environments where the medications are produced and contained. Such medications can be placed in a syringe with a closeable male luer connector prior to distribution for use, minimizing the risk of inadvertent exposure of the medication during use of the medication.

Any features of the embodiments shown and/or described in the figures that have not been expressly described in this text, such as distances, proportions of components, etc. are also intended to form part of this disclosure. Additionally, although this invention has been disclosed in the context of various embodiments, features, aspects, and examples, it will be understood by those skilled in the art that the present invention extends beyond the specifically disclosed embodiments to other alternative embodiments and/or uses of the invention and obvious modifications and equivalents thereof. Accordingly, it should be understood that various features and aspects of the disclosed embodiments can be combined with, or substituted for, one another in order to perform varying modes of the disclosed inventions. Moreover, any component or combination of components disclosed herein can be used in other structures or configurations of medical connectors. Thus, it is intended that the scope of the present invention herein disclosed should not be limited by the particular disclosed embodiments described above, but should be determined only by a proper reading of the claims.

The following is claimed:

1. A medical connector configured to receive a male luer end of a medical article, the medical connector comprising:
   a housing having a proximal portion and a distal portion;
   a female end in the proximal portion, the female end configured to receive the male luer end of the medical article;
   a male end having a male luer;
   a rigid valve member being longitudinally movable along a central axis of the housing between an open position to a closed position, the valve member being formed of a single piece of material, the valve member comprising:
      an internal fluid channel,
      a closed distal end,
      at least one opening adjacent the closed distal end,
      an open-ended proximal end surface having a cross-sectional width larger than the closed distal end, and
      the internal fluid channel tapering adjacent to the open-ended proximal end surface;
   an elastically deformable resilient member at least partially exposed outside the housing, the resilient member configured to couple the valve member and the housing; and
   a sealing element at least partially disposed within the distal portion of the housing at a location proximal from the male luer, the sealing element configured to inhibit fluid communication through the housing between an interior surface of the male luer and an interior surface of the proximal portion of the housing.

2. The medical connector of claim 1, wherein the sealing element comprises a sidewall and at least one protrusion extending radially outwardly form from the side wall.

3. The medical connector of claim 2, wherein the protrusion is axially secured in both a proximal direction and a distal direction.

4. The medical connector of claim 1, wherein the male luer comprising a first region and a second region, the second region having an internal cross-sectional width that is smaller than an internal cross-sectional width of the first region of the male luer.

5. The medical connector of claim 4, wherein at least a portion of the closed distal end of the valve member is positioned within the second region of the male luer when the valve member is in the closed position.

6. The medical connector of claim 1, wherein the elastically-deformable resilient member is in an extended position when the valve member is in the open position.

7. A medical connector configured to receive a male luer end of a medical article, the medical connector comprising:
   a housing having a proximal portion and a distal portion;
   a female end in the proximal portion, the female end configured to receive the male luer end of the medical article;
   a male end having a male luer;
   a rigid valve member being longitudinally movable along a central axis of the housing between an open position to a closed position, the valve member comprising:
      an internal fluid channel,
      a closed distal end, and
      at least one opening adjacent the closed distal end,
      wherein at least a portion of the closed distal end of the valve member is positioned within the male luer when the valve member is in the closed position;

a resilient member configured to couple the valve member and the housing; and a sealing element at least partially disposed within the distal portion of the housing at a location proximal from the male luer, the sealing element configured to inhibit fluid communication through the housing between an interior surface of the male luer and an interior surface of the proximal portion of the housing, the sealing element comprising a sidewall and at least one protrusion extending radially outwardly from the side wall, the protrusion being axially secured in both a proximal direction and a distal direction.

8. The medical connector of claim 7, wherein the at least one protrusion is configured to inhibit the sealing element from moving within the distal portion of the housing.

9. The medical connector of claim 7, wherein the resilient member is at least partially exposed outside the housing.

10. The medical connector of claim 7, wherein the resilient member is elastically-deformable and is in an extended position when the valve member is in the open position.

11. The medical connector of claim 7, wherein the valve member comprises an open-ended proximal end surface.

12. The medical connector of claim 11, wherein the open-ended proximal end surface has a cross-sectional width larger than the closed distal end.

13. The medical connector of claim 7, wherein the sealing element comprises a sidewall and at least one protrusion extending radially outwardly form from the side wall.

14. The medical connector of claim 13, wherein the protrusion is axially secured in both a proximal direction and a distal direction.

* * * * *